(12) United States Patent
MacMillan et al.

(10) Patent No.: US 11,981,704 B2
(45) Date of Patent: May 14, 2024

(54) DECARBOXYLATIVE CONJUGATE ADDITIONS AND APPLICATIONS THEREOF

(71) Applicant: THE TRUSTEES OF PRINCETON UNIVERSITY, Princeton, NJ (US)

(72) Inventors: David MacMillan, Princeton, NJ (US); Daniel Novoa, New York, NY (US); Stefan McCarver, Princeton, NJ (US)

(73) Assignee: THE TRUSTEES OF PRINCETON UNIVERSITY, Princeton, NJ (US)

(*) Notice: Subject to any disclaimer, the term of this patent is extended or adjusted under 35 U.S.C. 154(b) by 203 days.

(21) Appl. No.: 17/469,102

(22) Filed: Sep. 8, 2021

(65) Prior Publication Data

US 2022/0002342 A1 Jan. 6, 2022

Related U.S. Application Data

(62) Division of application No. 15/579,741, filed as application No. PCT/US2016/035716 on Jun. 3, 2016, now Pat. No. 11,136,349.

(60) Provisional application No. 62/171,722, filed on Jun. 5, 2015.

(51) Int. Cl.
| | |
|---|---|
| *C07K 1/113* | (2006.01) |
| *B01J 31/18* | (2006.01) |
| *B01J 35/00* | (2006.01) |
| *C07K 1/107* | (2006.01) |
| *C07K 5/02* | (2006.01) |
| *C25B 3/29* | (2021.01) |

(52) U.S. Cl.
CPC ............. *C07K 1/113* (2013.01); *B01J 31/181* (2013.01); *B01J 31/1815* (2013.01); *B01J 35/004* (2013.01); *C07K 1/107* (2013.01); *C07K 5/0205* (2013.01); *C25B 3/29* (2021.01); *B01J 2231/324* (2013.01); *B01J 2231/348* (2013.01); *B01J 2531/827* (2013.01); *B01J 2540/12* (2013.01); *B01J 2540/22* (2013.01); *B01J 2540/225* (2013.01)

(58) Field of Classification Search
CPC .................................. C07K 1/113; C25B 3/10
See application file for complete search history.

(56) References Cited

U.S. PATENT DOCUMENTS 11,136,349 B2 * 10/2021 MacMillan ............ B01J 31/181

OTHER PUBLICATIONS

Chu et al. Carboxylic Acids as A Traceless Activation Group for Conjugate Additions: A Three-Step Synthesis of +/− Pregabalin. Journal of the American Chemical Society. Jul. 17, 2014, vol. 136, pp. 10886-10889 plus Supporting Information. (Year: 2014).*

* cited by examiner

*Primary Examiner* — Jeffrey E. Russel
(74) *Attorney, Agent, or Firm* — J. Clinton Wimbish; Maynard Nexsen PC

(57) ABSTRACT

Synthetic methods are described herein operable to efficiently produce a wide variety of molecular species through conjugate additions via decarboxylative mechanisms. For example, methods of functionalization of peptide residues are described, including selective functionalization of peptide C-terminal residues. In one aspect, a method of peptide functionalization comprises providing a reaction mixture including a Michael acceptor and a peptide and coupling the Michael acceptor with the peptide via a mechanism including decarboxylation of a peptide reside.

22 Claims, 22 Drawing Sheets

Specification includes a Sequence Listing.

| acidic residue | localization probability | pH = 4.5 | | | pH = 3.5 | | |
|---|---|---|---|---|---|---|---|
| | | trails | | Σ | trails | | Σ |
| E16 | 100% | 1 | 3 | 4 | 0 | 3 | 3 |
| E18 | 100% | 2 | 0 | 2 | 0 | 0 | 0 |
| D21 | 100% | 1 | 0 | 1 | 0 | 1 | 1 |
| E24 | 100% | 4 | 0 | 4 | 1 | 2 | 3 |
| E34 | 100% | 5 | 7 | 12 | 0 | 0 | 0 |
| D39 | 100% | 2 | 0 | 2 | 2 | 1 | 3 |
| E51 | 100% | 1 | 0 | 1 | 0 | 0 | 0 |
| D52 | 99% | 0 | 0 | 0 | 0 | 0 | 0 |
| D58 | 100% | 0 | 1 | 1 | 4 | 2 | 6 | number of each residue with +142 functionalization detected

| acidic residue | localization probability | riboflavin pH = 4.5 | | | riboflavin pH = 3.5 | | | lumiflavin pH = 4.5 | | |
|---|---|---|---|---|---|---|---|---|---|---|
| | | trails | | Σ | trails | | Σ | trails | | Σ |
| E16 | 100% | 5 | 5 | 10 | 3 | 2 | 5 | 2 | 2 | 4 |
| E18 | 100% | 8 | 9 | 17 | 3 | 2 | 5 | 1 | 2 | 3 |
| D21 | 100% | 1 | 0 | 1 | 2 | 2 | 4 | 1 | 0 | 1 |
| E24 | 100% | 2 | 6 | 8 | 5 | 4 | 9 | 2 | 0 | 2 |
| E34 | 100% | 19 | 14 | 33 | 13 | 12 | 25 | 5 | 5 | 10 |
| D39 | 100% | 0 | 0 | 0 | 0 | 0 | 0 | 0 | 0 | 0 |
| E51 | 100% | 2 | 5 | 7 | 2 | 3 | 5 | 4 | 5 | 9 |
| D52 | 99% | 1 | 1 | 2 | 1 | 2 | 3 | 0 | 1 | 1 |
| D58 | 100% | 1 | 0 | 1 | 0 | 0 | 0 | 2 | 0 | 2 | number of each residue with +142 functionalization detected

DECARBOXYLATIVE CONJUGATE ADDITIONS AND APPLICATIONS THEREOF

RELATED APPLICATION DATA

The present application is a divisional of U.S. patent application Ser. No. 15/579,741 filed Dec. 5, 2017 which is a U.S. National Phase of PCT/US2016/035716, filed Jun. 3, 2016, which claims priority pursuant to 35 U.S.C. § 119(e)(1) to U.S. Provisional Patent Application Ser. No. 62/171,722 filed Jun. 5, 2015, each of which are hereby incorporated by reference in their entireties.

STATEMENT OF GOVERNMENT RIGHTS

This invention was made with government support under Grant No. GM103558 awarded by the National Institutes of Health (NIGMS). The government has certain rights in the invention.

SEQUENCE LISTING

The instant application contains a Sequence Listing which has been submitted electronically in ASCII format and is hereby incorporated by reference in its entirety. Said ASCII copy, created on Feb. 1, 2021, is named 060017-00142_SL.txt and is 14,971 bytes in size.

FIELD

The present invention relates to conjugate additions and, in particular, to conjugate additions via decarboxylative mechanisms employing photoredox catalyst.

BACKGROUND

Molecular synthesis plays a critical role in a significant number of industries including the pharmaceutical, biological, biochemical and materials industries. Substantial resources and time are invested in the construction and development of molecular libraries for the characterization and identification of molecular species having commercial promise as intermediates or final products for particular applications. Such libraries, however, are often rendered incomplete by the inability to efficiently synthesize a wide variety of chemical species. Many classes of chemical species, for example, require expensive reagents, complex and time consuming synthetic pathways and/or result in the production of hazardous by-products. Further, some chemical species cannot be synthesized by current technologies. For example, synthetic pathways are not currently available for performing selective chemistries on the C-terminus of proteins in the presence of all other naturally occurring protein functionalities. In view of these deficiencies, new synthetic routes are required.

SUMMARY

Synthetic methods are described herein operable to efficiently produce a wide variety of molecular species through conjugate additions via decarboxylative mechanisms. For example, methods of functionalization of peptide residues are described, including selective functionalization of peptide C-terminal residues. In one aspect, a method of peptide functionalization comprises providing a reaction mixture including a Michael acceptor and a peptide and coupling the Michael acceptor with the peptide via a mechanism including decarboxylation of a peptide reside. In some embodiments, the peptide C-terminal residue undergoes decarboxylative coupling with the Michael acceptor. Alternatively, an interior residue or non-terminal residue comprising a carboxyl side chain can undergo decarboxylative coupling with the Michael acceptor. As described further herein, the resulting coupling product can be a 1,4-addition adduct comprising the peptide and a Michael acceptor residue coupled to a decarboxylated amino acid residue of the peptide.

In another aspect, a method of peptide coupling comprises providing a reaction mixture including a first peptide and a second peptide, the second peptide comprising a Michael acceptor functionalized N-terminal residue and coupling the functionalized N-terminal residue with the first peptide via a mechanism including decarboxylation of a residue of the first peptide. In some embodiments, the first peptide C-terminal residue undergoes decarboxylative coupling with the Michael acceptor functionalized N-terminal residue of the second peptide. In other embodiments, an interior amino acid residue of the first peptide undergoes decarboxylative coupling with the Michael acceptor functionalized N-terminal residue of the second peptide.

In a further aspect, methods of intramolecular peptide cyclization are described herein. For example, a method of intramolecular peptide cyclization comprises providing a reaction mixture comprising a peptide including a C-terminal residue and a Michael acceptor functionalized N-terminal residue and coupling the C-terminal residue with the functionalized N-terminal residue via a mechanism including decarboxylation of the C-terminal residue. Coupling of the Michael acceptor functionalized N-terminal residue with the C-terminal residue results in cyclization of the peptide.

Moreover, general methods of conjugate addition are also described herein. A method of conjugate addition comprises providing a reaction mixture including a Michael acceptor and a substrate having a carboxyl group and coupling the Michael acceptor and substrate via a mechanism including decarboxylation of the substrate.

These and other embodiments are further described in the following detailed description.

BRIEF DESCRIPTION OF THE DRAWINGS

FIG. 7A discloses SEQ ID NOS 46-52, respectively, in order of appearance.

DETAILED DESCRIPTION

Figure 1:
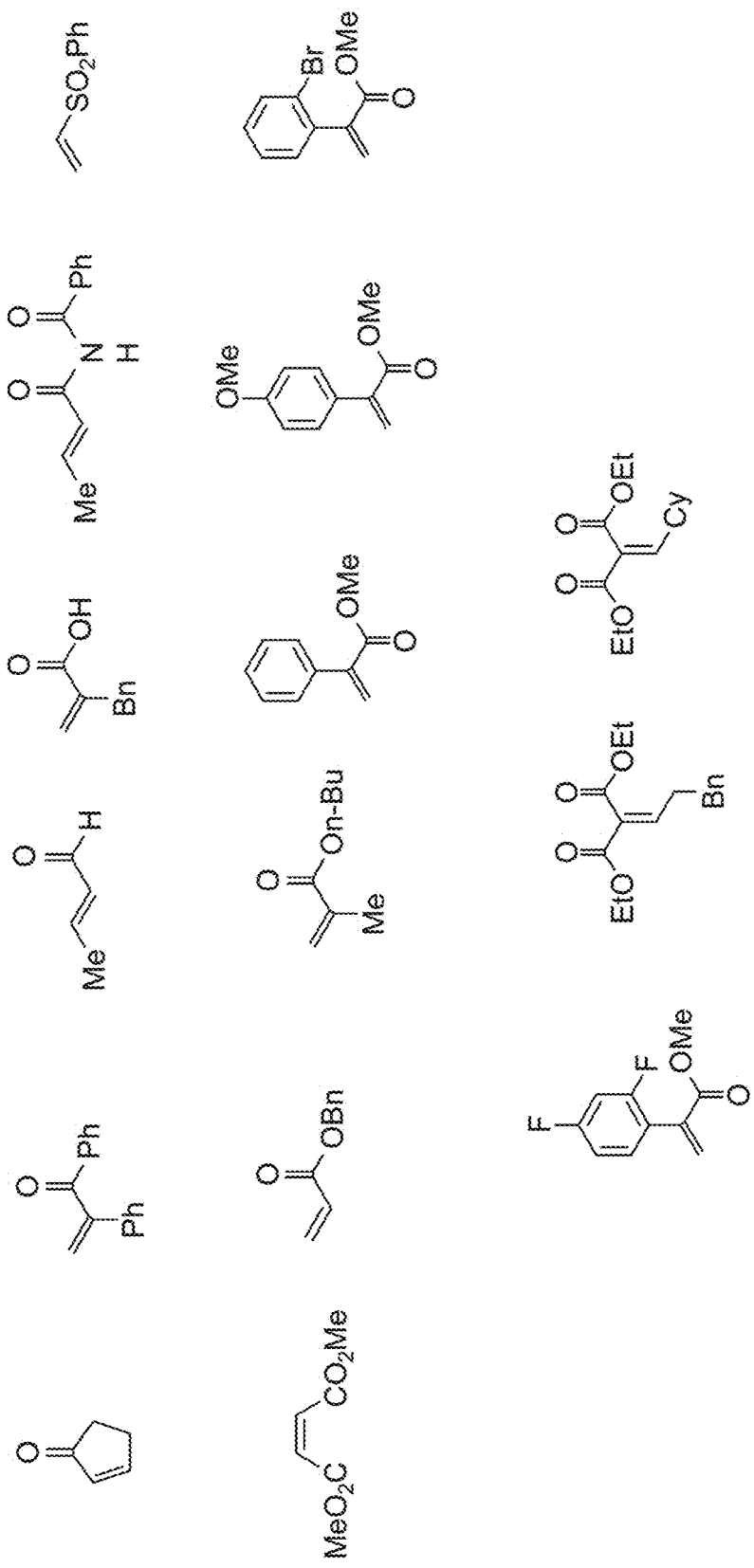
FIG. 1 illustrates various Michael acceptors according to some embodiments described herein.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

Definitions

The term "alkyl" as used herein, alone or in combination, refers to a straight or branched saturated hydrocarbon group. For example, an alkyl can be $C_1$-$C_{30}$.

The term "alkenyl" as used herein, alone or in combination, refers to a straight or branched chain hydrocarbon group having at least one carbon-carbon double bond.

The term "aryl" as used herein, alone or in combination, refers to an aromatic monocyclic or multicyclic ring system optionally substituted with one or more ring substituents The term "cycloalkyl" as used herein, alone or in combination, refers to a non-aromatic, saturated mono- or multicyclic ring system optionally substituted with one or more ring substituents.

The term "cycloalkenyl" as used herein, alone or in combination, refers to a non-aromatic, mono- or multicyclic ring system having at least one carbon-carbon double bond and is optionally substituted with one or more ring substituents.

The term "heterocycloalkyl" as used herein, alone or in combination, refers to a non-aromatic, saturated mono- or multicyclic ring system in which one or more of the atoms in the ring system is an element other than carbon, such as nitrogen, oxygen or sulfur, alone or in combination, and wherein the ring system is optionally substituted with one or more ring substituents.

The term "heterocycloalkenyl" as used herein, alone or in combination, refers to a non-aromatic, mono- or multicyclic ring system in which one or more of the atoms in the ring system is an element other than carbon, such as nitrogen, oxygen or sulfur, alone or in combination, and which contains at least one carbon-carbon double bond in the ring system and wherein the ring system is optionally substituted with one or more ring substituents.

The term "heteroalkyl" as used herein, alone or in combination, refers to an alkyl moiety as defined above, having one or more carbon atoms, for example one, two or three carbon atoms, replaced with one or more heteroatoms, which may be the same or different.

I. Decarboxylative Peptide Functionalization

Various methods of peptide functionalization via decarboxylative pathways are described herein. In one aspect, a method of peptide functionalization comprises providing a reaction mixture including a Michael acceptor and a peptide and coupling the Michael acceptor with the peptide via a mechanism including decarboxylation of a peptide reside. In some embodiments, the peptide C-terminal residue undergoes decarboxylative coupling with the Michael acceptor. Alternatively, an interior residue comprising a carboxyl side chain can undergo decarboxylative coupling with the Michael acceptor. As described further herein, the resulting coupling product can be a 1,4-addition adduct comprising the peptide and a Michael acceptor residue coupled to a decarboxylated amino acid residue of the peptide. Additionally, the reaction mixture can further comprise a base component.

A. Peptide

Turning now to specific components, the reaction mixture comprises a peptide. The peptide can have any desired number of amino acids not inconsistent with the objectives of the present invention. In some embodiments, for example, the peptide comprises a number of amino acids selected form Table I.

TABLE I

| Number of Amino Acids in Peptide |
|---|
| ≥3 |
| ≥5 |
| ≥7 |
| ≥10 |
| ≥15 |
| 3-300 |
| 5-500 |
| 10-400 |

As set forth in Table I, the peptide can comprise a sufficient number of amino acids to classify as a protein. In some embodiments, the peptide can comprise one or more β-amino acids in addition to α-amino acids. The peptide may also comprise unnatural amino acids and/or amino acid derivatives. In some embodiments, for example, the peptide can contain N-methyl amino acid(s) and/or amino acid derivatives comprising carboxyl side chains. Table II provides several non-limiting examples of unnatural amino acids and/or amino acid derivatives.

TABLE II

| Unnatural Amino Acids or Derivatives |
|---|
| γ-aminobutyric acid |
| 2-phenyl-γ-aminobutyric acid |
| 4-isobutyl-γ-aminobutyric acid |
| N-methyl amino acid |
| L-propargylglycine |
| 1-aminocyclopropane-1-carboxylic acid |
| 1-aminocyclopentane-1-carboxylic acid |
| 4-bromo-phenylalanine |

TABLE II-continued

Unnatural Amino Acids or Derivatives

N-α-Fmoc-N-ω,N-ω-bis-tert-butoxycarbonyl-
arginine
4-aminoheptanedioic acid
3-(1-aminocyclopropyl)propanoic acid
3-(1-aminocyclopentyl)propanoic acid The peptide can employ any amino acid or amino acid derivative operable to participate in decarboxylative pathways described herein. In some embodiments, the amino acid residue participating in the decarboxylative pathway is located at the C-terminus. For example, one or more of the amino acids listed in Table III may serve as the C-terminal residue of the peptide.

TABLE III

Alanine
Arginine
Asparagine
Aspartic Acid
Cysteine
Glutamic Acid
Glutamine
Glycine
Histidine
Isoleucine
Leucine
Lysine
Methionine
Phenylalanine
Proline
Serine
Threonine
Tryptophan
Tyrosine
Valine The carboxyl group of an amino acid residue participating in decarboxylative pathways described herein can be in protonated form, deprotonated form, carboxylate salt, carboxylate ester or other derivative form.

B. Michael Acceptor

As described herein, the reaction mixture also comprises a Michael acceptor. Michael acceptors operable for use in the present methods can exhibit a number of functional groups including esters, ketones, aldehydes, sulfones, imides, amides and carboxylic acids. For example, the Michael acceptor can be selected from cyclic or acyclic ketones, acyclic enals, α,β-unsaturated imides, sulfones, malonates, acrylates and maleates. In some embodiments, the Michael acceptor can generally be of formula (I):

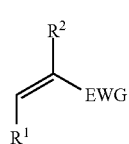

(I)

wherein EWG is an electron withdrawing group selected from the group consisting of -formyl, -keto, -ester, -cyano, -imide, -amide and -sulfone and $R^1$ and $R^2$ are independently selected from the group consisting of -hydrogen, -alkyl, -cycloalkyl, -aryl, -alkyl-aryl and -ester. FIG. 1 illustrates various Michael acceptors according to some embodiments described herein.

C. Catalyst

The reaction mixture can also include one or more catalytic species to assist in decarboxylative couplings described herein. Catalytic species, in some embodiments, participate in forming a carboxyl radical on a residue which then rapidly extrudes $CO_2$ to produce an amino radical. The amino radical is subsequently operable to undergo conjugate addition with the Michael acceptor to forge a new C—C bond. Catalyst can participate in carboxyl radical formation via a single electron transfer (SET) process. For example, catalyst can act in an oxidative capacity to produce the carboxyl radical followed by $CO_2$ extrusion, as illustrated in the non-limiting embodiment of FIG. 9. Alternatively, catalyst can act in reductive capacity to produce the carboxyl radical followed by $CO_2$ extrusion. Any catalyst operable to initiate a residue carboxyl radical followed by $CO_2$ extrusion is contemplated herein. In some embodiments, catalyst can also close the redox cycle by single electron transfer (SET) to the acyl radical formed by the conjugate addition, as illustrated in the non-limiting embodiment of FIG. 9. In some embodiments, the catalytic species initiating carboxyl radical formation can also close the redox cycle by SET. In other embodiments, different catalytic species or co-catalysts are used for carboxyl radical formation and acyl radical reduction.

Various transition metal catalysts may be operable to participate in the foregoing decarboxylative mechanisms and associated SET and/or redox processes. Nickel catalyst and/or noble metal catalyst, for example, may be suitable for use in coupling methods described herein. In some embodiments, catalyst is photoredox catalyst. Any photoredox catalyst operable to participate in in decarboxylative mechanisms described herein can be used in the reaction mixture. For example, photoredox catalyst can include one or more iridium and/or ruthenium complexes. In some embodiments, heteroleptic iridium complexes are selected as the photocatalyst. Suitable heteroleptic iridium complexes can include $Ir[dF(CF_3)ppy]_2(dtbbpy)^+$, $Ir(dF(CF_3)ppy)_2(4,4'$-dcbpy) and $Ir(ppy)_2(dtbbpy)^+$. Homoleptic iridium complexes, such as $Ir(dFppy)_3$, can also be used as photocatalyst.

In other embodiments, photoredox catalyst can comprise one or more organic species including, but not limited to, riboflavin derivatives. For example, riboflavin tetrabutyrate or riboflavin tetra-N-ethylcarbamate may be employed as photoredox catalyst.

Photoredox catalyst can be present in the reaction mixture in any amount not inconsistent with the objectives of the present invention. In some embodiments, photoredox catalyst is present in the reaction mixture in an amount selected from Table IV.

TABLE IV

| Photoredox Catalyst in Reaction Mixture mol. % |
|---|
| 0.1-60 |
| 0.1-30 |
| 0.1-15 |
| 0.1-5 |
| 0.5-3 |
| 0.5-2 |

In further embodiments, one or more electrochemical methods may be used to initiate carboxyl radical formation and/or acyl radical reduction. For example, one or more electrodes can be positioned in the reaction mixture to initiate decarboxylative mechanisms and associated SET and/or redox processes described herein. Additionally, one or more reducing metals such as zinc may be used to initiate carboxyl radical formation and/or acyl radical reduction.

D. Base and Solvent Components

In some embodiments, the reaction mixture further comprises base. Any base not inconsistent with the objectives of the present invention can be used, including inorganic bases. In some embodiments, suitable inorganic base is selected from Table V.

TABLE V

Base of the Reaction Mixture

CsF
$Cs_2CO_3$
CsOAc
$K_2CO_3$
$K_2HPO_4$
$Bi(OTf)_3$
$Sc(OAc)_3$

Components of the reaction mixture are disposed in a solvent. Any solvent not inconsistent with the objectives of the present invention can be employed. The solvent, for example, can be an aprotic polar solvent. In some embodiments, the solvent is selected from Table VI.

TABLE VI

Solvent of the Reaction Mixture

DMSO
DMPU
DMF
DMA
NMP
$CH_3CN$

In one embodiment, for example, solvent of the reaction mixture is DMF at a molarity of 0.01 to 0.1M. In other embodiments, suitable solvent can be water or aqueous-based solvent systems. Buffer solutions, for example, can be employed in reaction mixtures described herein. In some embodiments, pyridinium formate is a suitable buffer solution.

For coupling methods employing photocatalyst, the reaction mixture is irradiated with a radiation source resulting in coupling of the Michael acceptor with the peptide via a mechanism including decarboxylation of an amino acid residue. The amino acid residue can be an internal residue or the peptide C-terminal residue. Advantageously, irradiation and the subsequent reaction can take place at room temperature. Radiation of any wavelength suitable for photocatalyst activation may be employed. In some embodiments, the radiation source provides radiation in the visible region of the electromagnetic spectrum. In some embodiments, the radiation source comprises one or more one compact fluorescent lamps (CFL), light emitting diodes (LED) or combinations thereof. For example, blue LEDs may be used as the radiation source. While visible light is employed in the examples described herein, radiation of other region(s) of the electromagnetic spectrum are contemplated, including ultraviolet and/or infrared radiation. In some embodiments, the reaction is allowed proceed for a time period of 1 to 48 hours.

Figure 2:
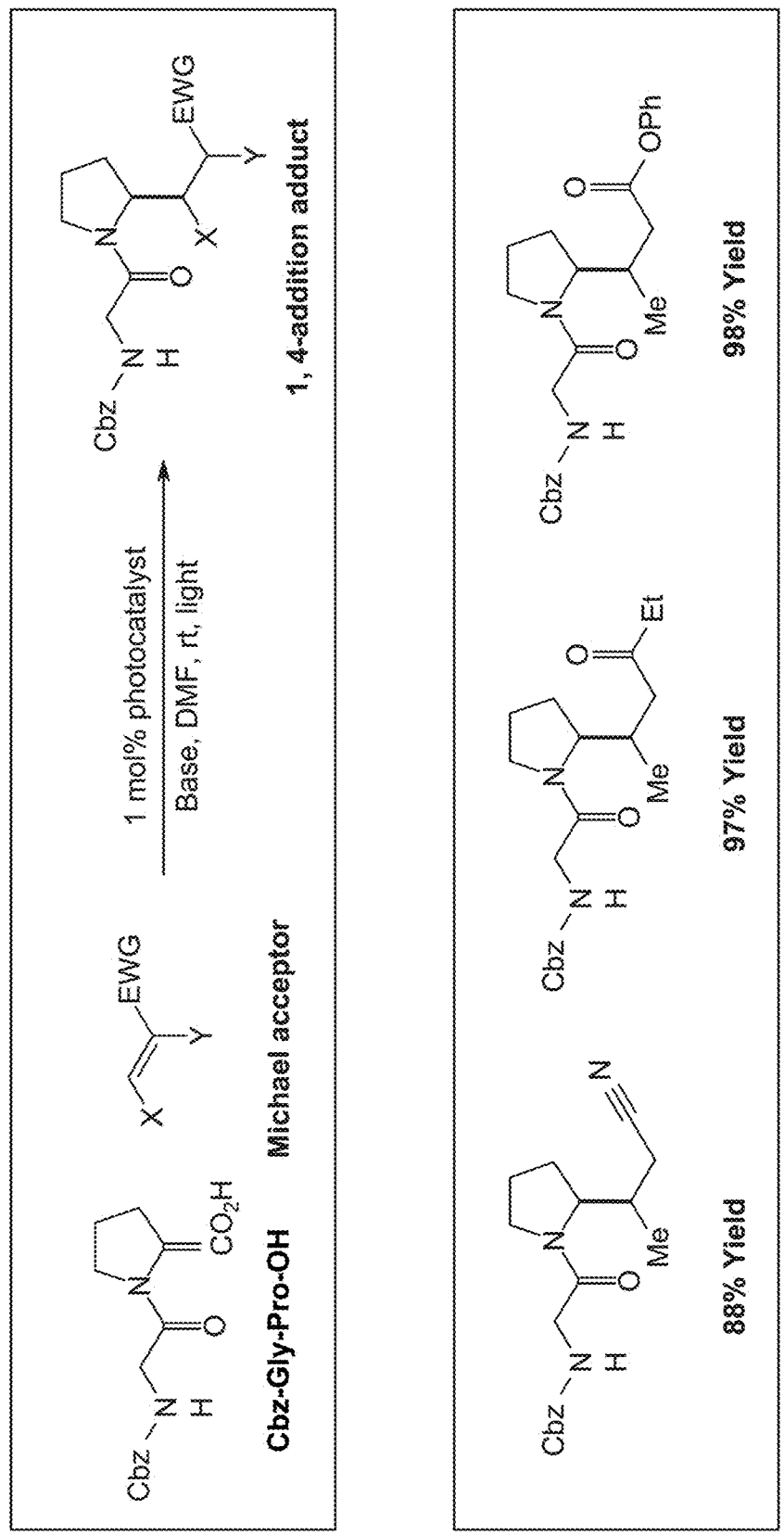
FIG. 2 illustrates peptide functionalization at the C-terminal residue according to some embodiments described herein.
Figure 3:
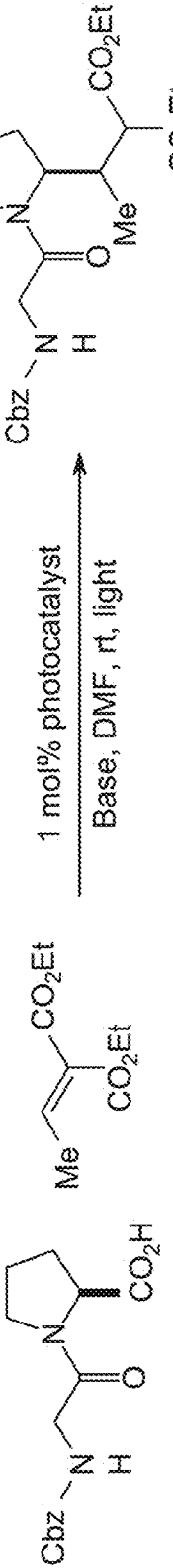
FIG. 3 illustrates peptide functionalization at the C-terminal residue according to some embodiments described herein. Figure discloses SEQ ID NOS 38-41, respectively, in order of appearance.
Figure 4:
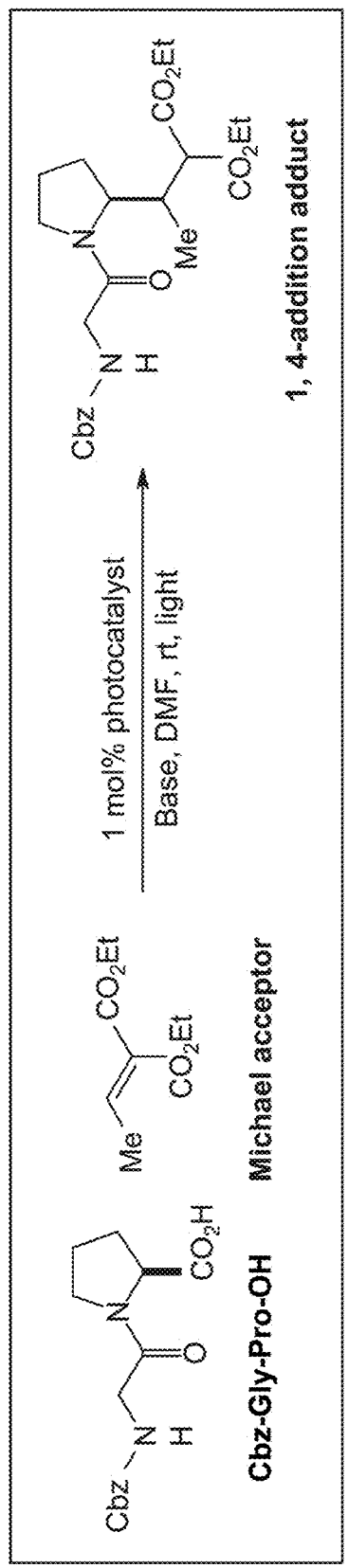
FIG. 4 illustrates peptide functionalization at the C-terminal residue according to some embodiments described herein. Figure discloses SEQ ID NOS 42-43, 1, and 44-45, respectively, in order of appearance.
Figure 5A:
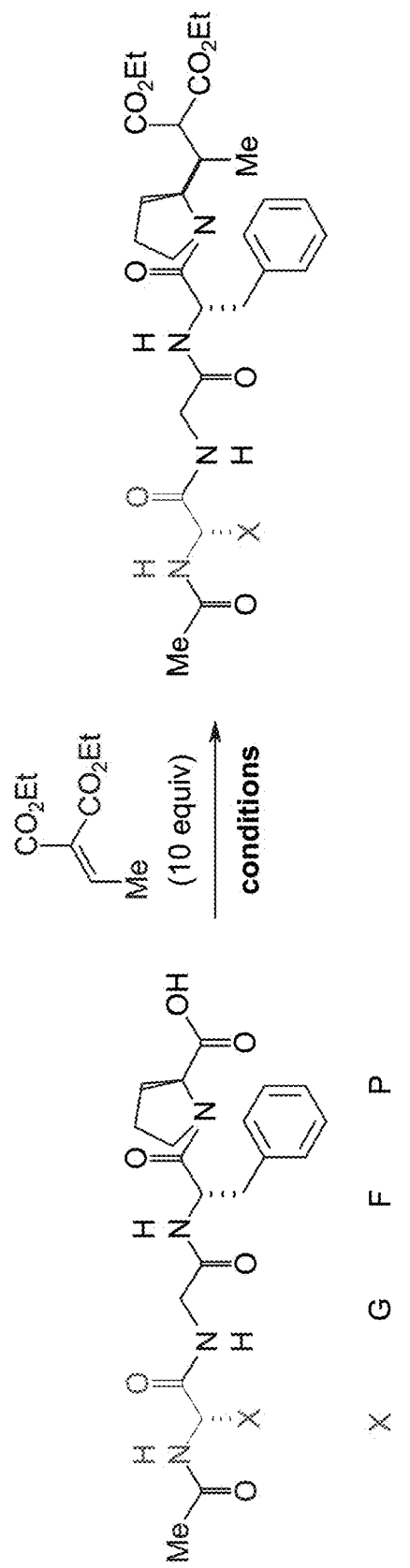
FIGS. 5A-5E illustrate examples of C-terminus peptide functionalization under various reaction conditions according to some embodiments described herein.
Figure 5B:
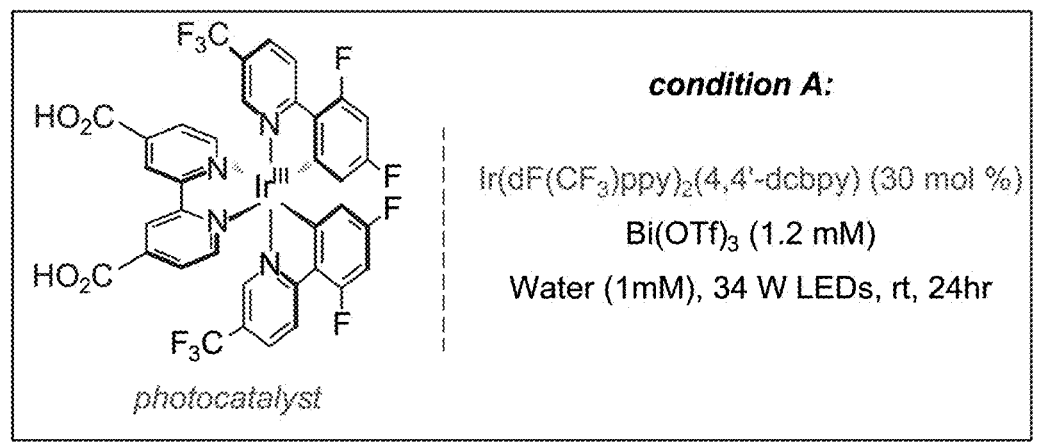
Figure 5B:
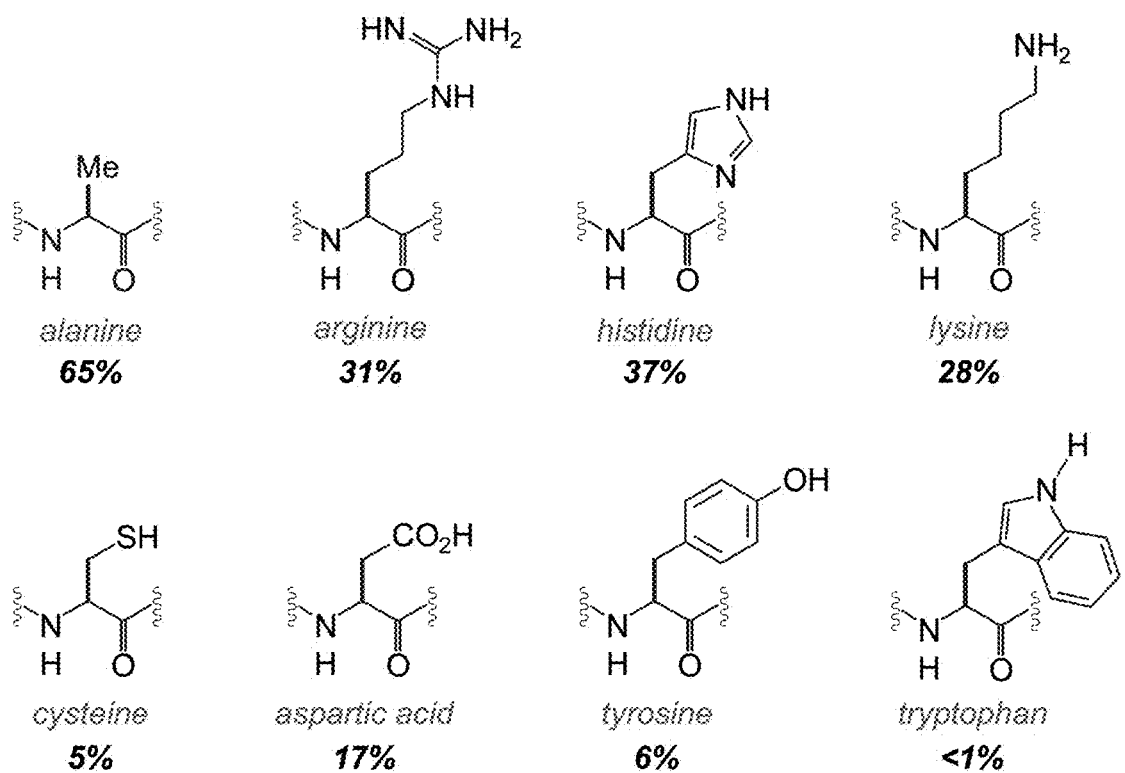
Figure 5C:
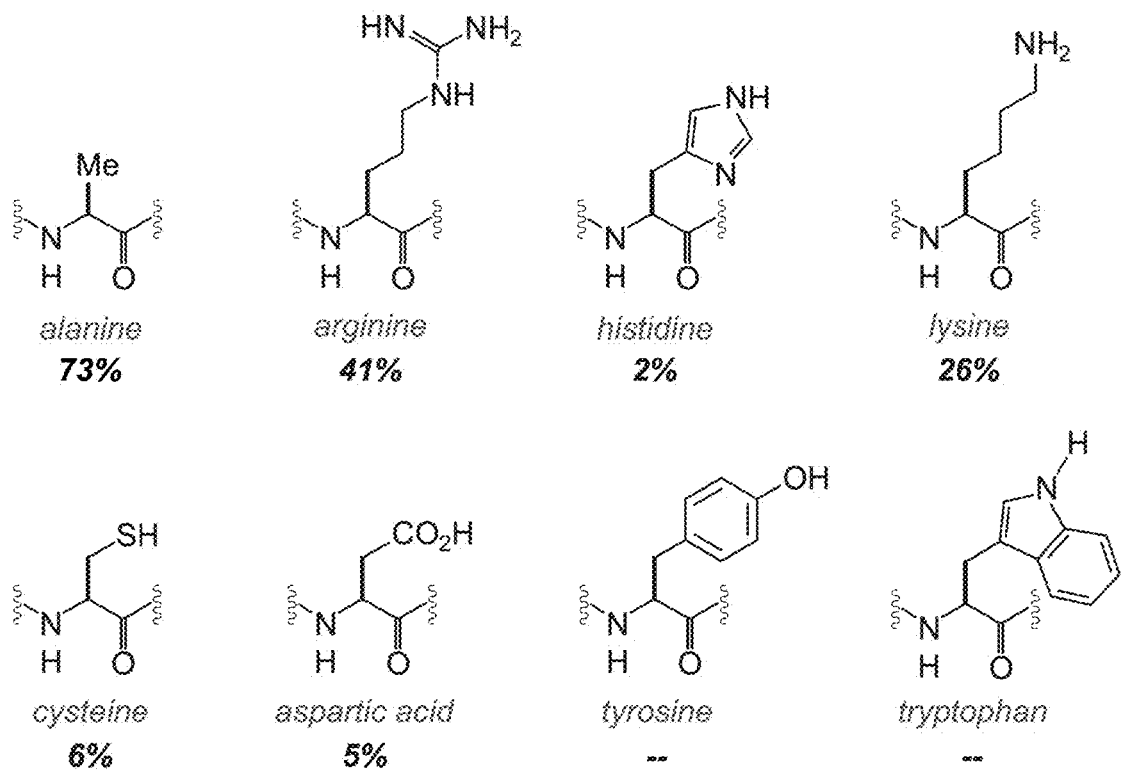
Figure 5D:
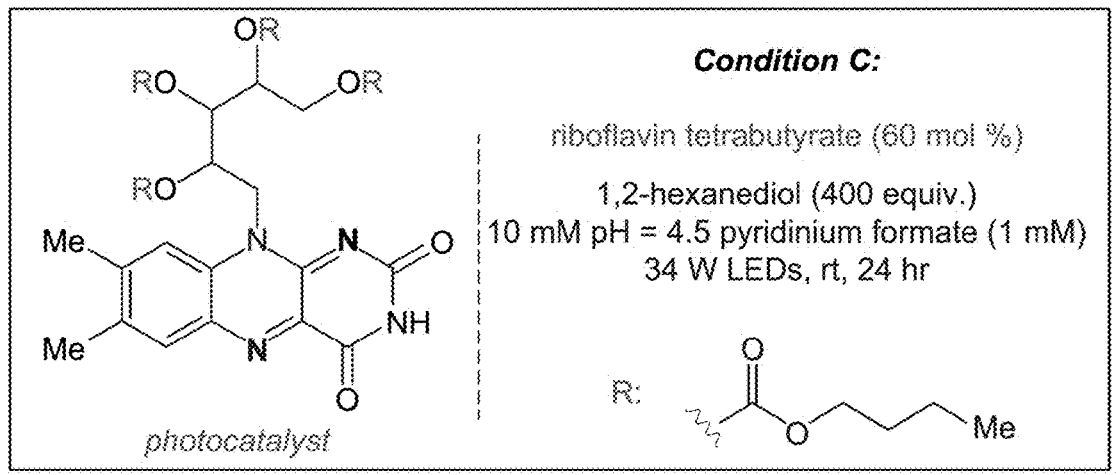
Figure 5D:
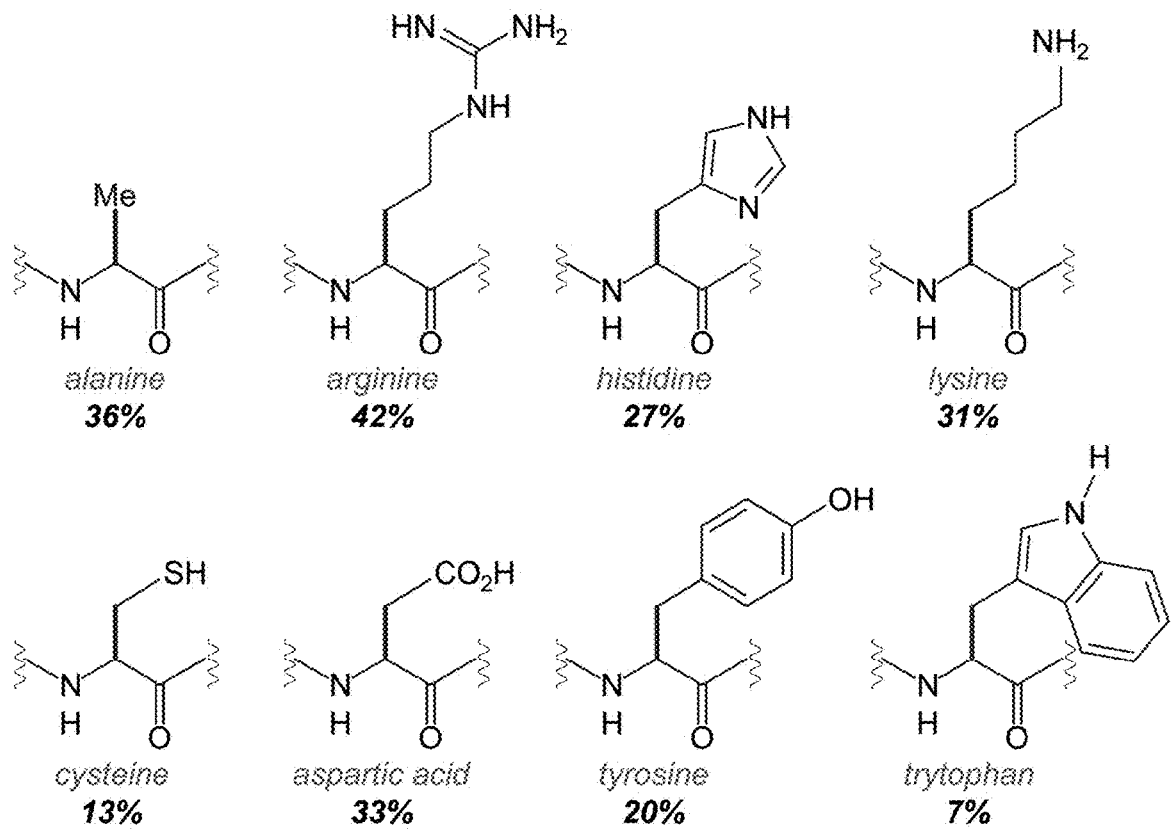
Figure 5E:
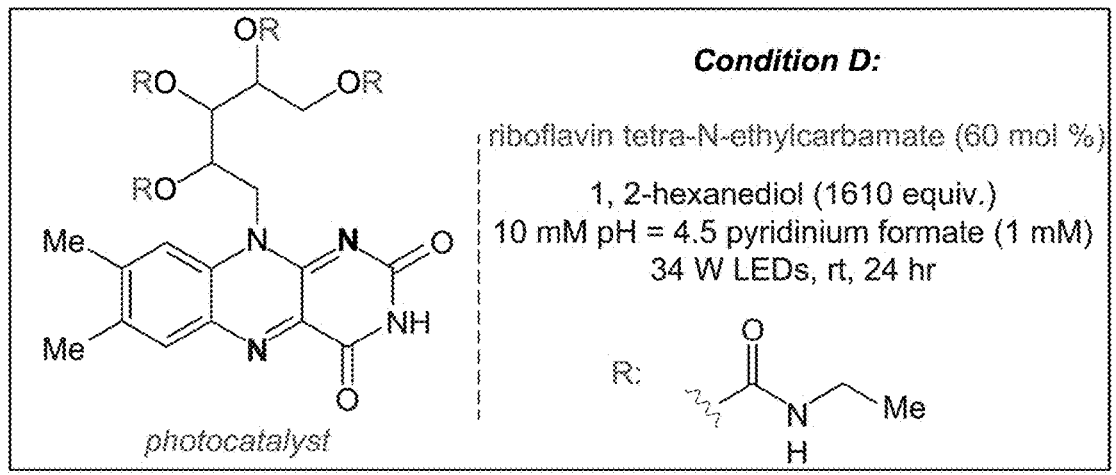
Figure 5E:
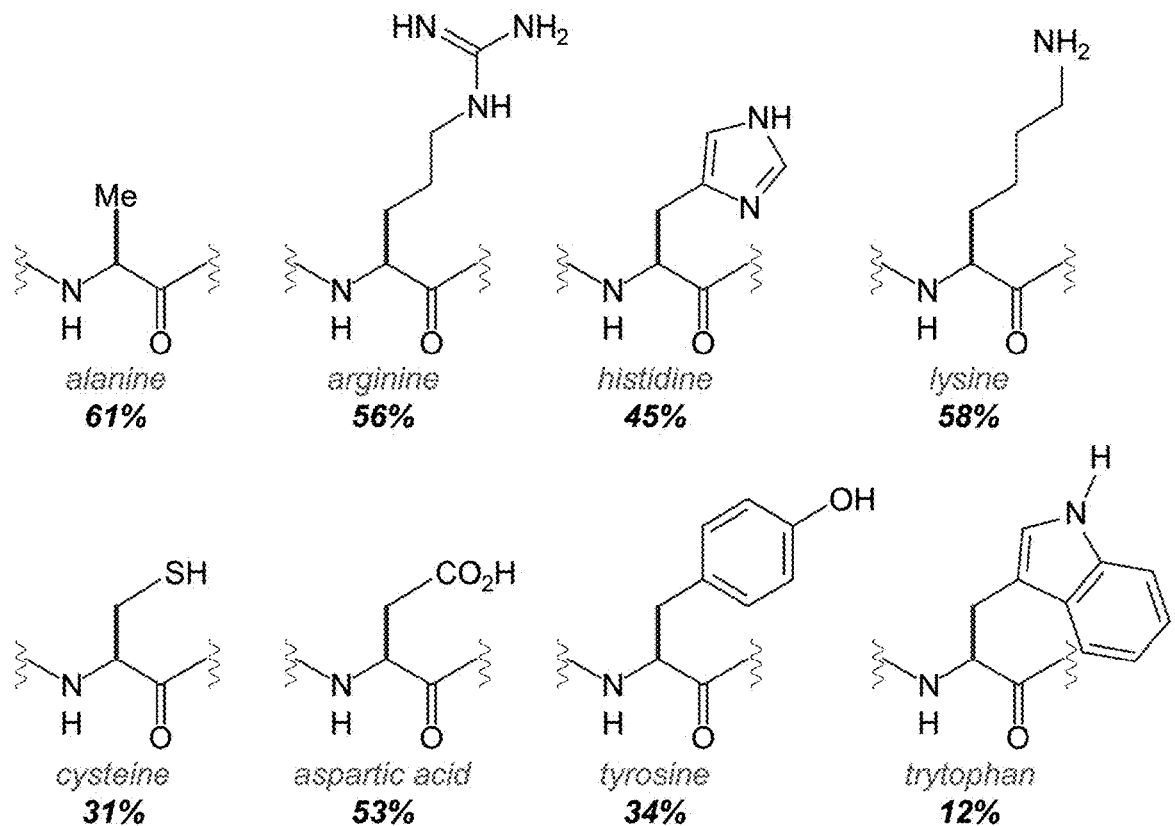

FIGS. 2-4 illustrate specific examples of peptide functionalization according to methods described herein. As illustrated in FIGS. 2-4, the resulting coupling product is a 1,4-addition adduct comprising the peptide and a Michael acceptor residue coupled to the decarboxylated C-terminal residue of the peptide. General protocol for the reactions depicted in FIGS. 2-4 is provided in the examples section below.

FIGS. 5A-5E also illustrate examples of C-terminus peptide functionalization under various reaction conditions according to some embodiments described herein. General reaction conditions are provided in FIG. 5A wherein a tetramer of X-glycine-phenylalanine-proline is provided. The N-terminal residue (X) was varied as illustrated in FIGS. 5B-5E to determine effect on yield of C-terminal functionalized peptide. Specific reaction conditions were also varied (conditions A-D) as provided in FIGS. 5B-5E respectively. As detailed in FIGS. 5A-5E, peptide functionalization via decarboxylative pathways occurs in good yield over a variety of substrates and reaction conditions with transition metal catalyst and organic catalyst.

Figure 6A:
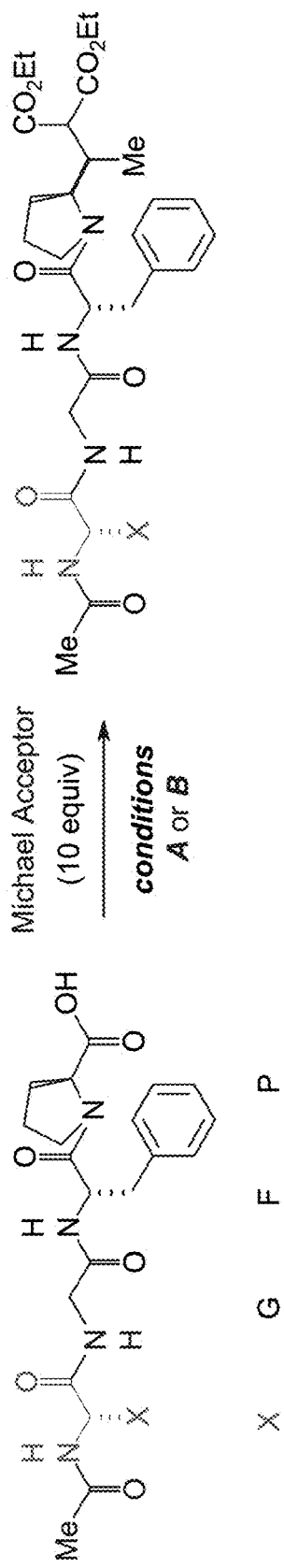
FIGS. 6A-6C illustrate various Michael acceptors for peptide functionalization at the C-terminus under differing catalyst conditions according to some embodiments described herein.
Figure 6A:
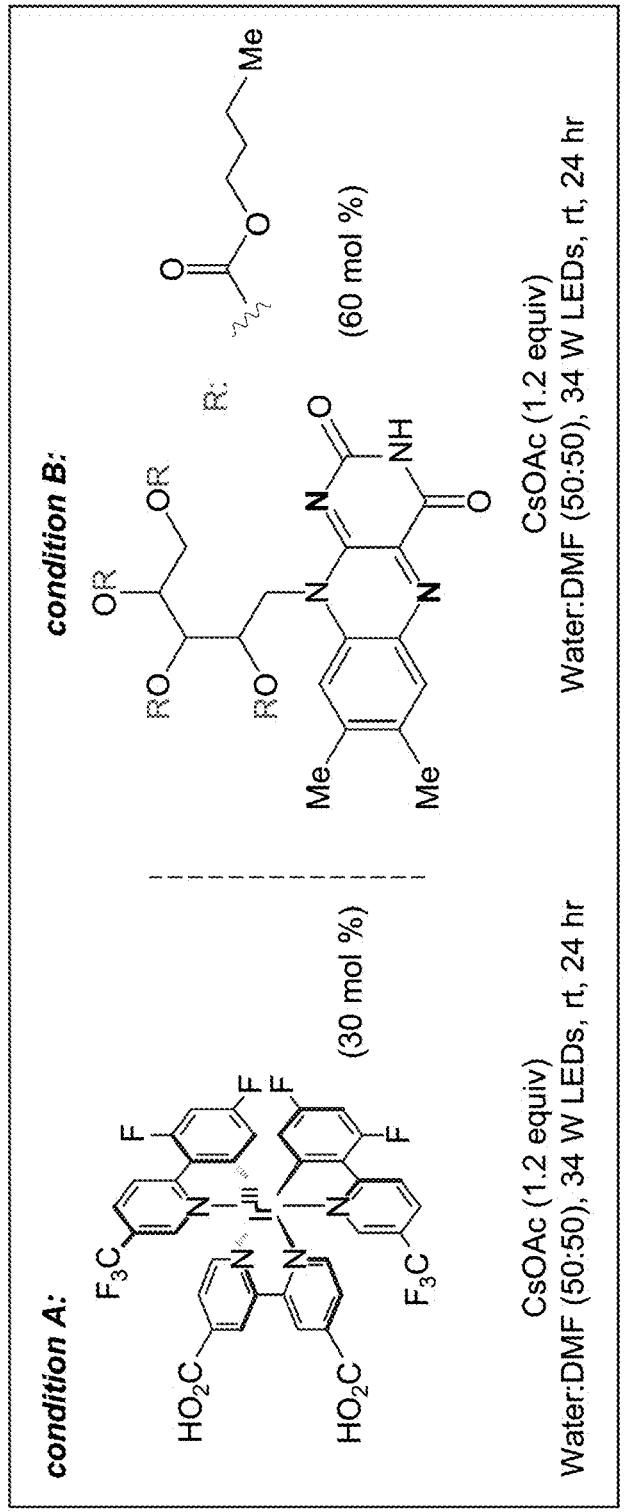
Figure 6B:
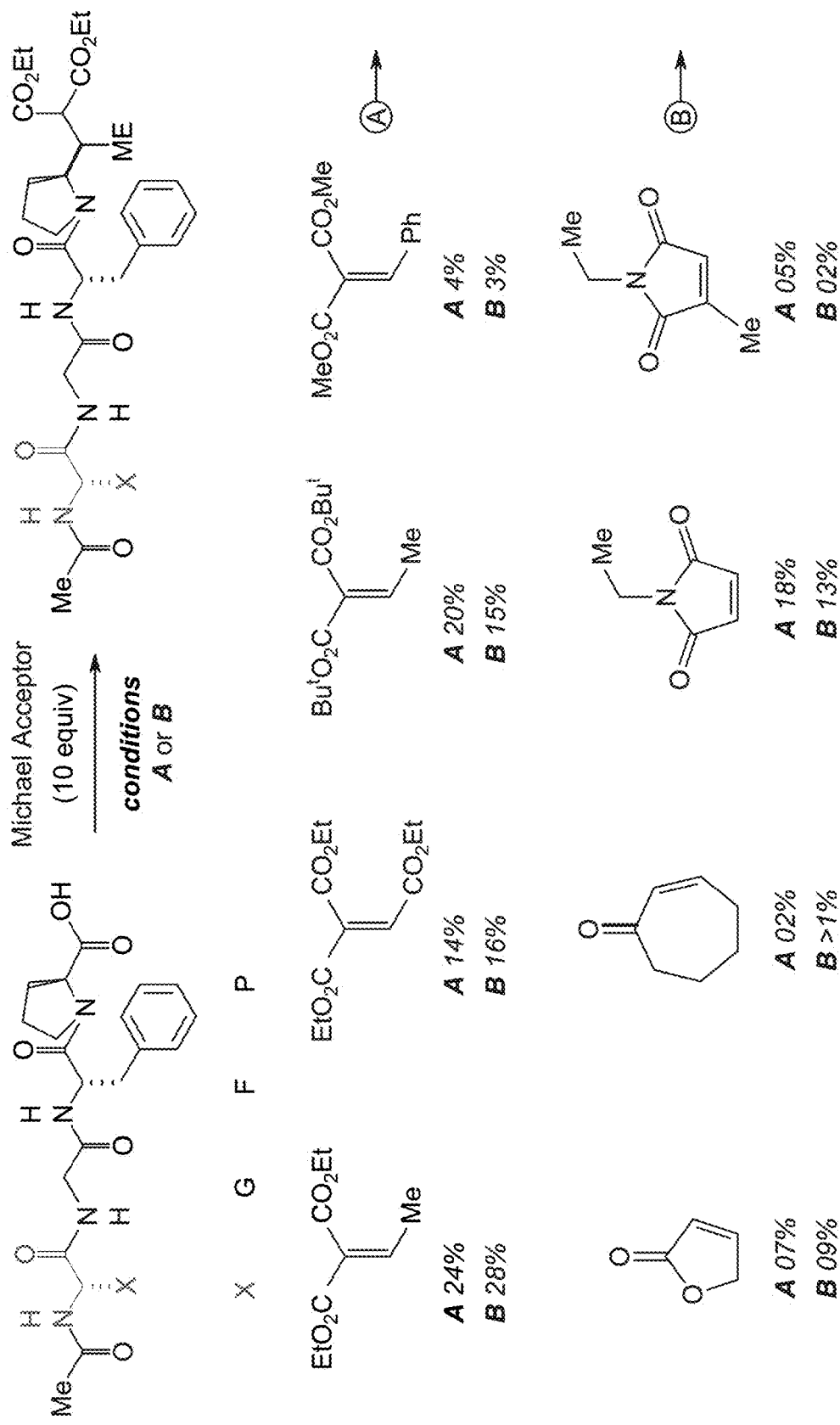
Figure 6B:
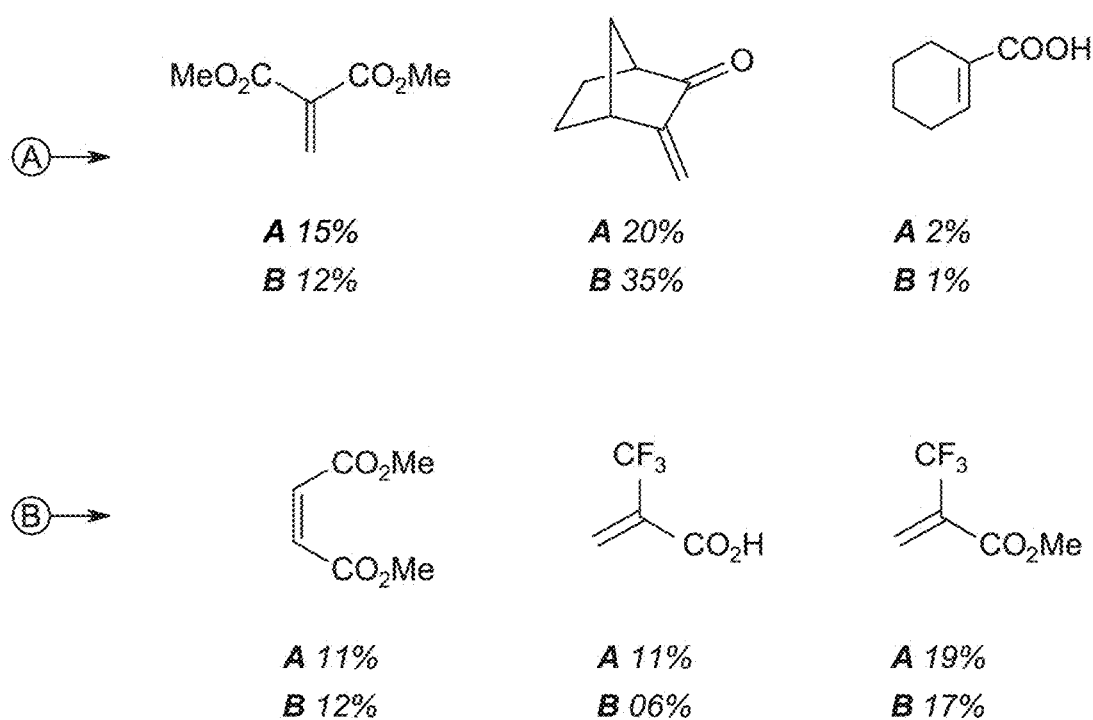
Figure 6C:
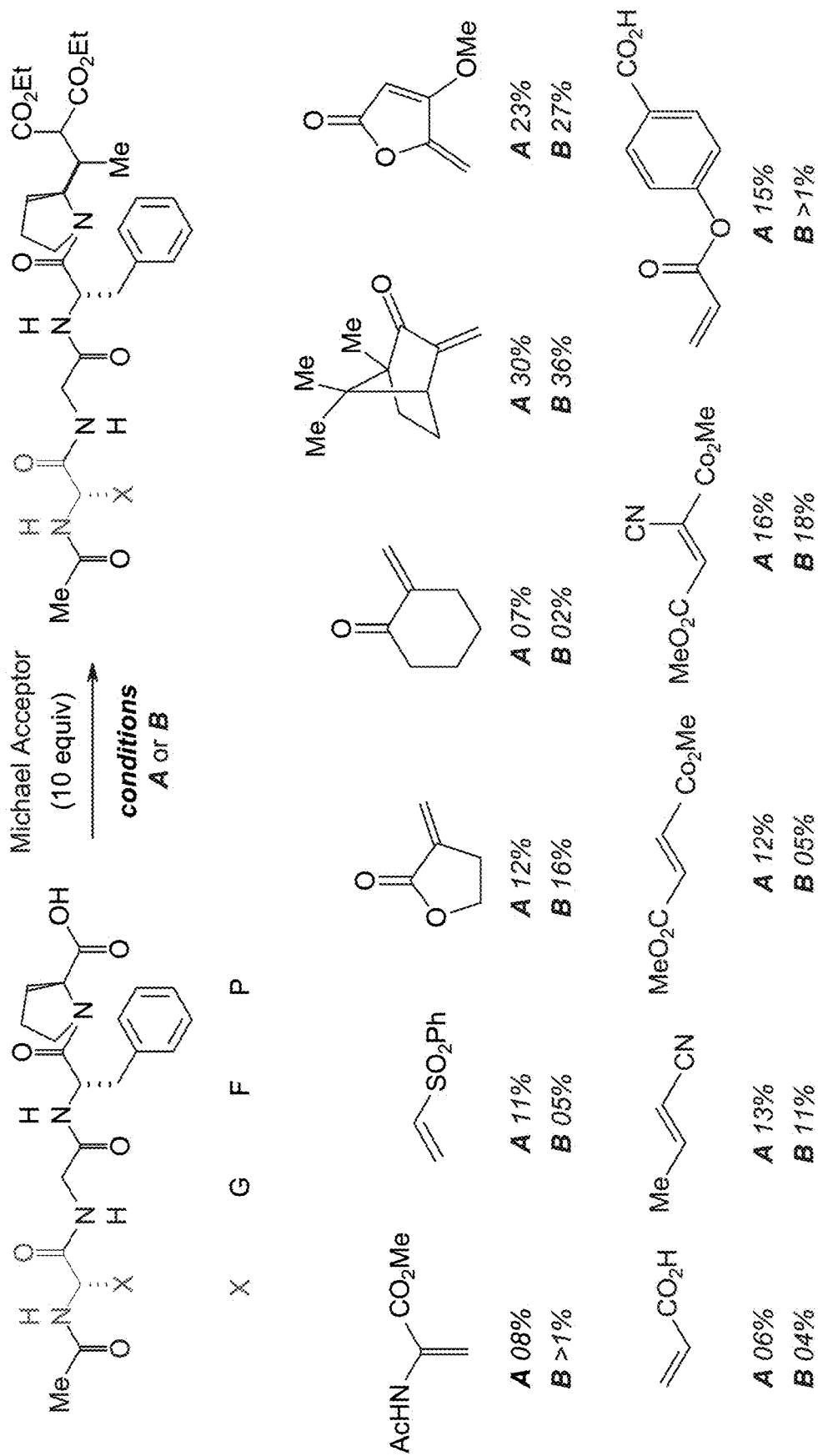

FIGS. 6A-6C illustrate various Michael acceptors for peptide functionalization at the C-terminus under differing catalyst conditions according to some embodiments described herein. As provided in FIG. 6A, iridium photocatalyst is employed in condition A and riboflavin tetrabutyrate photocatalyst is provided in condition B. A variety of Michael acceptors were compatible with decarboxylative mechanisms described herein resulting in C-terminal functionalization.

Figure 7A:
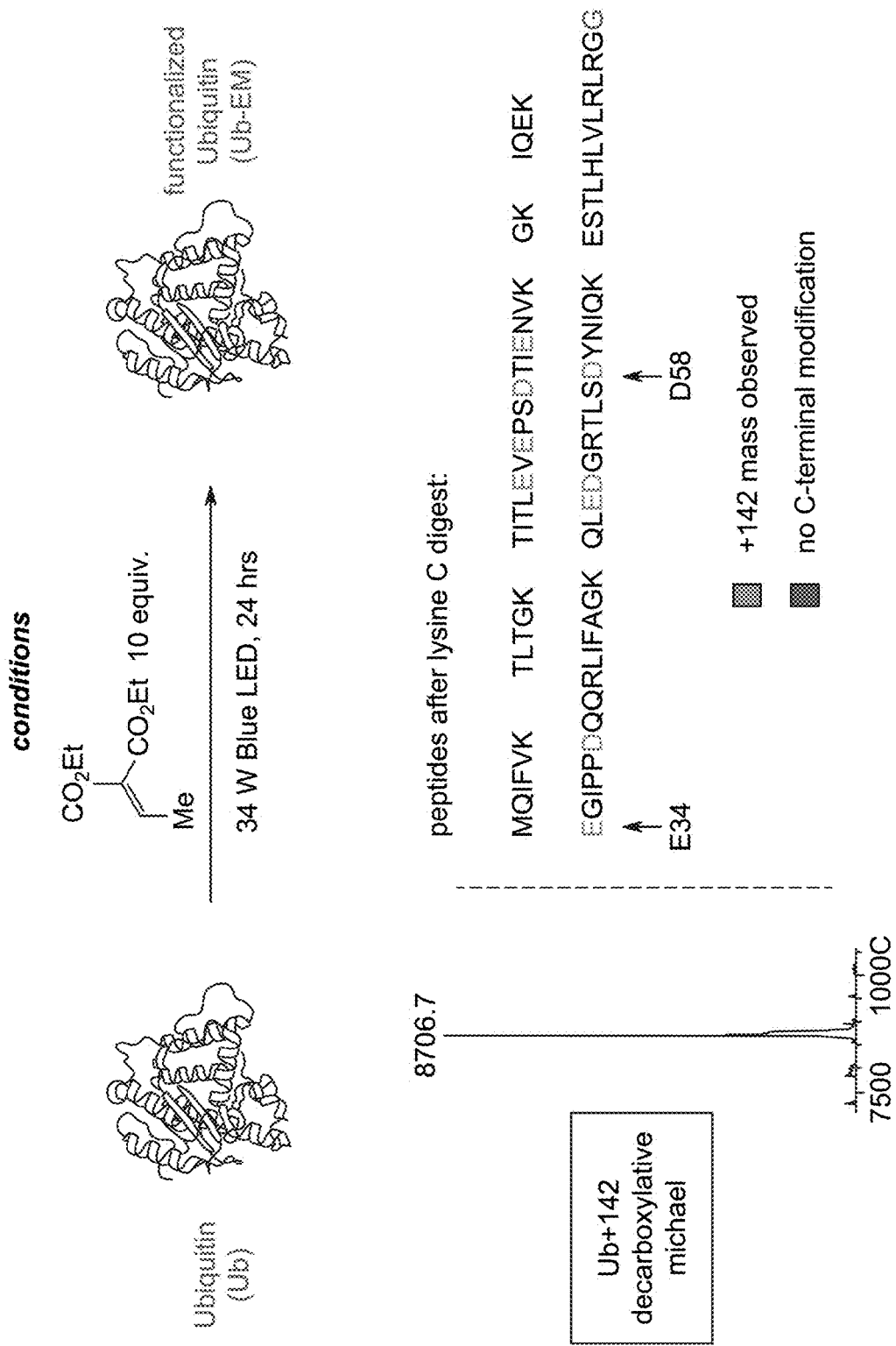
FIGS. 7A-7C illustrate peptide functionalization at interior locations via decarboxylative mechanisms described herein.
Figure 7B:
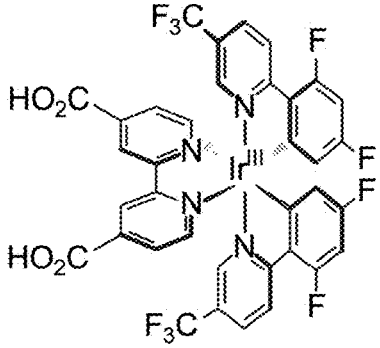
Figure 7C:
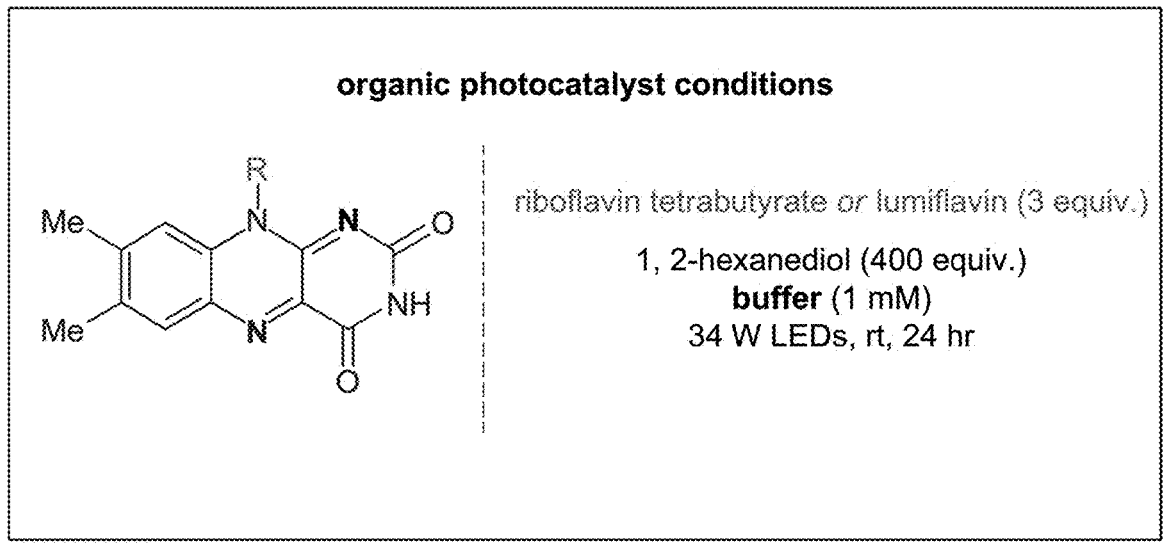

In further embodiments, interior residues having carboxyl moieties can undergo functionalization with Michael acceptors via decarboxylative mechanisms described herein. Interior aspartic acid and/or glutamic acid residues, for example, can participate in peptide functionalization described herein. Moreover, unnatural amino acids or amino acid derivatives having carboxyl functionality can be located at interior positions of the peptide chain. Such amino acids and derivatives may also participate in peptide functionalization. FIGS. 7A-7C illustrate peptide functionalization at interior locations via decarboxylative mechanisms described herein. As provided in FIG. 7A, Ubiquitin is added to a reaction mixture with Michael acceptor and photocatalyst for decarboxylative functionalization. Shorter peptide sequences or segments of Ubiquitin are also shown in FIG. 7 as part of analytical characterization of functionalized peptide. FIGS. 7B and 7C summarize interior amino acid functionalization with respect to iridium and riboflavin tetrabutyrate photocatalyst. As illustrated in FIGS. 7B and 7C, Ubiquitin was functionalized with Michael acceptor at various acidic residue interior locations.

II. Decarboxylative Peptide Coupling

In another aspect, methods of peptide coupling are described herein. A method of peptide coupling comprises providing a reaction mixture including a first peptide and a second peptide, the second peptide comprising a Michael acceptor functionalized N-terminal residue and coupling the functionalized N-terminal residue with the first peptide via a mechanism including decarboxylation of an amino acid residue of the first peptide. In some embodiments, the first peptide C-terminal residue undergoes decarboxylative coupling with the Michael acceptor functionalized N-terminal residue of the second peptide. In other embodiments, an interior amino acid residue of the first peptide undergoes decarboxylative coupling with the Michael acceptor functionalized N-terminal residue of the second peptide.

The first peptide and the second peptide can each have any desired number of amino acids not inconsistent with the objectives of the present invention. In some embodiments, each of the first and second peptides has a number of amino acids selected from Table I herein. The peptide can also include unnatural amino acids and/or amino acid derivatives. For example, the peptide can include unnatural amino acids or derivatives of Table II herein. Further, various Michael acceptors can be employed to functionalize the N-terminal residue. For example, in some embodiments, crotonic acid or crotonic acid derivative can be reacted with the terminal amine to provide a Michael acceptor functionalized N-terminus.

The reaction mixture can also include one or more catalytic species to assist in the decarboxylative coupling of the first and second peptides. Catalytic species, in some embodiments, participate in forming a carboxyl radical on a residue of the first peptide which then rapidly extrudes $CO_2$ to produce an amino radical. The amino radical is subsequently operable to undergo conjugate addition with the N-terminal pendant Michael acceptor of the second peptide to forge a new C—C bond resulting in peptide coupling. Catalyst can participate in carboxyl radical formation via a single electron transfer (SET) process. For example, catalyst can act in an oxidative capacity to produce the carboxyl radical followed by $CO_2$ extrusion. Alternatively, catalyst can act in reductive capacity to produce the carboxyl radical followed by $CO_2$ extrusion. Any catalyst operable to initiate a carboxyl radical of the C-terminus residue or an interior acid residue followed by $CO_2$ extrusion is contemplated herein. In some embodiments, catalyst can also close the redox cycle by single electron transfer (SET) to the α-acyl radical formed by the conjugate addition. In other embodiments, different catalytic species or co-catalysts are used for carboxyl radical formation and acyl radical reduction.

Various transition metal catalysts may be operable to participate in the foregoing decarboxylative mechanisms and associated SET and/or redox processes. Nickel catalyst and/or noble metal catalyst, for example, may be suitable for use in coupling methods described herein. In some embodiments, catalyst is photoredox catalyst. Any photoredox catalyst operable to participate in in decarboxylative mechanisms described herein can be used in the reaction mixture. For example, photoredox catalyst can include one or more iridium complexes. In some embodiments, heteroleptic iridium and/or ruthenium complexes are selected as the photocatalyst. Suitable heteroleptic iridium complexes include $Ir[dF(CF_3)ppy]_2(dtbbpy)^+$, $Ir(dF(CF_3)ppy)_2(4,4'\text{-}dcbpy)$ and $Ir(ppy)_2(dtbbpy)^+$. Homoleptic iridium complexes, such as $Ir(dFppy)_3$, can also be used as photocatalyst. Moreover, photoredox catalyst may be present in the reaction mixture in an amount selected from Table IV herein.

In further embodiments, one or more electrochemical methods may be used to initiate carboxyl radical formation and/or acyl radical reduction. For example, one or more electrodes can be positioned in the reaction mixture to initiate decarboxylative mechanisms and associated SET and/or redox processes described herein. Additionally, one or more reducing metals, such as zinc, may be used to initiate carboxyl radical formation and/or acyl radical reduction.

Figure 8:
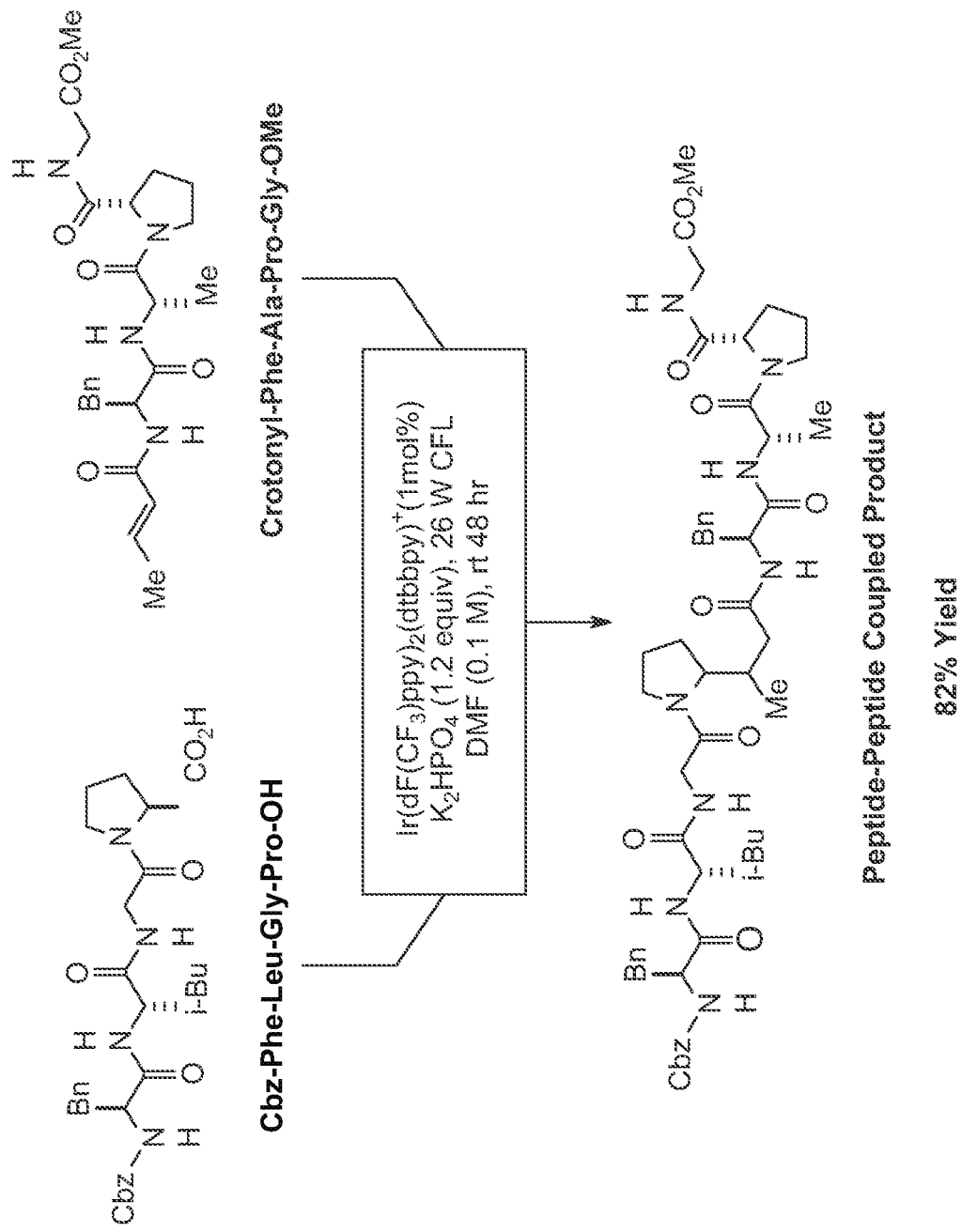
FIG. 8 illustrates an example of peptide coupling according to one embodiment of a method described herein. Figure discloses SEQ ID NOS 2-3, respectively, in order of appearance.

Moreover, base and solvent components described in Section I above can complete the reaction mixture. FIG. 8 illustrates a non-limiting example of peptide coupling according to one embodiment of a method described herein. General protocol for administering the peptide coupling of FIG. 8 is provided in the examples section below.

III. Decarboxylative Peptide Intramolecular Cyclization

In a further aspect, methods of intramolecular peptide cyclization are described herein. For example, a method of intramolecular peptide cyclization comprises providing a reaction mixture comprising a peptide including a C-terminal residue and a Michael acceptor functionalized N-terminal residue and coupling the C-terminal residue with the functionalized N-terminal residue via a mechanism including decarboxylation of the C-terminal residue. Coupling of the functionalized N-terminal residue with the C-terminal residue results in cyclization of the peptide.

The peptide can have any desired number of amino acids commensurate with intramolecular cyclization according to mechanistic pathways described herein. In some embodiments, the peptide has at least three amino acids. In some embodiments, the peptide has a number of amino acids selected from Table I herein. The peptide can also include unnatural amino acids and/or amino acid derivatives. For example, the peptide can include unnatural amino acids or derivatives of Table II herein. Further, the Michael acceptor functionalized N-terminal residue can have structure as described in Section II above.

As provided in the specific examples below, peptide substrates containing oxidation-sensitive functionality, such as thioethers and indoles present in the side chains of Met and Trp, can be readily cyclized under redox conditions described herein. In addition protected amines, amides, and guanidiniums (Lys, Gln, and Arg) can be incorporated into cyclic peptide products. Linear sequences containing the non-natural amino acids N-methyl alanine and propargyl glycine undergo photoredox macrocyclization with exceptional efficiency. Heteroaromatic side chains are also tolerated, with a substrate containing protected His undergoing cyclization in 65% yield. Intriguingly, a substrate containing a C-terminal Glu residue shows complete selectivity for decarboxylation at the terminal carboxylic acid over reaction on the side chain. This result can be rationalized by the oxidation potential difference between carboxyl functionality adjacent to radical stabilizing heteroatoms and primary alkyl carboxylic acids. In addition to tolerating a variety of functionalized side chains, methods described herein are also amenable to substitution at the terminal amino acid and Michael acceptor portions of the precursor linear sequences. Incorporating a radical-stabilizing phenyl group at the α-position of the Michael acceptor results in excellent reaction efficiency and good levels of diastereoselectivity. The use of substituted amino acid N-methyl leucine at the C-terminus also results in a highly efficient macrocyclization reaction. Furthermore, bicyclic spiro products can be readily generated through the use of fully substituted carboxylic acids.

The reaction mixture can include one or more catalytic species to assist in decarboxylative intramolecular cyclization of the peptide. Catalytic species, in some embodiments, participate in forming a carboxyl radical on a residue which then rapidly extrudes $CO_2$ to produce an amino radical. The amino radical is subsequently operable to undergo conjugate addition with the N-terminal pendant Michael acceptor to forge a new C—C bond resulting in an α-acyl radical and intramolecular peptide cyclization. Catalyst can participate in carboxyl radical formation via a single electron transfer (SET) process. For example, catalyst can act in an oxidative capacity to produce the carboxyl radical followed by $CO_2$ extrusion. Alternatively, catalyst can act in reductive capacity to produce the carboxyl radical followed by $CO_2$ extrusion. Any catalyst operable to initiate a carboxyl radical of the C-terminus residue followed by $CO_2$ extrusion is contemplated herein. In some embodiments, catalytic species initiating carboxyl radical formation can also close the redox cycle by single electron transfer (SET) to the α-acyl radical formed by the conjugate addition. In other embodiments, different catalytic species or co-catalysts are used for carboxyl radical formation and acyl radical reduction.

Various transition metal catalysts may be operable to participate in the foregoing decarboxylative mechanisms and associated SET and/or redox processes. Nickel catalyst and/or noble metal catalyst, for example, may be suitable for use in coupling methods described herein. In some embodiments, catalyst is photoredox catalyst. Any photoredox catalyst operable to participate in in decarboxylative mechanisms described herein can be used in the reaction mixture. For example, photoredox catalyst can include one or more iridium and/or ruthenium complexes. In some embodiments, heteroleptic iridium complexes are selected as the photocatalyst. Suitable heteroleptic iridium complexes include Ir[dF(CF$_3$)ppy]$_2$(dtbbpy)$^+$, Ir(dF(CF$_3$)ppy)$_2$(4,4'-dcbpy) and Ir(ppy)$_2$(dtbbpy)$^+$. Homoleptic iridium complexes, such as Ir(dFppy)$_3$, can also be used as photocatalyst. Moreover, photoredox catalyst may be present in the reaction mixture in an amount selected from Table IV herein. In some embodiments for example, photoredox catalyst is present in the reaction mixture in an amount of 5-15 mol % or 8-12 mol %.

In further embodiments, one or more electrochemical methods may be used to initiate carboxyl radical formation and/or acyl radical reduction. For example, one or more electrodes can be positioned in the reaction mixture to initiate decarboxylative mechanisms and associated SET and/or redox processes described herein. Additionally, one or more reducing metals, such as zinc, may be used to initiate carboxyl radical formation and/or acyl radical reduction.

The reaction mixture can further comprise co-catalyst operable to participate in hydrogen atom transfer (HAT) to carbon centered radicals, such as those encountered in decarboxylative intramolecular peptide cyclization pathways described herein. Suitable co-catalyst can include various aryl thiol compounds.

Base and solvent components described in Section I above can complete the reaction mixture for of peptide intramolecular cyclization via decarboxylation.

Figure 9:
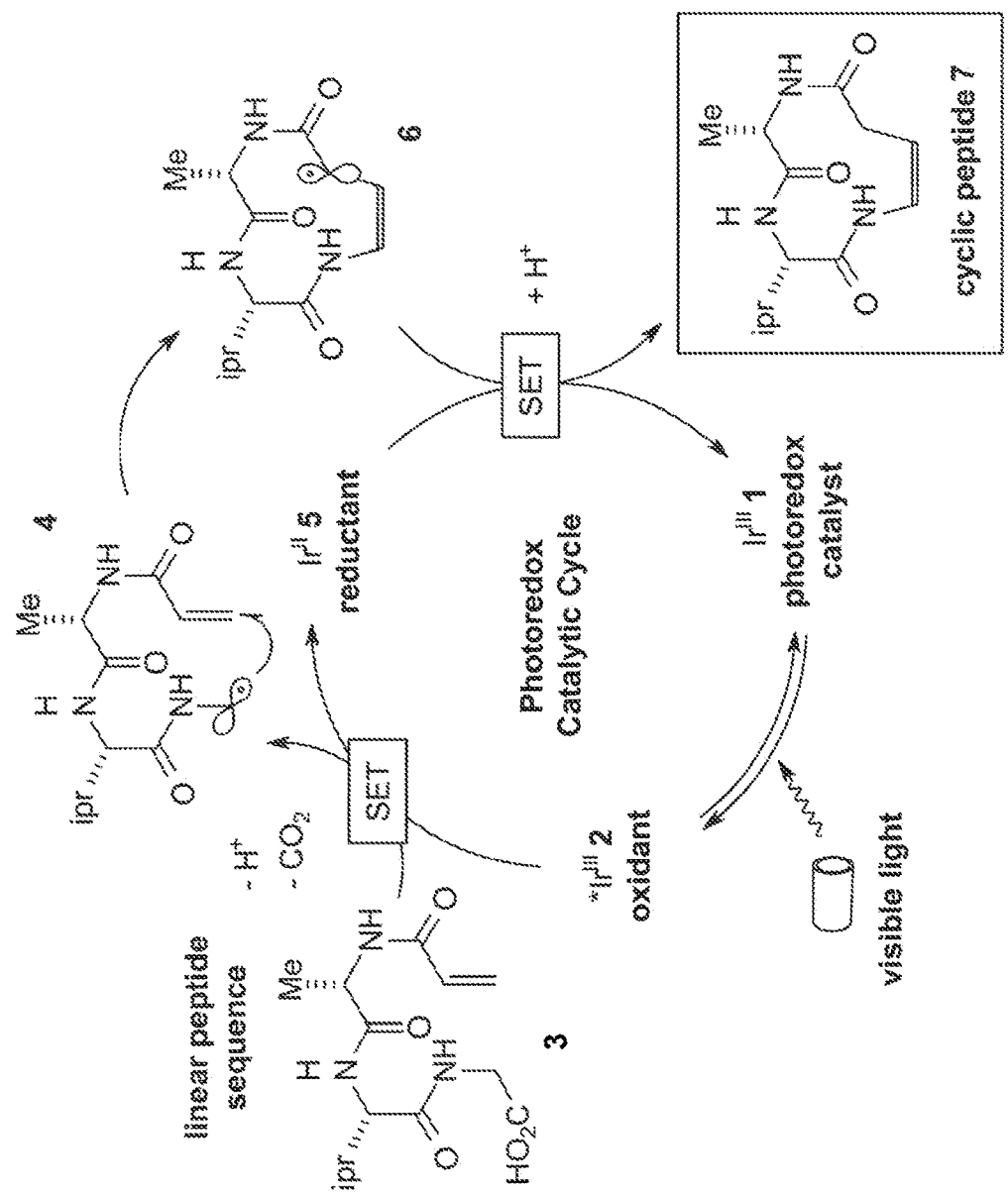
FIG. 9 illustrates a mechanistic pathway of peptide intramolecular cyclization via decarboxylation according to one example of a method described herein.

FIG. 9 illustrates a mechanistic pathway of peptide intramolecular cyclization via decarboxylation according to one example of a method described herein. Under irradiation by visible light, photoredox catalyst Ir[dF(CF$_3$)ppy]$_2$(dtbbpy)$^+$1 absorbs a photon and accesses excited state *Ir[dF(CF$_3$)ppy]$_2$(dtbbpy)$^+$2, a strong oxidant ($E_{1/2}^{red}$[Ir$^{III}$/Ir$^{II}$]=+1.21 V vs SCE in MeCN). SET oxidation of the carboxylate salt of 3, generated in situ by action of a base, subsequently occurs. The resulting carboxyl radical then rapidly extrudes CO$_2$ to produce α-amino radical 4 and reduced photocatalyst Ir[dF(CF$_3$)ppy]$_2$(dtbbpy) 5. Entropically uphill organization of intermediate 4 into a product-like reactive conformation then occurs. Intramolecular conjugate addition of nucleophilic α-amino radical 4 with the pendant Michael acceptor constructs the desired C—C bond and provides α-acyl radical 6. Closure of the photoredox catalytic cycle occurs via SET reduction of intermediate 6. Finally, protonation of the resulting enolate furnishes desired cyclic peptide product 7.

Figure 10:
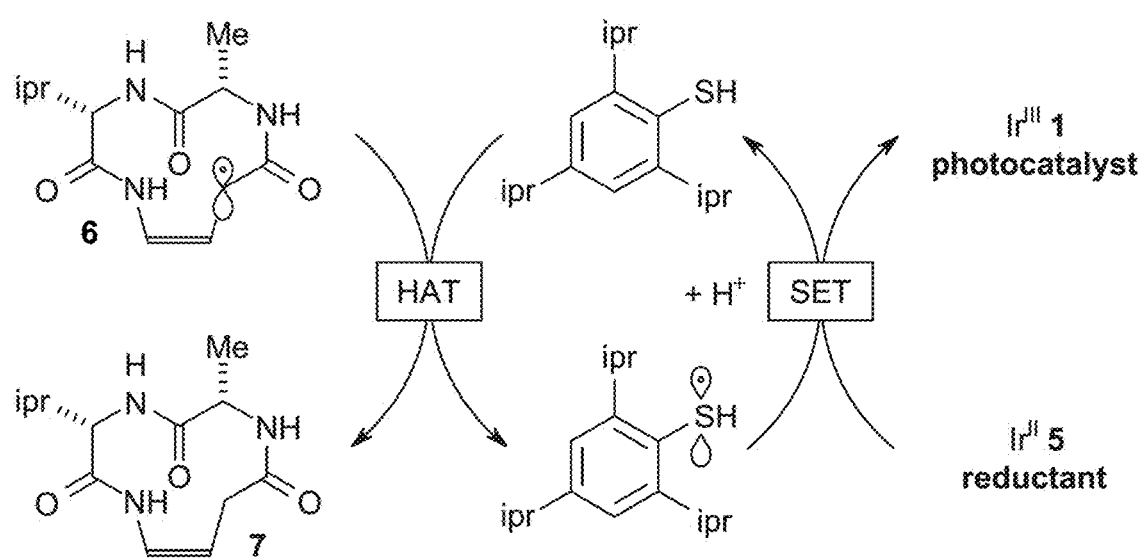
FIG. 10 illustrates a mechanistic pathway wherein thiol co-catalyst is employed for hydrogen atom transfer to an acyl radical according to some embodiments described herein.
Figure 11:
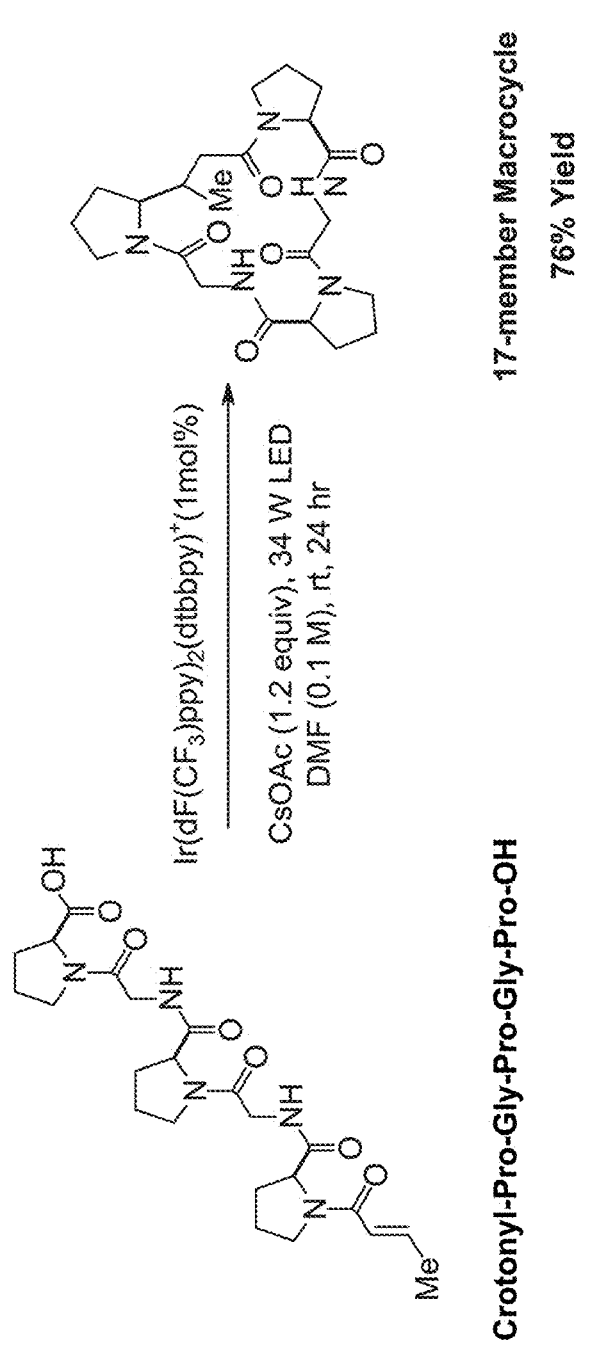
FIG. 11 illustrates an example of peptide intramolecular cyclization according to one embodiment of a method described herein. Figure discloses SEQ ID NO: 53.

FIG. 10 illustrates a mechanistic pathway wherein aryl thiol co-catalyst is employed for HAT to the acyl radical 6. Subsequent to HAT, the resulting thiyl radical can be reduced by Ir(II) to close the photocatalytic cycle. FIG. 11 illustrates a non-limiting example of peptide intramolecular cyclization according to one embodiment of a method described herein.

In some embodiments, peptide intramolecular cyclization does not occur between the Michael acceptor functionalized N-terminal residue and C-terminus residue. For example, the functionalized N-terminal residue may react with an interior residue having side chain carboxyl functionality. In such embodiments, the C-terminus residue can be inactivated with a protecting group. Coupling the functionalized N-terminal residue to an interior amino acid via a decarboxylative pathway can enable the production of a variety of cyclized peptide structures. For example, the size of the peptide cyclic structure can be varied according to the position of the interior residue participating in the decaboxylative pathway. In some embodiments, reaction of the functionalized N-terminal residue with an interior residue is precluded by protecting interior residues having acid functionalities.

IV. Decarboxylative Conjugate Addition

In an additional aspect, general methods of conjugate addition are described herein. A method of conjugate addition comprises providing a reaction mixture including a Michael acceptor and a substrate having a carboxyl group and coupling the Michael acceptor and substrate via a mechanism including decarboxylation of the substrate.

Figure 12:
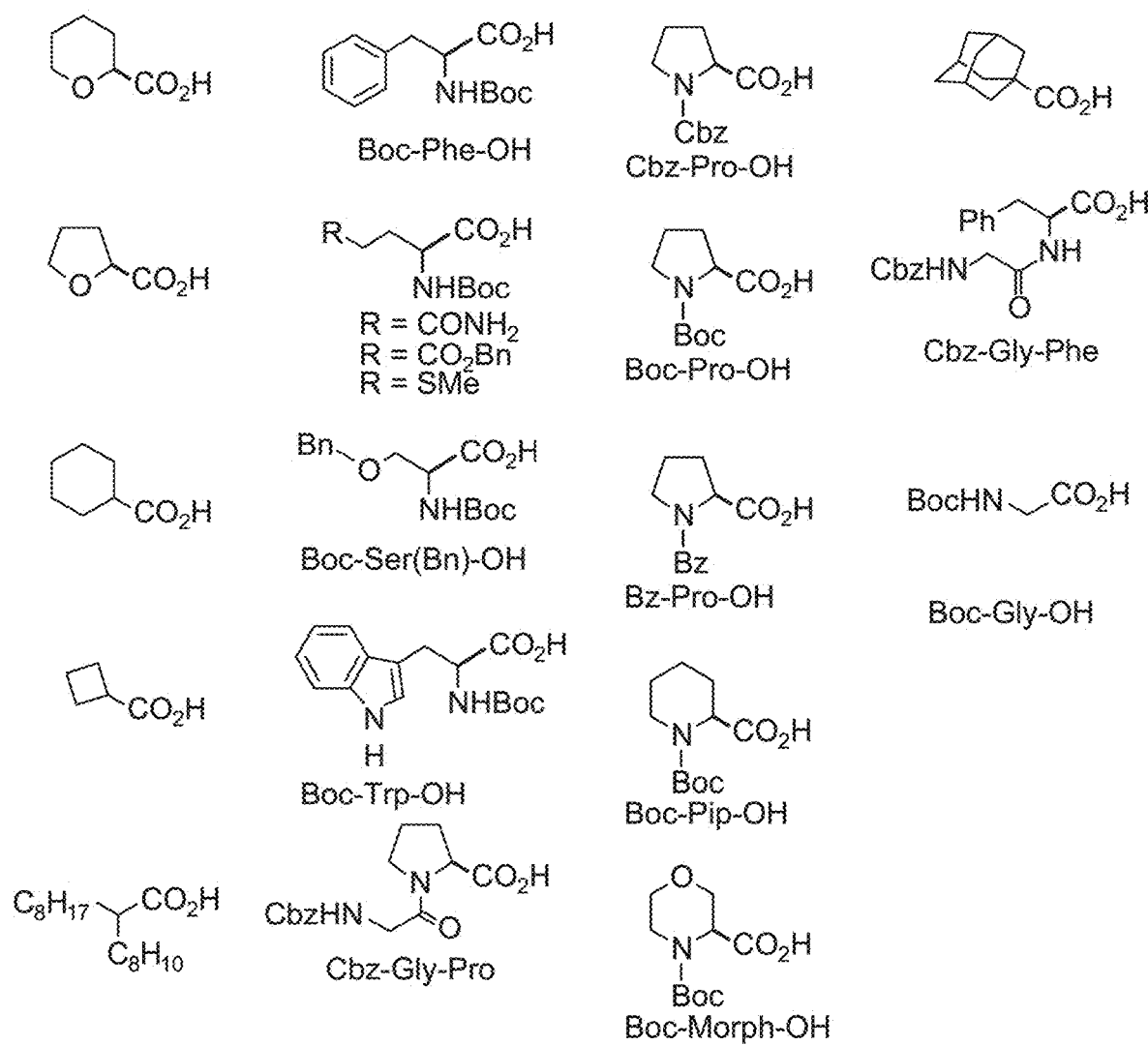
FIG. 12 illustrates various carboxylic acid substrates according to some embodiments described herein.

Any substrate including a carboxyl group operable to undergo decarboxylative mechanistic pathways described herein can be employed in the reaction mixture. In some embodiments, a substrate of the reaction mixture is an aliphatic carboxylic acid. In being an aliphatic acid, the carboxyl functional group is not directly bonded to an aromatic ring, such as a phenyl ring. Aliphatic carboxylic acid, in some embodiments, is of the formula R$^3$—CO$_2$H. R$^3$ can be a saturated hydrocarbon or a hydrocarbon having one or more points of unsaturation. Further, saturated or unsaturated hydrocarbons can incorporate or be substituted with one or more heteroatoms including nitrogen, oxygen and/or sulfur. Therefore, R$^3$ can be selected from the group consisting of -alkyl, -cycloalkyl, -heteroalkyl, -heterocycloalkyl, -alkenyl, -cycloalkenyl, -heteroalkenyl, -heterocycloalkenyl, -alkynyl, -alkyl-aryl, -alkyl-heteroaryl, -alkylalkoxy, -alkenyl-aryl, -alkenyl-heteroaryl, -cycloalkyl-aryl, -cycloalkyl-heteroaryl, -cycloalkenyl-aryl, -heterocycloalkenyl-aryl, and -alkenyl-alkoxy. FIG. 12 illustrates various carboxylic acid substrates according to some embodiments described herein. Additionally, carboxylic acid substrate can be selected from the amino acids provided in Table I above.

The reaction mixture can also include one or more catalytic species to assist in the decarboxylative coupling of the Michael acceptor and substrate. Catalytic species, in some embodiments, participate in forming a carboxyl radical which then rapidly extrudes CO$_2$ to produce an alkyl radical. The alkyl radical is subsequently operable to undergo conjugate addition with the Michael acceptor to forge a new C—C bond with concomitant formation of an α-acyl radical. The α-acyl radical is subsequently reduced by the catalyst. Catalyst can participate in carboxyl radical formation via a single electron transfer (SET) process. For example, catalyst can act in an oxidative capacity to produce the carboxyl radical followed by CO$_2$ extrusion. Alternatively, catalyst can act in reductive capacity to produce the carboxyl radical followed by CO$_2$ extrusion. Any catalyst operable to initiate carboxyl radical formation followed by CO$_2$ extrusion is contemplated herein. In some embodiments, catalytic species initiating carboxyl radical formation can also close the redox cycle by single electron transfer (SET) to the α-acyl radical formed by the conjugate addition. In other embodiments, different catalytic species or co-catalysts are used for carboxyl radical formation and acyl radical reduction.

Various transition metal catalysts may be operable to participate in the foregoing decarboxylative mechanisms and associated SET and/or redox processes. Nickel catalyst and/or noble metal catalyst, for example, may be suitable for use in coupling methods described herein. In some embodiments, catalyst is photoredox catalyst. Any photoredox catalyst operable to participate in in decarboxylative mechanisms described herein can be used in the reaction mixture. For example, photoredox catalyst can include one or more iridium and/or ruthenium complexes. In some embodiments, heteroleptic iridium complexes are selected as the photocatalyst. Suitable heteroleptic iridium complexes include $Ir[dF(CF_3)ppy]_2(dtbbpy)^+$, $Ir(dF(CF_3)ppy)_2(4,4'-dcbpy)$ and $Ir(ppy)_2(dtbbpy)^+$. Homoleptic iridium complexes, such as $Ir(dFppy)_3$, can also be used as photocatalyst. Moreover, photoredox catalyst may be present in the reaction mixture in an amount selected from Table IV herein.

In further embodiments, one or more electrochemical methods may be used to initiate carboxyl radical formation and/or acyl radical reduction. For example, one or more electrodes can be positioned in the reaction mixture to initiate decarboxylative mechanisms and associated SET and/or redox processes described herein. Additionally, one or more reducing metals, such as zinc, may be used to initiate carboxyl radical formation and/or acyl radical reduction. Base and solvent components described in Section I above complete the reaction mixture.

Figure 13:
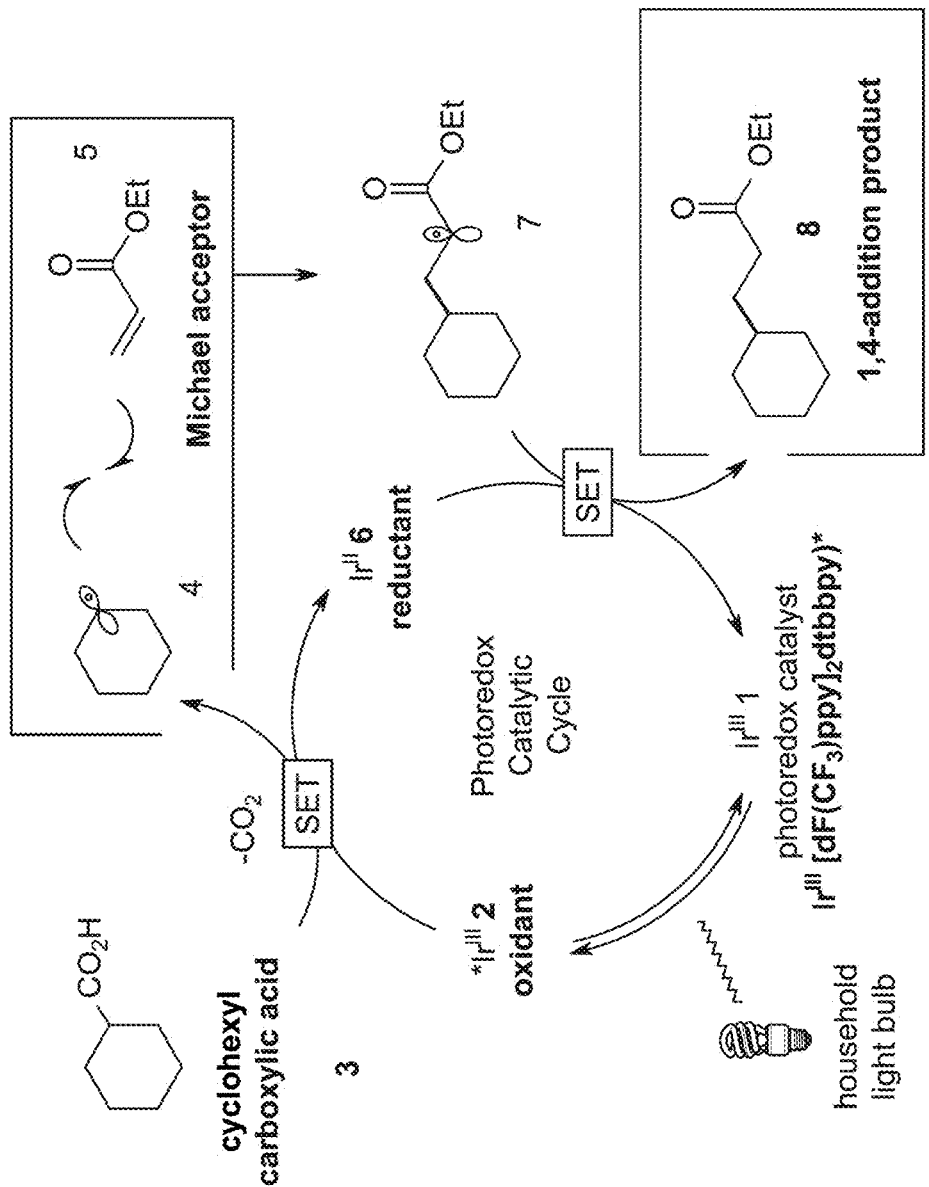
FIG. 13 illustrates a mechanistic pathway of conjugate addition via decarboxylation according to one example of a method described herein.

While not wishing to be bound by any theory, FIG. 13 illustrates a mechanistic pathway of conjugate addition via decarboxylation according to one example of a method described herein. Iridium photoredox catalyst, such as $Ir[dF(CF_3)ppy]_2(dtbbpy)^{+1}$ can readily accept photons from a visible light source to generate the strongly oxidizing excited state $*Ir[dF(CF_3)ppy]_2(dtbbpy)^{+2}$. The carboxylic acid 3 undergoes base-promoted deprotonation and subsequent single electron transfer (SET) oxidation of the resulting carboxylate functionality by the visible-light-excited photocatalyst $*Ir[dF(CF_3)ppy]_2(dtbbpy)^{+2}$, thereby generating the reduced $Ir[dF(CF_3)ppy]_2(dtbbpy)$ 6 and the carboxyl radical species which immediately extrudes $CO_2$ to give the SOMO species 4. The alkyl radical 4 undergoes conjugate addition with the electron deficient olefin 5 to forge a new C—C bond with concomitant formation of the alkyl radical 7. Facile SET reduction of the α-acyl radical 7 by the strongly reducing $Ir[dF(CF_3)ppy]_2(dtbbpy)$ 6 provides the 1,4-conjugate addition product while regenerating the $Ir[dF(CF_3)ppy]_2(dtbbpy)^{+1}$ photocatalyst.

Examples of conjugate addition, peptide functionalization, peptide coupling and peptide intramolecular cyclization are provided in the following Examples section.

V. Examples

Materials and Methods

The following Examples were conducted with the materials and methods described herein. Commercial reagents were purchased from Sigma Aldrich and purified prior to use following the guidelines of Perrin and Armarego, *Purification of Laboratory Chemicals*, Pergamon, Oxford, ed.3 1988) (hereinafter "Perrin"). All solvents were purified by passage through columns of activated alumina. Organic solutions were concentrated under reduced pressure on a Büchi rotary evaporator using an acetone-dry ice bath for volatile compounds. Chromatographic purification of products was accomplished by flash chromatography on silica gel (Fluka, 230-400 mesh). Thin layer chromatography (TLC) was performed on Analtech Uniplate 250 m silica gel plates. Visualization of the developed chromatogram was performed by fluorescence quenching, p-anisaldehyde, potassium permanganate, or ceric ammonium molybdate stain. $^1H$ and $^{13}C$ NMR spectra were recorded on a Bruker 500 (500 and 125 MHz) instrument, and are internally referenced to residual protio solvent signals (note: $CDCl_3$ referenced at 7.26 and 77.0 ppm respectively). Data for $^1H$ NMR are reported as follows: chemical shift (δ ppm), integration, multiplicity (s=singlet, d=doublet, t=triplet, q=quartet, m=multiplet), coupling constant (Hz) and assignment. Data for $^{13}C$ NMR are reported in terms of chemical shift and no special nomenclature is used for equivalent carbons. High resolution mass spectra were obtained at Princeton University mass spectrometry facilities. All amino acids were used from commercial suppliers. All aryl and heteroaryl halides were used from commercial suppliers or prepared using standard literature procedures.

General Procedure for Decarboxylative Peptide Functionalization (FIGS. 3-4)

To an 8 mL vial equipped with a magnetic stir bar was added Cbz-βAla-Ala-Phe-Gly-Ala-Phe-Gly-Val-OH (SEQ ID NO: 1) (0.10 mmol, 1.0 equiv.), diethyl 2-ethylidenemalonate (0.10 mmol, 1.0 equiv.), cesium acetate (0.12 mmol, 1.2 equiv.), $Ir[dF(CF_3)ppy]_2(dtbbpy)PF_6$ (1.0 μmol, 0.01 equiv.), and 1.0 mL of DMF. The vial was sealed with a Teflon cap and sparged with nitrogen gas for 15 min (solution changes from yellow to a pale green). Then, the vial was sealed with parafilm and placed inside a fan-cooled reflective chamber. Finally, the vial was exposed to one 34 W blue LED under magnetic stirring for 48 hr. Peptides over 4 residues in length can be precipitated out by addition of an excess of cold diethyl ether in preparation for purification by reverse-phase HPLC. For shorter peptide sequences, the reaction mixture was diluted with a saturated aqueous $NaHCO_3$ solution and extracted with ethyl acetate (3×50 mL). The combined organic extracts were washed with water and brine, dried over anhydrous $MgSO_4$, and concentrated in vacuo. Purification of the crude product by flash chromatography on silica gel afforded the desired product.

General Procedure for Decarboxylative Peptide Coupling (FIG. 8)

To an 8 mL vial equipped with a magnetic stir bar was added Cbz-Phe-Leu-Gly-Pro-OH (SEQ ID NO: 2) (0.10 mmol, 1.0 equiv.), Crotonyl-Phe-Ala-Pro-Gly-OMe (SEQ ID NO: 3) (0.10 mmol, 1.0 equiv.), dibasic potassium phosphate (0.12 mmol, 1.2 equiv.), $Ir[dF(CF_3)ppy]_2(dtbbpy)PF_6$ (1.0 μmol, 0.01 equiv.), and 1.0 mL of DMF. The vial was sealed with a Teflon cap and sparged with nitrogen gas for 15 min (solution changes from yellow to a pale green). Then, the vial was sealed with parafilm and placed inside a fan-cooled reflective chamber. Finally, the vial was exposed to one 26 W CFL bulb under magnetic stirring for 48 hr. The crude material can be precipitated out by addition of an excess of cold diethyl ether in preparation for purification by reverse-phase HPLC.

General Procedure for Decarboxylative Peptide Intramolecular Cyclization

Commercial reagents were purified prior to use following the guidelines of Perrin and Armarego. (Perrin, D. D.; Armarego, W. L. F. *Purification of Laboratory Chemicals*, 3rd ed. Pergamon Press: Oxford, 1988). $Ir[dF(CF_3)ppy]_2(dtbbpy)PF_6$ was prepared according to the literature procedure. (Lowry, M. S.; Goldsmith, J. I.; Slinker, J. D.; Rohl, R.; Pascal, Jr., R. A.; Malliaras, G. G.; Bernhard, S. *Chem. Mater.* 2005, 17, 5712). 2,4,6-Triisopropylbenzenethiol was prepared according to literature procedure and purified by distillation prior to use. (Renard, M.; Ghosez, L. A. *Tetrahedron* 2001, 57, 2597). All solvents were purified according to the method of Grubbs. (Pangborn, A. B.; Giardello, M. A.; Grubbs, R. H.; Rosen, R. K.; Timmers, F. J. Safe and Convenient Procedure for Solvent Purification. *Organometallics* 1996, 15, 1518). Organic solutions were concentrated under reduced pressure on a Büchi rotary evaporator using a water bath. Solid phase peptide synthesis was performed on 2-chlorotrityl chloride resin (100-200 mesh, 1.2 meq/g, crosslinked polystyrene) manually or on a Prelude automated peptide synthesizer. 2-chlorotrityl chloride resin, 2-(1H-benzotriazol-1-yl)-1,3,3-tetranethyluroniurm hexafluorophosphate (HBTU), N,N-diisopropylethylamine (DIPEA), and Fmoc-amino acids were purchased from Chem Impex Int'l Inc. and used as received. 1,1,1,3,3,3-hexafluoro-2-propanol (HFIP) was purchased from Oakwood Chemical and used as received. $^1$H NMR spectra were recorded on a Bruker UltraShield Plus 500 MHz unless otherwise noted and are internally referenced to residual protio $CD_3OD$ signals (3.31 ppm). Data for $^1$H NMR are reported as follows: chemical shift (δ ppm), multiplicity (s=singlet, d=doublet, t=triplet, q=quartet, m=multiplet, dd=doublet of doublets, dt=doublet of triplets, br=broad), coupling constant (Hz), and integration. $(CD_3)_2SO$ was added for solubility when necessary. $^{13}$C NMR spectra were recorded on a Bruker UltraShield Plus 500 MHz and data are reported in terms of chemical shift relative to $CD_3OD$ (49.2 ppm). High Resolution Mass Spectra were obtained from the Princeton University Mass Spectral Facility.

Synthesis of Linear Peptide Sequences

General Solid Phase Loading Procedure:

Into a 12 mL filtration tube with luer adapter was added 2-chlorotrityl chloride resin (500 mg, 600 µmol) followed by a solution of the Fmoc amino acid (1.8 mmol, 3 equiv.) and DIPEA (0.627 mL, 3.6 mmol, 6 equiv.) in $CH_2Cl_2$ (8 mL). The tube was capped and shaken for 15 minutes and then an additional 2 equiv. of DIPEA added. After a further hour of shaking, 2 equiv. DIPEA and 1 mL MeOH was added and the mixture agitated for 20 minutes. The tube was then drained, rinsed with $CH_2Cl_2$ (3×8 mL) and dried. The amino acid loading of the resin was then measured by Fmoc determination. (Boll, E.; Drobecq, H.; Ollivier, N.; Blanpain, A.; Raibaut, L.; Desmet, R.; Vicogne, J.; Melnyk, O. *Nature Protocols* 2015, 10, 269)

General Solid Phase Synthesis Procedure:

The resin was treated with 20% piperidine/DMF (6 mL) for 5 minutes followed by thorough washing with DMF (6×6 mL). Deprotection was performed twice.

A solution of Fmoc-protected amino acid (1.8 mmol, 3 equiv.) and HBTU (0.68 g, 1.8 mmol, 3 equiv.) in DMF (6 mL) followed by DIPEA (0.627 mL, 3.6 mmol, 6 equiv.) was added to the resin and the mixture shaken for 2 hours. The resin was then drained and rinsed with DMF (6×6 mL). If necessary, the coupling procedure was repeated until completion.

General Acryloyl Capping Procedure:

A solution of pentafluorophenyl acrylate (0.43 g, 1.8 mmol, 3 equiv., prepared according to literature procedure) and DIPEA (0.627 mL, 3.6 mmol, 6 equiv.) in DMF (6 mL) was added to the resin and the mixture shaken for 4 hours. The resin was drained and rinsed with DMF (6×6 mL). The procedure was repeated twice.

General Resin Cleavage Procedure:

After completion of synthesis, resin was thoroughly rinsed with DMF (6×6 mL) then $CH_2Cl_2$ (6×6 mL). The resin was then treated with 4:1 $CH_2Cl_2$:HFIP twice for 1 hour each. The combined $CH_2Cl_2$:HFIP solutions were concentrated under reduced pressure. Cold $Et_2O$ was added to the remaining solid, which was then centrifuged and decanted; this procedure was repeated twice. The remaining solid was dried under a stream of $N_2$ and then under reduced pressure to yield the desired crude peptide. If necessary, preparative HPLC purification was carried out.

General Decarboxylative Macrocyclization Procedure

General Procedure for the Decarboxylative Macrocyclization of N-Acryloyl Peptides:

To a dry 8 mL vial equipped with a stir bar was added $Ir[dF(CF_3)ppy]_2(dtbbpy)PF_6$ (1.3 mg, 1.2 µmol, 0.12 equiv.), peptide (10.0 µmol, 1.0 equiv.), $K_2HPO_4$ (3.5 mg, 20.0 µmol, 2.0 equiv.), water (0.36 µL, 20.0 µmol, 2.0 equiv.), and DMF (4 mL). The vial was capped and the reaction mixture was degassed by sparging with $N_2$ while stirring at 800 RPM for 20 min before sealing the vial with Parafilm. The reaction was stirred at 800 RPM and irradiated with a 34 W blue LED lamp until complete consumption of the starting material, typically within 6 hours. The reaction was centrifuged and subjected to RP-HPLC analysis for yield determination.

The crude materials were purified via preparative LC/MS with the following conditions: Column: XBridge C18, 30×150 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-70% B over 20 minutes, then a 2-minute hold at 100% B; Flow: 40 mL/min. Fractions containing the desired product were combined and dried via centrifugal evaporation.

Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1× 50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

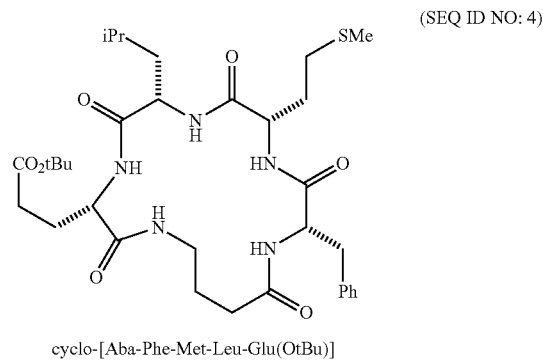 [SMILES: CSCC[C@@H]1NC(=O)[C@H](Cc2ccccc2)NC(=O)CCCNC(=O)[C@H](CCC(=O)OC(C)(C)C)NC(=O)[C@H](CC(C)C)NC1=O]

(SEQ ID NO: 4)

cyclo-[Aba-Phe-Met-Leu-Glu(OtBu)]

Prepared following the general procedure outlined above using acryloyl-Phe-Met-Leu-Glu(tBu)-Gly (SEQ ID NO: 5) (7.1 mg, 10 µmol, 1.0 equiv.), $Ir[dF(CF_3)ppy]_2(dtbbpy)PF_6$ (1.3 mg, 1.2 µmol, 0.12 equiv.), $K_2HPO_4$ (3.5 mg, 20 µmol, 2.0 equiv.), 2, 4, 6-triisopropylbenzenethiol (0.24 mg, 1 μmol, 0.1 equiv.), and DMF (4.0 mL). After 10 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 40%. $^1$H NMR (500 MHz, CD$_3$OD) δ 7.35-7.22 (m, 5H), 4.41 (t, J=7.8 Hz, 1H), 4.26-4.22 (m, 1H), 3.96 (dd, J=11.2, 4.1 Hz, 1H), 3.87 (dd, J=9.5, 4.0 Hz, 1H), 3.15-3.03 (m, 2H), 3.03-2.94 (m, 1H), 2.48 (ddd, J=15.7, 8.9, 5.3 Hz, 1H), 2.37-2.21 (m, 1H), 2.21-2.04 (m, 4H), 2.02 (s, 3H), 2.01-1.96 (m, 2H), 1.86-1.79 (m, 1H), 1.74 (ddd, J=13.8, 10.0, 4.1 Hz, 1H), 1.68-1.60 (m, 1H), 1.46 (s, 9H), 0.95 (dd, J=13.7, 6.5 Hz, 6H); HRMS (ESI-TOF) m/z calcd. for C$_{33}$H$_{52}$N$_5$O$_7$S ([M+H]$^+$) 662.35820, found 662.35806.

(SEQ ID NO: 6)

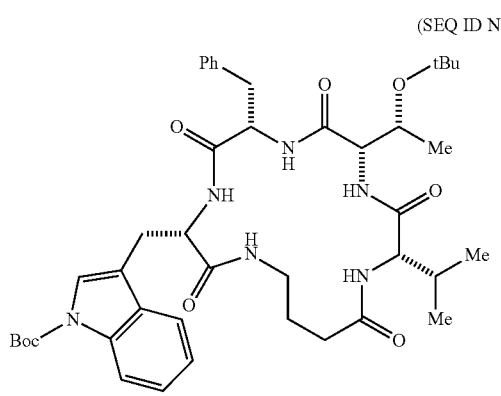

cyclo-[Aba-Val-Thr(tBu)-Phe-Trp(Boc)]

Prepared following the general procedure outlined above using acryloyl-Val-Thr(tBu)-Phe-Trp(Boc)-Gly (SEQ ID NO: 7) (8.2 mg, 10 μmol, 1.0 equiv.), Ir[dF(CF$_3$)ppy]2 (dtbbpy)PF$_6$ (1.3 mg, 1.2 μmol, 0.12 equiv.), K$_2$HPO$_4$ (3.5 mg, 20 μmol, 2.0 equiv.), and DMF (4.0 mL). After 6 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 56%. $^1$H NMR (500 MHz, CD$_3$OD) δ 8.13 (d, J=8.4 Hz, 1H), 7.64 (d, J=7.8 Hz, 1H), 7.38 (s, 1H), 7.33 (t, J=7.7 Hz, 1H), 7.26 (t, J=7.5 Hz, 1H), 7.16-7.03 (m, 5H), 4.27 (dd, J=10.8, 4.7 Hz, 1H), 4.18 (q, J=4.9, 4.3 Hz, 2H), 4.14 (d, J=4.5 Hz, 1H), 4.09-4.01 (m, 1H), 3.49-3.37 (m, 4H), 3.07-2.93 (m, 2H), 2.45 (ddd, J=13.1, 8.3, 4.2 Hz, 1H), 2.34-2.18 (m, 2H), 2.05-1.86 (m, 2H), 1.60 (s, 9H), 1.18 (s, 9H), 1.07 (d, J=6.5 Hz, 3H), 0.98 (dd, J=13.5, 6.8 Hz, 6H); HRMS (ESI-TOF) m/z calcd. for C$_{42}$H$_{59}$N$_6$O$_8$ ([M+H]$^+$) 775.43889, found 775.43881.

(SEQ ID NO: 8)

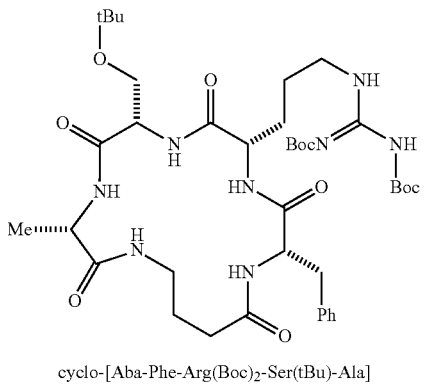

cyclo-[Aba-Phe-Arg(Boc)$_2$-Ser(tBu)-Ala]

Prepared following the general procedure outlined above using acryloyl-Phe-Arg(Boc)$_2$-Ala-Ser(tBu)-Gly (SEQ ID NO: 9) (8.5 mg, 10 μmol, 1.0 equiv.), Ir[dF(CF$_3$)ppy]2 (dtbbpy)PF$_6$ (2.2 mg, 2.0 μmol, 0.20 equiv.), K$_2$HPO$_4$ (3.5 mg, 20 μmol, 2.0 equiv.), 2, 4, 6-triisopropylbenzenethiol (0.24 mg, 1 μmol, 0.1 equiv.), and DMF (4.0 mL). After 12 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 59%. $^1$H NMR (500 MHz, CD$_3$OD) δ 7.33-7.19 (m, 5H), 4.50 (t, J=7.7 Hz, 1H), 4.23 (dd, J=7.1, 3.8 Hz, 1H), 4.06 (q, J=7.2 Hz, 1H), 3.98-3.86 (m, 2H), 3.76 (dd, J=9.5, 3.8 Hz, 1H), 3.40-3.21 (m, 2H), 3.13-3.07 (m, 2H), 2.97 (dd, J=13.7, 8.0 Hz, 1H), 2.29 (ddd, J=13.6, 8.4, 4.6 Hz, 1H), 2.21 (ddd, J=14.6, 7.4, 4.7 Hz, 1H), 1.94-1.86 (m, 4H), 1.78 (dtd, J=14.0, 9.8, 4.9 Hz, 1H), 1.54 (s, 9H), 1.46 (s, 9H), 1.44-1.38 (m, 1H), 1.35-1.27 (m, 1H), 1.23 (s, 9H), 1.20-1.16 (m, 2H); HRMS (ESI-TOF) m/z calcd. for C$_{39}$H$_{63}$N$_8$O$_{10}$ ([M+H]$^+$) 803.46617, found 803.46697.

(SEQ ID NO: 10)

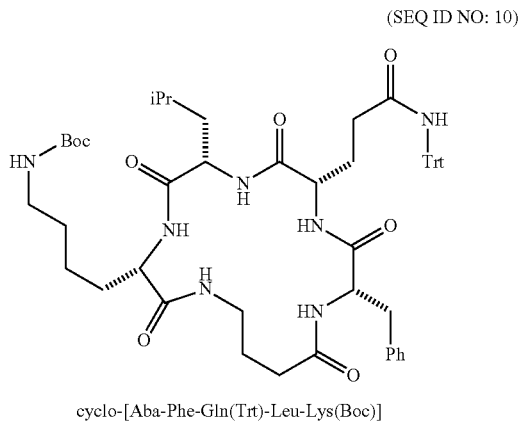

cyclo-[Aba-Phe-Gln(Trt)-Leu-Lys(Boc)]

Prepared following the general procedure outlined above using acryloyl-Phe-Gln(Trt)-Leu-Lys(Boc)-Gly (SEQ ID NO: 11) (9.9 mg, 10 μmol, 1.0 equiv.), Ir[dF(CF$_3$)ppy]2 (dtbbpy)PF$_6$ (1.3 mg, 1.2 μmol, 0.12 equiv.), K$_2$HPO$_4$ (3.5 mg, 20 μmol, 2.0 equiv.), and DMF (4.0 mL). After 6 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 94%. $^1$H NMR (500 MHz, CD$_3$OD) δ 7.33-7.16 (m, 20H), 4.38 (dd, J=9.1, 6.3 Hz, 1H), 4.15-4.05 (m, 1H), 3.95 (dd, J=11.0, 4.1 Hz, 1H), 3.70 (d, J=8.9 Hz, 1H), 3.20-2.89 (m, 6H), 2.31-2.19 (m, 4H), 2.15-2.02 (m, 2H), 2.02-1.87 (m, 3H), 1.85-1.78 (m, 1H), 1.78-1.63 (m, 2H), 1.50-1.42 (m, 12H), 1.34-1.29 (m, 1H), 0.95 (dd, J=13.2, 6.3 Hz, 6H); HRMS (ESI-TOF) m/z calcd. for C$_{54}$H$_{70}$N$_7$O$_8$ ([M+H]$^+$) 944.52084, found 944.52716.

(SEQ ID NO: 12)

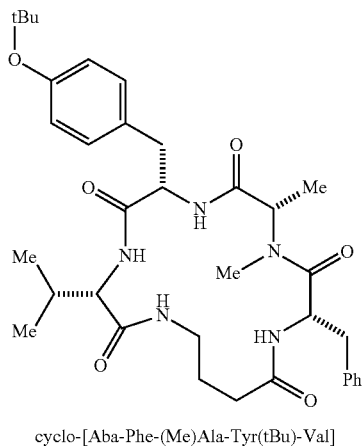

cyclo-[Aba-Phe-(Me)Ala-Tyr(tBu)-Val]

Prepared following the general procedure outlined above using acryloyl-Phe-(Me)Ala-Tyr(tBu)-Val-Gly (SEQ ID NO: 13) (6.8 mg, 10 μmol, 1.0 equiv.), Ir[dF(CF$_3$)ppy]2(dtbbpy)PF$_6$ (0.9 mg, 0.8 μmol, 0.08 equiv.), K$_2$HPO$_4$ (3.5 mg, 20 μmol, 2.0 equiv.), and DMF (2.0 mL). After 10 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 66%. $^1$H NMR (500 MHz, CD$_3$OD) NMR spectrum complicated due to the presence of rotamers. δ 7.34-7.21 (m, 5H), 7.13 (dd, J=18.4, 8.1 Hz, 2H), 6.92 (dd, J=20.1, 8.1 Hz, 2H), 4.37 (t, J=11.9 Hz, 1H), 4.28 (q, J=6.9 Hz, 1H), 4.14 (dt, J=10.2, 5.5 Hz, 2H), 3.29-3.19 (m, 2H), 3.09 (dt, J=13.1, 6.0 Hz, 1H), 3.05-2.84 (m, 2H), 2.63 (s, 3H), 2.58-2.46 (m, 1H), 2.43-2.27 (m, 3H), 2.23-2.13 (m, 1H), 1.95-1.86 (m, 1H), 1.85-1.73 (m, 1H), 1.30 (s, 9H), 0.96 (d, J=6.8 Hz, 3H), 0.75 (d, J=6.9 Hz, 3H), 0.34 (d, J=6.7 Hz, 3H); HRMS (ESI-TOF) m/z calcd. for C$_{35}$H$_{50}$N$_5$O$_6$ ([M+H]$^+$) 636.37556, found 636.37528.

(SEQ ID NO: 14)

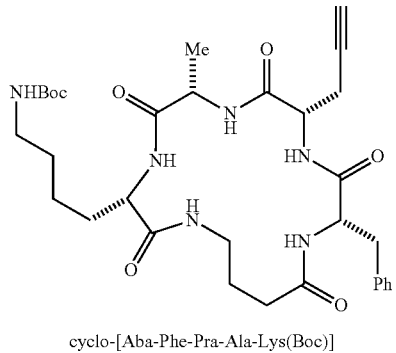

cyclo-[Aba-Phe-Pra-Ala-Lys(Boc)]

Prepared following the general procedure outlined above using acryloyl-Phe-Pra-Ala-Lys(Boc)-Gly (SEQ ID NO: 15) (6.7 mg, 10 μmol, 1.0 equiv.), Ir[dF(CF$_3$)ppy]2(dtbbpy)PF$_6$ (0.9 mg, 0.8 μmol, 0.08 equiv.), K$_2$HPO$_4$ (3.5 mg, 20 μmol, 2.0 equiv.), and DMF (2.0 mL). After 10 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 82%. Rotameric $^1$H NMR spectrum. $^1$H NMR (500 MHz, CD$_3$OD) δ 7.39-7.23 (m, 5H), 4.49-4.35 (m, 1.2H), 4.31-4.24 (m, 0.8H), 4.01-3.96 (m, 2H), 3.36-3.27 (m, 2H), 3.15-3.05 (m, 3H), 3.03 (s, 1H), 3.01-2.87 (m, 2H), 2.88-2.77 (m, 1H), 2.43 (t, J=2.6 Hz, 1H), 2.38-2.28 (m, 1H), 2.27-2.21 (m, 1H), 2.17-2.00 (m, 1H), 1.95 (m, 1H), 1.88-1.83 (m, 1H), 1.82-1.65 (m, 1H), 1.59 (d, J=7.2 Hz, 3H), 1.56-1.49 (m, 2H), 1.46 (s, 9H), 1.36 (m, 1H); 6 HRMS (ESI-TOF) m/z calcd. for C$_{32}$H$_{47}$N$_6$O$_7$ ([M+H]$^+$) 627.35007, found 627.34889.

(SEQ ID NO: 16)

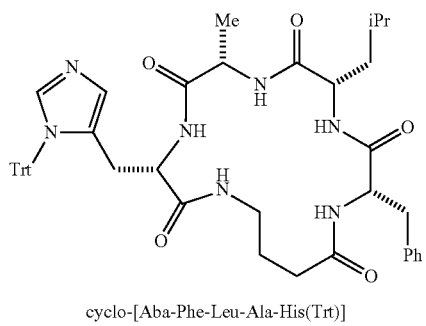

cyclo-[Aba-Phe-Leu-Ala-His(Trt)]

Prepared following the general procedure outlined above using acryloyl-Phe-Leu-Ala-His(Trt)-Gly (SEQ ID NO: 17) (0.84 mg, 1 μmol, 1.0 equiv.), Ir[dF(CF$_3$)ppy]$_2$(dtbbpy)PF$_6$ (0.13 mg, 0.12 μmol, 0.12 equiv.), K$_2$HPO$_4$ (0.35 mg, 2 μmol, 2.0 equiv.), and DMF (1.0 mL). After 20 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 65%. $^1$H NMR (500 MHz, CD$_3$OD) δ 7.49-7.20 (m, 22H), 4.48 (dd, J=10.6, 3.8 Hz, 1H), 4.38 (dd, J=9.0, 6.5 Hz, 1H), 3.96 (q, J=7.1 Hz, 1H), 3.75 (dd, J=10.4, 4.5 Hz, 1H), 3.18-3.09 (m, 2H), 3.07-3.01 (m, 1H), 2.95 (dd, J=13.9, 8.9 Hz, 1H), 2.38-2.29 (m, 1H), 2.28-2.21 (m, 1H), 2.10-1.97 (m, 1H), 1.77 (br s, 1H), 1.65-1.57 (m, 1H), 1.56-1.49 (m, 1H), 1.40 (d, J=7.1 Hz, 3H), 1.36-1.21 (m, 2H), 0.99-0.87 (m, 1H), 0.84 (dd, J=13.1, 6.5 Hz, 6H); HRMS (ESI-TOF) m/z calcd. for $C_{47}H_{54}N_7O_5$ ([M+H]$^+$) 796.41809, found 796.41739.

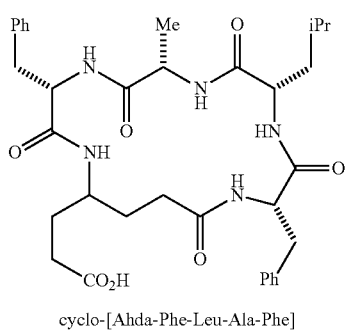

(SEQ ID NO: 18)

cyclo-[Ahda-Phe-Leu-Ala-Phe]

Prepared following the general procedure outlined above using acryloyl-Phe-Leu-Ala-Phe-Glu-TFA (SEQ ID NO: 19) (7.4 mg, 10 μmol, 1.0 equiv.), Ir[dF(CF$_3$)ppy]$_2$(dtbbpy)PF$_6$ (1.3 mg, 1.2 μmol, 0.12 equiv.), K$_2$HPO$_4$ (10.5 mg, 60 μmol, 6.0 equiv.), and DMF (4.0 mL). After 12 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 38%. $^1$H NMR (500 MHz, CD$_3$OD) δ 7.35-7.18 (m, 10H), 4.58 (td, J=8.1, 2.0 Hz, 1H), 4.08 (dt, J=9.8, 6.4 Hz, 1H), 3.92-3.80 (m, 2H), 3.71 (br s, 1H), 3.40-3.36 (m, 1H), 3.09 (dd, J=13.8, 8.0 Hz, 1H), 2.97 (dd, J=13.7, 8.0 Hz, 1H), 2.50 (ddd, J=21.9, 9.9, 4.9 Hz, 1H), 2.42-2.27 (m, 2H), 2.22 (dt, J=15.4, 4.9 Hz, 1H), 2.13-1.95 (m, 3H), 1.84-1.72 (m, 2H), 1.44 (ddt, J=13.7, 9.7, 5.2 Hz, 1H), 1.32 (d, J=7.1 Hz, 3H), 1.27 (br s, 1H), 0.89 (dd, J=30.5, 6.5 Hz, 6H); HRMS (ESI-TOF) m/z calcd. for $C_{34}H_{46}N_5O_7$ ([M+H]$^+$) 636.33918, found 636.33862.

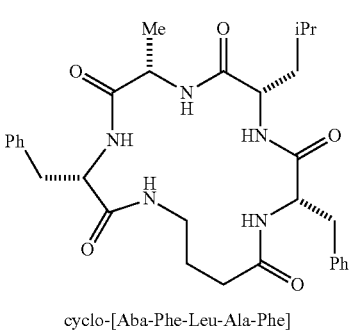

(SEQ ID NO: 20)

cyclo-[Aba-Phe-Leu-Ala-Phe]

Prepared following the general procedure outlined above using acryloyl-Phe-Leu-Ala-Phe-Gly (SEQ ID NO: 21) (6.1 mg, 10 μmol, 1.0 equiv.), Ir[dF(CF$_3$)ppy]$_2$(dtbbpy)PF$_6$ (1.3 mg, 1.2 μmol, 0.12 equiv.), K$_2$HPO$_4$ (3.5 mg, 20 μmol, 2.0 equiv.), and DMF (4.0 mL). After 6 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 93%. $^1$H NMR (500 MHz, CD$_3$OD) δ 7.34-7.18 (m, 10H), 4.49 (t, J=7.8 Hz, 1H), 4.23 (dd, J=11.3, 4.4 Hz, 1H), 3.96 (q, J=7.0 Hz, 1H), 3.80 (dd, J=11.0, 4.0 Hz, 1H), 3.39-3.22 (m, 3H), 3.21-3.13 (m, 2H), 3.09 (dd, J=13.8, 8.1 Hz, 1H), 3.00 (dd, J=13.7, 7.7 Hz, 1H), 2.29 (dd, J=8.3, 4.8 Hz, 2H), 1.93 (q, J=6.5 Hz, 2H), 1.80 (ddd, J=14.6, 11.1, 4.4 Hz, 1H), 1.52 (ddd, J=13.8, 9.9, 4.2 Hz, 1H), 1.28 (d, J=7.3 Hz, 3H), 1.21-1.09 (m, 1H), 0.87 (d, J=6.6 Hz, 3H), 0.81 (d, J=6.5 Hz, 3H)$^{13}$C NMR (126 MHz, CD$_3$OD) δ 175.90, 174.94, 174.76, 174.41, 173.99, 139.92, 138.14, 130.40, 130.37, 129.83, 129.63, 128.13, 127.77, 58.24, 57.07, 54.48, 52.27, 40.21, 39.74, 38.55, 36.99, 33.70, 25.67, 24.25, 24.19, 21.38, 16.65; HRMS (ESI-TOF) m/z calcd. for $C_{31}H_{42}N_5O_5$ ([M+H]$^+$) 564.31805, found 564.31752.

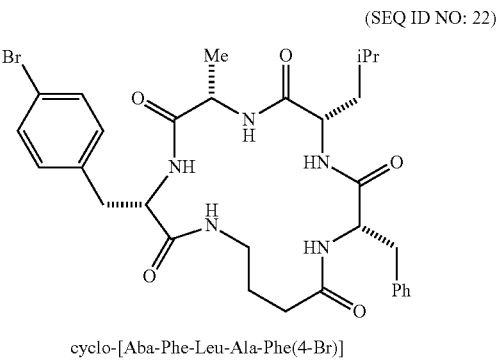 [SMILES: CC(C)C[C@@H]1NC(=O)[C@H](Cc2ccccc2)NC(=O)CCCNC(=O)[C@H](Cc2ccc(Br)cc2)NC(=O)[C@H](C)NC1=O]

(SEQ ID NO: 22)

cyclo-[Aba-Phe-Leu-Ala-Phe(4-Br)]

Prepared following the general procedure outlined above using acryloyl-Phe-Leu-Ala-Phe(4-Br)-Gly (SEQ ID NO: 23) (0.42 mg, 1 μmol, 1.0 equiv.), Ir[dF(CF$_3$)ppy]$_2$(dtbbpy)PF$_6$ (0.13 mg, 0.12 μmol, 0.12 equiv.), K$_2$HPO$_4$ (0.35 mg, 2 μmol, 2.0 equiv.), 2, 4, 6-triisopropylbenzenethiol (0.024 mg, 0.1 μmol, 0.1 equiv.), and DMF (0.4 mL). After 7 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 48%. $^1$H NMR (500 MHz, CD$_3$OD) δ 7.49-7.45 (m, 2H), 7.33-7.27 (m, 4H), 7.23-7.19 (m, 3H), 4.49 (t, J=8.0 Hz, 1H), 4.24 (ddd, J=11.5, 7.4, 4.2 Hz, 1H), 3.97 (td, J=8.2, 7.4, 5.5 Hz, 1H), 3.77 (ddd, J=11.1, 7.0, 4.0 Hz, 1H), 3.38 (dt, J=12.9, 6.2 Hz, 1H), 3.33-3.21 (m, 2H), 3.20-3.11 (m, 1H), 3.08-2.94 (m, 2H), 2.37-2.23 (m, 2H), 2.00-1.87 (m, 2H), 1.79 (ddd, J=13.4, 11.1, 4.1 Hz, 1H), 1.49 (ddd, J=13.8, 10.1, 4.1 Hz, 1H), 1.27 (d, J=7.2 Hz, 3H), 1.09-0.90 (m, 2H), 0.88 (d, J=6.5 Hz, 3H), 0.80 (d, J=6.4 Hz, 3H); HRMS (ESI-TOF) m/z calcd. for $C_{31}H_{41}BrN_5O_5$ ([M+H]$^+$) 642.22856, found 642.22785.

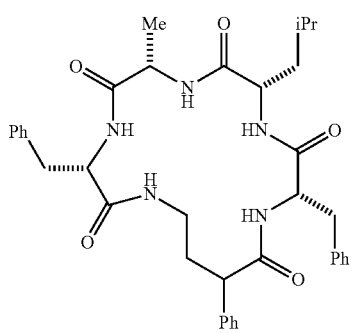

cyclo-[Aba(2-Ph)-Phe-Leu-Ala-Phe] (SEQ ID NO: 24)

Prepared following the general procedure outlined above using α-phenylacryloyl-Phe-Leu-Ala-Phe-Gly (SEQ ID NO: 25) (6.8 mg, 10 μmol, 1.0 equiv.), Ir[dF(CF$_3$)ppy]$_2$(dtbbpy)PF$_6$ (1.3 mg, 1.2 μmol, 0.12 equiv.), K$_2$HPO$_4$ (3.5 mg, 20 μmol, 2.0 equiv.), and DMF (4.0 mL). After 6 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 95%, 10:1 dr. $^1$H NMR (500 MHz, CD$_3$OD) δ 7.40-7.12 (m, 15H), 4.58 (t, J=7.9 Hz, 1H), 4.27 (dd, J=8.9, 6.7 Hz, 1H), 3.97 (q, J=7.2 Hz, 1H), 3.78 (dd, J=11.1, 4.1 Hz, 1H), 3.52 (dd, J=10.3, 4.7 Hz, 1H), 3.39-3.24 (m, 4H), 3.07-2.99 (m, 1H), 2.89 (dd, J=13.8, 7.9 Hz, 1H), 2.28-2.21 (m, 1H), 2.12-2.06 (m, 1H), 1.84 (ddd, J=13.2, 11.2, 4.3 Hz, 1H), 1.49 (ddd, J=13.7, 10.1, 4.2 Hz, 1H), 1.28 (d, J=7.3 Hz, 3H), 1.2-1.11 (m, 1H), 0.88 (d, J=6.5 Hz, 3H), 0.82 (d, J=6.5 Hz, 3H); HRMS (ESI-TOF) m/z calcd. for C$_{37}$H$_{46}$N$_5$O$_5$ ([M+H]$^+$) 640.34935, found 640.35003.

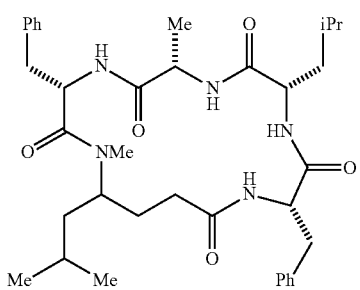

cyclo-[(Me)Aba(4-iBu)-Phe-Leu-Ala-Phe] (SEQ ID NO: 26)

Prepared following the general procedure outlined above using acryloyl-Phe-Leu-Ala-Phe-(Me)Leu (SEQ ID NO: 27) (6.8 mg, 10 μmol, 1.0 equiv.), Ir[dF(CF$_3$)ppy]$_2$(dtbbpy)PF$_6$ (1.3 mg, 1.2 μmol, 0.12 equiv.), K$_2$HPO$_4$ (3.5 mg, 20 μmol, 2.0 equiv.), and DMF (2.0 mL). After 10 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+ 0.1% formic acid over 12 minutes. Reaction yield was determined to be 77%, 1.6:1 dr. $^1$H NMR (500 MHz, CD$_3$OD) Major diastereomer: δ 7.32-7.16 (m, 10H), 4.82 (dt, J=9.3, 6.1 Hz, 1H), 4.69-4.62 (m, 1H), 4.54 (tt, J=11.0, 4.1 Hz, 1H), 4.17 (p, J=6.9 Hz, 1H), 3.98-3.91 (m, 1H), 3.08-3.03 (m, 2H), 2.92 (dd, J=13.6, 7.2 Hz, 1H), 2.62 (s, 3H), 2.23-2.08 (m, 2H), 1.85-1.73 (m, 2H), 1.57 (ddd, J=14.2, 9.9, 4.7 Hz, 1H), 1.44-1.32 (m, 4H), 1.32-1.25 (m, 1H), 1.20 (tt, J=11.1, 6.1 Hz, 1H), 1.02-0.94 (m, 1H), 0.93-0.72 (m, 14H); Minor diastereomer: δ 7.34-7.15 (m, 10H), 4.49 (q, J=6.8 Hz, 1H), 4.32 (q, J=7.1, 6.0 Hz, 2H), 4.00 (t, J=7.5 Hz, 1H), 3.89 (dd, J=11.2, 4.3 Hz, 1H), 3.24-3.15 (m, 1H), 3.08 (d, J=8.0 Hz, 2H), 2.98-2.91 (m, 1H), 2.67 (s, 3H), 2.33 (dd, J=15.8, 7.6 Hz, 1H), 2.15 (dd, J=15.8, 9.8 Hz, 1H), 1.95-1.84 (m, 1H), 1.78 (td, J=13.0, 11.3, 4.4 Hz, 1H), 1.63 (ddd, J=14.4, 10.3, 4.7 Hz, 2H), 1.41 (d, J=7.0 Hz, 3H), 1.40-1.19 (m, 4H), 0.93-0.77 (m, 12H); HRMS (ESI-TOF) m/z calcd. for C$_{36}$H$_{52}$N$_5$O$_5$ ([M+H]$^+$) 634.39630 found 634.39733.

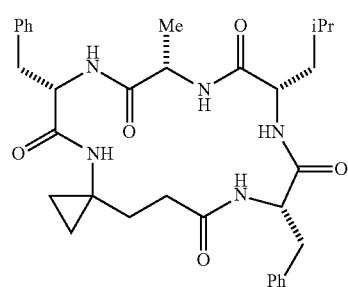

cyclo[(3-Ac)pa-Phe-Leu-Ala-Phe] (SEQ ID NO: 28)

Prepared following the general procedure outlined above using acryloyl-Phe-Leu-Ala-Phe-Acc (SEQ ID NO: 29) (6.3 mg, 10 μmol, 1.0 equiv.), Ir[dF(CF$_3$)ppy]$_2$(dtbbpy)PF$_6$ (1.3 mg, 1.2 μmol, 0.12 equiv.), K$_2$HPO$_4$ (3.5 mg, 20 μmol, 2.0 equiv.), and DMSO (4.0 mL). After 12 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+ 0.1% formic acid over 12 minutes. Reaction yield was determined to be 48%. $^1$H NMR (500 MHz, CD$_3$OD) δ 7.33-7.19 (m, 10H), 4.70 (t, J=7.9 Hz, 1H), 4.09 (dd, J=9.4, 6.3 Hz, 1H), 3.84 (q, J=7.3 Hz, 1H), 3.75 (dd, J=11.3, 4.2 Hz, 1H), 3.07 (dd, J=13.7, 8.2 Hz, 1H), 2.97 (dd, J=13.7, 7.5 Hz, 1H), 2.34-2.28 (m, 1H), 2.05 (d, J=14.3 Hz, 1H), 1.95-1.81 (m, 2H), 1.43 (ddd, J=13.7, 10.0, 4.3 Hz, 1H), 1.34-1.16 (m, 6H), 0.98-0.92 (m, 2H), 0.91 (d, J=6.6 Hz, 3H), 0.83 (d, J=6.5 Hz, 3H), 0.72 (ddd, J=10.6, 6.2, 4.4 Hz, 1H), 0.67-0.54 (m, 2H); HRMS (ESI-TOF) m/z calcd. for C$_{33}$H$_{44}$N$_5$O$_5$ ([M+H]$^+$) 590.33370, found 590.33304.

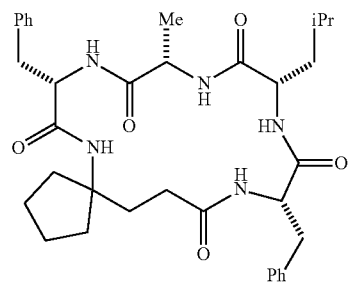

cyclo[(3-Acp)pa-Phe-Leu-Ala-Phe] (SEQ ID NO: 30)

Prepared following the general procedure outlined above using acryloyl-Phe-Leu-Ala-Phe-Acpc (SEQ ID NO: 31) (6.6 mg, 10 μmol, 1.0 equiv.), Ir[dF(CF$_3$)ppy]$_2$(dtbbpy)PF$_6$ (1.3 mg, 1.2 μmol, 0.12 equiv.), K$_2$HPO$_4$ (3.5 mg, 20 μmol, 2.0 equiv.), and DMSO (4.0 mL). After 12 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+ 0.1% formic acid over 12 minutes. Reaction yield was determined to be 49%. $^1$H NMR (500 MHz, CD$_3$OD) δ 7.33-7.18 (m, 10H), 4.65 (t, J=7.8 Hz, 1H), 4.16 (dd, J=11.1, 4.7 Hz, 1H), 3.94 (q, J=7.2 Hz, 1H), 3.68 (dd, J=11.4, 4.1 Hz, 1H), 3.31-3.27 (m, 1H), 3.22 (dd, J=13.9, 11.2 Hz, 1H), 3.07-2.96 (m, 2H), 2.36-2.28 (m, 2H), 2.27-2.16 (m, 2H), 2.15-2.09 (m, 1H), 2.09-2.02 (m, 1H), 1.90 (ddd, J=13.3, 11.3, 4.2 Hz, 1H), 1.83-1.73 (m, 1H), 1.64-1.51 (m, 3H), 1.51-1.41 (m, 3H), 1.27 (d, J=7.3 Hz, 3H), 1.19-1.09 (m, 1H), 0.89 (d, J=6.5 Hz, 3H), 0.79 (d, J=6.4 Hz, 3H); HRMS (ESI-TOF) m/z calcd. for C$_{35}$H$_{47}$N$_5$O$_5$ ([M+H]$^+$) 618.36500, found 618.36465.

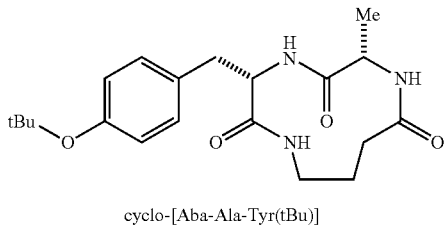

cyclo-[Aba-Ala-Tyr(tBu)]

Prepared following the general procedure outlined above using acryloyl-Ala-Tyr(tBu)-Gly (0.42 mg, 1 μmol, 1.0 equiv.), Ir[dF(CF$_3$)ppy]$_2$(dtbbpy)PF$_6$ (0.22 mg, 0.2 μmol, 0.20 equiv.), K$_2$HPO$_4$ (0.35 mg, 2.0 μmol, 2.0 equiv.), 2, 4, 6-triisopropylbenzenethiol (0.024 mg, 0.1 μmol, 0.1 equiv.), and DMF (1.0 mL). After 12 h, the reaction mixture was removed from LED irradiation and concentrated. The residue was then dissolved in 100 μL DMF, centrifuged, and subjected to HPLC analysis. Conditions: Vydac 218TP C18 5μ, length 150 mm, ID 4.6 mm, 10-50% MeCN/H$_2$O+0.1% formic acid over 12 minutes. Reaction yield was determined to be 24%. $^1$H NMR (500 MHz, CD$_3$OD) δ 7.21 (d, J=8.0 Hz, 2H), 6.93 (d, J=7.6 Hz, 3H), 4.68 (br s, 1H), 4.03 (br s, 1H), 3.80 (br s, 1H), 3.02-2.86 (m, 2H), 2.86-2.79 (m, 1H), 2.26-2.17 (m, 1H), 2.19-2.04 (m, 2H), 1.83-1.73 (m, 1H), 1.32 (s, 9H), 1.13 (d, J=6.5 Hz, 3H); HRMS (ESI-TOF) m/z calcd. for C$_{20}$H$_{30}$N$_3$O$_4$ ([M+H]$^+$) 376.22308, found 376.22297.

(SEQ ID NO: 32)

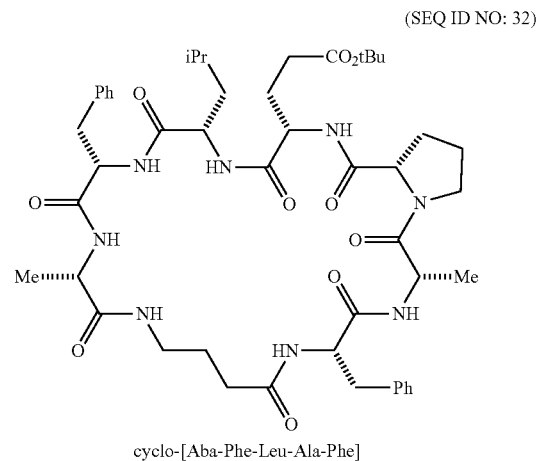

cyclo-[Aba-Phe-Leu-Ala-Phe]

Prepared following the general procedure outlined above using acryloyl-Phe-Ala-Pro-Glu(OtBu)-Leu-Phe-Ala-Gly (SEQ ID NO: 33) (9.6 mg, 10 μmol, 1.0 equiv.), Ir[dF(CF$_3$)ppy]$_2$(dtbbpy)PF$_6$ (0.9 mg, 0.8 μmol, 0.08 equiv.), K$_2$HPO$_4$ (3.5 mg, 20 μmol, 2.0 equiv.), and DMF (2.0 mL). After 10 h, the reaction mixture was removed from LED irradiation, centrifuged, and subjected to HPLC analysis. Conditions: Vydac 218TP C18 5μ, length 150 mm, ID 4.6 mm, 40-80% MeCN/H$_2$O+0.1% formic acid over 12 minutes. Reaction yield was determined to be 61%. $^1$H NMR (500 MHz, CD$_3$OD) δ 7.31-7.15 (m, 10H), 4.70 (dt, J=10.6, 3.0 Hz, 1H), 4.61 (d, J=9.1 Hz, 1H), 4.52 (t, J=7.4 Hz, 1H), 4.40-4.30 (m, 1H), 4.15-4.06 (m, 1H), 4.04-3.98 (m, 1H), 3.63 (br s, 1H), 3.60-3.48 (m, 1H), 3.42-3.35 (m, 1H), 3.23-3.08 (m, 1H), 3.04 (q, J=6.8 Hz, 1H), 2.91 (br s, 1H), 2.87-2.72 (m, 1H), 2.54-2.48 (m, 1H), 2.46-2.37 (m, 1H), 2.36-2.14 (m, 3H), 2.13-1.72 (m, 8H), 1.66 (t, J=12.6 Hz, 1H), 1.54-1.43 (m, 9H), 1.39-1.24 (m, 8H), 0.96-0.77 (m, 6H); HRMS (ESI-TOF) m/z calcd. for C$_{48}$H$_{69}$N$_8$O$_{10}$ ([M+H]$^+$) 917.51312, found 917.51229.

(SEQ ID NO: 34)

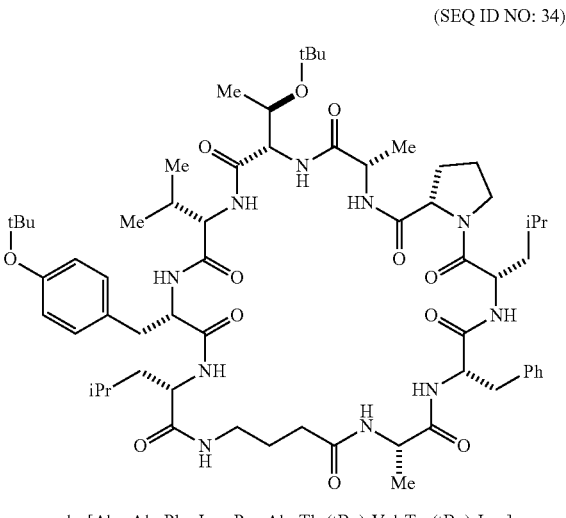

cyclo-[Aba-Ala-Phe-Leu-Pro-Ala-Thr(tBu)-Val-Tyr(tBu)-Leu]

Prepared following the general procedure outlined above using acryloyl-Ala-Phe-Leu-Pro-Ala-Thr(tBu)-Val-Tyr(tBu)-Leu-Gly (SEQ ID NO: 35) (3.1 mg, 2.5 μmol, 1.0 equiv.), Ir[dF(CF₃)ppy]₂(dtbbpy)PF₆ (0.33 mg, 0.3 µmol, 0.12 equiv.), K₂HPO₄ (0.88 mg, 5 µmol, 2.0 equiv.), and DMF (1.0 mL). After 20 h, the reaction mixture was removed from LED irradiation, centrifuged, and subjected to HPLC analysis. Conditions: Vydac 218TP C18 5µ, length 150 mm, ID 4.6 mm, 40-80% MeCN/H₂O+0.1% formic acid over 12 minutes. Reaction yield was determined to be 64% (n=2). ¹H NMR (500 MHz, CD₃OD) NMR spectrum is complicated by the presence of rotamers. δ 7.29-7.19 (m, 5H), 7.18-7.14 (m, 2H), 6.87 (d, J=8.4 Hz, 2H), 4.82 (q, J=7.2 Hz, 1H), 4.71 (q, J=7.7 Hz, 1H), 4.68-4.62 (m, 1H), 4.58-4.47 (m, 1H), 4.39 (t, J=7.1 Hz, 1H), 4.34 (t, J=4.6 Hz, 1H), 4.32-4.24 (m, 2H), 4.12 (q, J=7.0 Hz, 1H), 3.81-3.74 (m, 1H), 3.66 (q, J=9.3, 8.6 Hz, 1H), 3.46 (dt, J=9.9, 6.9 Hz, 1H), 3.17 (ddd, J=13.5, 7.7, 5.1 Hz, 2H), 3.03-2.88 (m, 2H), 2.45-2.35 (m, 1H), 2.28 (ddd, J=15.4, 9.8, 6.7 Hz, 2H), 2.15 (ddd, J=14.0, 9.9, 5.6 Hz, 2H), 1.99 (tt, J=14.4, 6.7 Hz, 3H), 1.94-1.76 (m, 3H), 1.76-1.61 (m, 4H), 1.59 (t, J=7.1 Hz, 2H), 1.46 (d, J=7.2 Hz, 2H), 1.31 (s, 9H), 1.29 (s, 9H), 1.04-0.86 (m, 18H), 0.82 (dd, J=16.3, 6.7 Hz, 6H); HRMS (ESI-TOF) m/z calcd. for C₆₂H₉₇N₁₀O₁₂ ([M+H]⁺) 1173.72820, found 1173.72778.

(SEQ ID NO: 36)

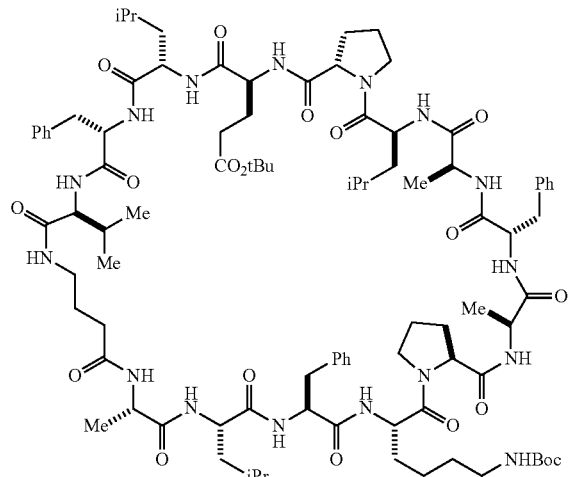

cyclo-[Aba-Ala-Leu-Phe-Lys(Boc)-Pro-Ala-Phe-Ala-Leu-Pro-Glu(OtBu)-Leu-Phe-Val]

Prepared following the general procedure outlined above using acryloyl-Ala-Leu-Phe-Lys(Boc)-Pro-Ala-Phe-Ala-Leu-Pro-Glu(OtBu)-Leu-Phe-Val-Gly (SEQ ID NO: 37) (1.83 mg, 1 µmol, 1.0 equiv.), Ir[dF(CF₃)ppy]₂(dtbbpy)PF₆ (0.22 mg, 0.2 µmol, 0.2 equiv.), K₂HPO₄ (0.35 mg, 2.0 µmol, 2.0 equiv.), and DMF (4.0 mL). After 20 h, the reaction mixture was removed from LED irradiation, centrifuged, and subjected to HPLC analysis. Conditions: Vydac 218TP C18 5µ, length 150 mm, ID 4.6 mm, 40-80% MeCN/H₂O+0.1% formic acid over 12 minutes. Reaction yield was determined to be 60%. ¹H NMR (500 MHz, CD₃OD) δ 7.37-7.02 (15H), 4.76 (1H), 4.74 (1H), 4.71 (1H), 4.68 (1H), 4.64 (1H), 4.49 (1H), 4.44 (1H), 4.36 (1H), 4.34 (1H), 4.23 (1H), 4.04 (1H), 3.93 (1H), 3.86 (1H), 3.77 (1H), 3.65 (2H), 3.50 (2H), 3.16 (2H), 3.07 (2H), 2.93 (2H), 2.68-2.60 (2H), 2.40 (1H), 2.31 (1H), 2.14 (1H), 2.09 (2H), 2.02 (1H), 1.98 (2H), 1.90 (2H), 1.88 (2H), 1.84 (2H), 1.83-1.75 (2H), 1.77 (3H), 1.65 (2H), 1.63 (2H), 1.56 (2H), 1.51 (2H), 1.46 (2H), 1.45 (9H), 1.44 (4H), 1.39 (9H), 1.35 (3H), 1.28 (3H), 1.23 (3H), 0.99 (6H), 0.97 (6H), 0.91 (6H), 0.85 (6H); HRMS (ESI-TOF) m/z calcd. for C₉₃H₁₄₂N₁₆O₁₉ ([M+2H]²⁺) 893.53187, found 893.53163.

General Procedure for Decarboxylative Conjugate Coupling

Commercial reagents were purchased from Sigma Aldrich and purified prior to use following the guidelines of Perrin and Armarego, *Purification of Laboratory Chemicals,* Pergamon, Oxford, ed.3 1988) (hereinafter "Perrin"). All solvents were purified by passage through columns of activated alumina. Organic solutions were concentrated under reduced pressure on a Büchi rotary evaporator using an acetone-dry ice bath for volatile compounds. Chromatographic purification of products was accomplished by flash chromatography on silica gel (Fluka, 230-400 mesh). Thin layer chromatography (TLC) was performed on Analtech Uniplate 250 m silica gel plates. Visualization of the developed chromatogram was performed by fluorescence quenching, p-anisaldehyde, potassium permanganate, or ceric ammonium molybdate stain. ¹H and ¹³C NMR spectra were recorded on a Bruker 500 (500 and 125 MHz) instrument, and are internally referenced to residual protio solvent signals (note: CDCl₃ referenced at 7.26 and 77.0 ppm respectively). Data for ¹H NMR are reported as follows: chemical shift (δ ppm), integration, multiplicity (s=singlet, d=doublet, t=triplet, q=quartet, m=multiplet), coupling constant (Hz) and assignment. Data for ¹³C NMR are reported in terms of chemical shift and no special nomenclature is used for equivalent carbons. High resolution mass spectra were obtained at Princeton University mass spectrometry facilities. All amino acids were used from commercial suppliers. All aryl and heteroaryl halides were used from commercial suppliers or prepared using standard literature procedures.

An oven-dried 8 mL vial equipped with a Teflon septum and magnetic stir bar was charged with Ir[dF(CF₃)ppy]2(dtbbpy)PF₆ (2 µmol, 0.01 equiv), Cbz-Pro-OH (0.2 mmol, 1.0 equiv), diethyl ethylidenemalonate (0.2 mmol, 1.0 equiv), K₂HPO₄ (0.24 mmol, 1.2 equiv), and 0.5 mL of DMF. The reaction mixture was degassed by bubbling nitrogen stream for 15 min, then irradiated with a 26 W fluorescent lamp (at approximately 2 cm away from the light source). After 36 h, the reaction mixture was diluted with saturated aqueous NaHCO₃ solution, extracted with Et₂O (3×50 mL). The combined organic extracts were washed with water and brine, dried over MgSO₄ and concentrated in vacuo. Purification of the crude product by flash chromatography on silica gel using the indicated solvent system afforded the desired product.

(±)-Benzyl 2-(3-oxocyclopentyl)pyrrolidine-1-carboxylate: According to the general procedure, Ir[dF(CF₃)ppy)]2 (dtbbpy)PF₆ (2.2 mg, 2 µmol, 0.01 equiv.), Cbz-Pro-OH (50.0 mg, 0.2 mmol, 1.0 equiv), 2-cyclopenten-1-one (16.4 mg, 0.2 mmol, 1.0 equiv), K₂HPO₄ (42.0 mg, 0.24 mmol, 1.2 equiv), and 0.5 mL of DMF were used. The product was isolated by flash chromatography (20% ethyl acetate/hexane) as a pale yellow oil (51 mg, 88%). ¹H NMR (500 MHz, CDCl₃) mixture of diastereomers and rotamers: δ 7.37-7.30 (m, 5H), 5.16-5.10 (m, 2H), 4.06-3.96 (m, 1H), 3.62-3.52 (m, 1H), 3.38 (br, 1H), 2.35-1.79 (m, 10H), 1.69-1.64 (m, 1H); ¹³C NMR (125 MHz, CDCl₃) mixture of diastereomers and rotamers: δ 218.79, 218.42, 155.93, 155.85, 155.62, 155.45, 136.97, 136.55, 128.57, 128.41, 128.25, 128.02, 127.84, 67.22, 66.82, 60.90, 60.76, 60.27, 60.18, 46.75, 46.66, 42.84, 42.08, 41.65, 41.46, 41.35, 38.70, 38.52, 38.34, 29.49, 28.88, 28.54, 28.13, 26.82, 26.12, 24.04, 23.96, 23.12, 23.04; HRMS (ESI) m/z calcd for C₁₇H₂₂NO₃ [(M+H)⁺] 288.1600, found 288.1609. IR (film) 2961, 1738, 1693, 1405, 1102, 698 cm⁻¹;

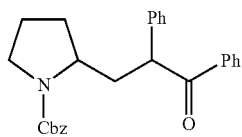 [SMILES: O=C(c1ccccc1)C(CC1CCCN1C(=O)OCc1ccccc1)c1ccccc1]

(±)-Benzyl 2-(3-oxo-2,3-diphenylpropyl)pyrrolidine-1-carboxylate: According to the general procedure, Ir[dF(CF₃)ppy)]₂(dtbbpy)PF₆ (2.2 mg, 2 μmol, 0.01 equiv.), Cbz-Pro-OH (49.9 mg, 0.2 mmol, 1.0 equiv.), CsF (36.5 mg, 0.24 mmol, 1.2 equiv.), 1,2-diphenylprop-2-en-1-one (41.7 mg, 0.2 mmol, 1.0 equiv.) and DMF (0.5 mL) were used. The product was isolated by flash chromatography (30% ethyl acetate in hexanes) as a colourless powder (67 mg, 81%). ¹H NMR (500 MHz, CDCl₃) mixture of diastereomers and rotamers: δ 8.06-7.84 (m, 2H), 7.50-7.14 (m, 13H), 5.20-5.03 (m, 1.2H), 5.03-4.90 (m, 0.6H), 4.82-4.75 (m, 0.2H), 4.74-4.67 (m, 0.2H), 4.67-4.58 (m, 0.6H), 4.41 (d, J=12.5 Hz, 0.2H), 4.26-4.18 (m, 0.4H), 4.05-3.94 (m, 0.35H), 3.94-3.85 (m, 0.25H), 3.55-3.20 (m, 2H), 2.79-2.67 (m, 0.5H), 2.41-2.32 (m, 0.15H), 2.30-2.21 (m, 0.2H), 2.21-1.71 (m, 4.5H), 1.55-1.44 (m, 0.65H); ¹³C NMR (125 MHz, CDCl₃) mixture of diastereomers and rotamers: δ 199.40, 199.15, 198.95, 198.57, 155.43, 155.28, 154.93, 139.86, 139.70, 139.52, 139.31, 137.28, 136.87, 136.79, 136.60, 136.46, 136.40, 132.87, 132.73, 132.60, 129.05, 128.96, 128.88, 128.77, 128.63, 128.52, 128.47, 128.38, 128.24, 128.14, 128.06, 127.86, 127.81, 127.69, 127.11, 126.99, 66.86, 66.53, 66.48, 56.49, 56.20, 55.64, 51.09, 50.89, 50.39, 46.45, 46.25, 45.76, 40.15, 39.58, 39.05, 31.77, 31.41, 31.26, 30.99, 23.83, 23.55, 22.90; HRMS (ESI) m z calcd for C₂₇H₂₈NO₃ [(M+H)⁺] 414.20637, found 414.20623. IR (film) 2958, 1686, 1407, 1353, 1206, 1177, 1096, 953, 747, 694 cm⁻¹;

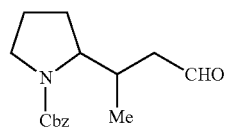 [SMILES: CC(CC=O)C1CCCN1C(=O)OCc1ccccc1]

(±)-Benzyl 2-(4-oxobutan-2-yl)pyrrolidine-1-carboxylate: According to the general procedure, Ir[dF(CF₃)ppy)]2(dtbbpy)PF₆ (11 mg, 10.0 μmol, 0.01 equiv), Cbz-Pro-OH (250.0 mg, 1.0 mmol, 1.0 equiv), crotonaldehyde (70.9 mg, 1.0 mmol, 1.0 equiv), K₂HPO₄ (210.0 mg, 1.2 mmol, 1.2 equiv), and 2.5 mL of DMF were used. The product was isolated by flash chromatography (20% ethyl acetate/hexane) as a pale yellow oil (253 mg, 92%). ¹H NMR (500 MHz, CDCl₃) mixture of diastereomers and rotamers: δ 9.70 (br, 0.3H), 9.59-9.57 (m, 0.5H), 9.50 (m, 0.2H), 7.37-7.30 (m, 5H), 5.16-5.09 (m, 2H), 3.90 (br, 0.55H), 3.81 (br, 0.45H), 3.65-3.48 (m, 1H), 3.31-3.26 (m, 0.45H), 3.22-3.17 (m, 0.55H), 2.95 (br, 0.3H), 2.69 (br, 0.2H), 2.59-2.49 (m, 0.6H), 2.39-2.34 (m, 0.6H), 2.26-2.11 (m, 0.9H), 1.93-1.63 (m, 4.4H), 0.96-0.86 (m, 3H); ¹³C NMR (125 MHz, CDCl₃) mixture of diastereomers and rotamers: δ 202.10, 201.83, 201.61, 201.42, 155.43, 155.38, 155.16, 136.78, 136.52, 128.32, 127.93, 127.76, 127.60, 66.87, 66.54, 61.91, 61.66, 61.00, 47.93, 47.66, 47.20, 47.08, 46.61, 46.16, 45.77, 31.06, 30.98, 30.96, 30.37, 27.19, 26.82, 25.79, 24.18, 23.85, 23.55, 23.24, 16.91, 15.68, 15.25; HRMS (ESI) m/z calcd for C₁₆H₂₁NNaO₃ [(M+Na)⁺] 298.1419, found 298.1422. IR (film) 2962, 1692, 1404, 1097, 697 cm⁻¹;

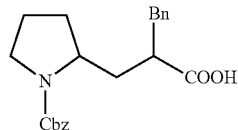

(±)-2-Benzyl-3-(1-((benzyloxy)carbonyl)pyrrolidin-2-yl)propanoic acid: According to the general procedure, Ir[dF(CF₃)ppy)]2(dtbbpy)PF₆ (2.2 mg, 2 μmol, 0.01 equiv.), Cbz-Pro-OH (50.0 mg, 0.2 mmol, 1.0 equiv), 2-benzylacrylic acid (32.4 mg, 0.2 mmol, 1.0 equiv), K₂HPO₄ (42.0 mg, 0.24 mmol, 1.2 equiv), and 0.5 mL of DMF were used. The product was isolated by flash chromatography (50% ethyl acetate/hexane) as a pale yellow solid (42 mg, 57%). ¹H NMR (500 MHz, CDCl₃) mixture of diastereomers and rotamers: δ 7.41-7.08 (m, 10H), 5.23-5.01 (m, 2H), 4.16-4.12 (m, 0.6H), 3.98-3.92 (m, 0.4H), 3.46-3.42 (m, 1H), 3.32-3.27 (m, 1H), 3.12-2.60 (m, 3H), 2.20-1.53 (m, 6H); ¹³C NMR (125 MHz, CDCl₃) mixture of diastereomers and rotamers: δ 179.80, 179.56, 177.13, 157.21, 155.39, 155.22, 139.26, 139.05, 138.75, 138.70, 136.90, 136.36, 129.37, 129.16, 129.04, 128.96, 128.71, 128.57, 128.53, 128.42, 128.34, 128.17, 128.04, 127.97, 126.62, 126.53, 126.45, 67.82, 67.11, 66.97, 56.24, 55.93, 55.63, 46.66, 46.45, 46.28, 44.89, 44.58, 44.43, 38.85, 38.56, 38.42, 36.75, 36.37, 36.04, 31.53, 31.24, 30.82, 30.40, 29.83, 23.71, 23.47, 23.16, 22.93; HRMS (ESI) m/z calcd for C₂₂H₂₆NO₄ [(M+H)⁺] 368.1862, found 368.1868. IR (film) 2957, 1700, 1419, 1105, 698 cm⁻¹;

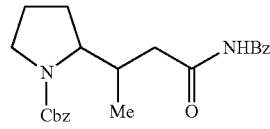

(±)-Benzyl 2-(4-benzamido-4-oxobutan-2-yl)pyrrolidine-1-carboxylate: According to the general procedure, Ir[dF(CF₃)ppy)]2(dtbbpy)PF₆ (2.2 mg, 2 μmol, 0.01 equiv.), Cbz-Pro-OH (50.0 mg, 0.2 mmol, 1.0 equiv), (E)-N-(but-2-enoyl)benzamide (37.8 mg, 0.2 mmol, 1.0 equiv), K₂HPO₄ (42.0 mg, 0.24 mmol, 1.2 equiv), and 0.5 mL of DMF were used. The product was isolated by flash chromatography (30% ethyl acetate/hexane) as a pale yellow solid (67 mg, 85%). ¹H NMR (500 MHz, CDCl₃) mixture of diastereomers and rotamers: δ 9.41 (s, 0.2H), 9.03 (s, 0.4H), 8.45 (s, 0.14H), 8.39 (m, 0.26H), 7.91-7.78 (m, 2H), 7.62-7.56 (m, 1H), 7.51-7.45 (m, 2H), 7.37-7.22 (m, 5H), 5.16-5.00 (m, 2H), 4.04 (br, 0.2H), 3.92-3.91 (m, 0.8H), 3.68-3.59 (m, 0.6H), 3.55-3.50 (m, 0.4H), 3.36-3.29 (m, 1H), 3.09-2.88 (m, 1H), 2.81-2.68 (m, 1H), 2.61-2.49 (m, 1H), 2.00-1.73 (m, 4H), 1.02-0.93 (m, 3H); ¹³C NMR (125 MHz, CDCl₃) mixture of diastereomers and rotamers: δ 175.46, 175.21, 174.58, 174.23, 165.63, 165.57, 156.11, 155.93, 155.76, 155.57, 136.98, 136.89, 133.25, 133.03, 129.02, 128.86, 128.57, 128.52, 128.46, 128.12, 127.96, 127.84, 127.77, 67.00, 66.91, 66.81, 62.15, 61.37, 61.32, 47.83, 47.32, 46.80, 41.74, 41.40, 40.01, 34.02, 32.73, 32.50, 27.82, 27.71, 27.45, 24.42, 24.02, 23.77, 23.51, 17.00, 16.59, 15.84, 15.60; HRMS (ESI) m/z calcd for $C_{23}H_{27}N_2O_4$ [(M+H)$^+$] 395.1971, found 395.1961. IR (film) 2964, 1686, 1411, 1242, 1102, 705 cm$^{-1}$;

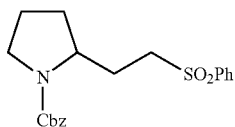

(±)-Benzyl 2-(2-(phenylsulfonyl)ethyl)pyrrolidine-1-carboxylate: According to the general procedure, Ir[dF(CF$_3$)ppy)]$_2$(dtbbpy)PF$_6$ (2.2 mg, 2 µmol, 0.01 equiv.), Cbz-Pro-OH (50.0 mg, 0.2 mmol, 1.0 equiv), phenyl vinylsulfone (33.6 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (50% ethyl acetate/hexane) as a pale yellow solid (52 mg, 69%). $^1$H NMR (500 MHz, CDCl$_3$) mixture of diastereomers and rotamers: δ 7.90 (d, J=7.5 Hz, 1H), 7.83 (d, J=7.0 Hz, 1H), 7.65 (t, J=7.5 Hz, 1H), 7.57-7.52 (m, 2H), 7.33-7.30 (m, 4H), 7.26-7.22 (m, 1H), 5.09-5.04 (m, 2H), 3.96-3.89 (m, 1H), 3.49-3.35 (m, 2H), 3.20 (d, J=8.0 Hz, 1H), 3.03-3.02 (m, 1H), 2.09-1.94 (m, 2H), 1.90-1.82 (m, 3H), 1.65-1.62 (m, 1H); $^{13}$C NMR (125 MHz, CDCl$_3$) mixture of diastereomers and rotamers: δ 155.47, 155.00, 139.20, 139.02, 136.81, 136.39, 133.78, 129.37, 128.64, 128.57, 128.22, 128.10, 128.06, 127.87, 67.20, 66.85, 56.49, 55.87, 53.93, 53.60, 46.87, 46.48, 31.14, 30.68, 27.90, 27.83, 23.75, 23.02; HRMS (ESI) m/z calcd for $C_{20}H_{24}NO_4S$ [(M+H)$^+$] 374.1426, found 374.1431. IR (film) 2956, 1691, 1408, 1304, 1143, 1086, 742 cm$^{-1}$;

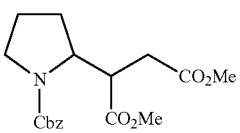 [SMILES: COC(=O)CC(C(=O)OC)C1CCCN1C(=O)OCc1ccccc1]

(±)-Diethyl 2-(1-(1-benzoylpyrrolidin-2-yl)ethyl)malonate: According to the general procedure, Ir[dF(CF$_3$)ppy)]$_2$(dtbbpy)PF$_6$ (2.2 mg, 2 µmol, 0.01 equiv.), Cbz-Pro-OH (50.0 mg, 0.2 mmol, 1.0 equiv), dimethyl maleate (28.8 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (25% ethyl acetate/hexane) as a pale yellow oil (65 mg, 93%). $^1$H NMR (500 MHz, CDCl$_3$) mixture of diastereomers and rotamers: δ 7.41-7.29 (m, 5H), 5.21-5.08 (m, 2H), 4.31-4.28 (m, 0.55H), 4.17-4.09 (m, 0.45H), 3.69-3.64 (m, 6.8H), 3.56-3.47 (m, 0.8H), 3.37-3.33 (m, 0.8H), 3.28-3.22 (m, 0.6H), 2.81-2.70 (m, 1H), 2.54-2.29 (m, 1H), 1.95-1.72 (m, 4H); $^{13}$C NMR (125 MHz, CDCl$_3$) mixture of diastereomers and rotamers: δ 173.60, 173.27, 173.03, 172.37, 172.30, 172.14, 155.40, 155.03, 136.89, 136.77, 136.56, 128.52, 128.22, 128.08, 128.03, 127.99, 127.86, 67.22, 66.86, 59.02, 58.35, 58.24, 57.42, 52.13, 52.11, 51.92, 51.86, 47.79, 47.19, 46.96, 46.60, 44.57, 44.31, 44.13, 43.65, 33.60, 31.15, 30.54, 28.14, 28.10, 27.42, 24.17, 23.64, 23.57, 22.85; HRMS (ESI) m/z calcd for $C_{18}H_{24}NO_6$ [(M+H)$^+$] 350.1604, found 350.1600. IR (film) 2953, 1697, 1732, 1408, 1165, 1110, 699 cm$^{-1}$;

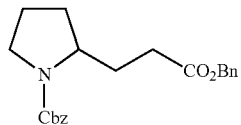

(±)-Benzyl 2-(3-(benzyloxy)-3-oxopropyl)pyrrolidine-1-carboxylate: According to the general procedure, Ir[dF(CF$_3$)ppy)]$_2$(dtbbpy)PF$_6$ (2.2 mg, 2 µmol, 0.01 equiv.), Cbz-Pro-OH (49.9 mg, 0.2 mmol, 1.0 equiv.), benzyl acrylate (32.4 mg, 0.2 mmol, 1.0 equiv.), K$_2$HPO$_4$ (41.8 mg, 0.24 mmol, 1.2 equiv.) and DMF (0.5 mL) were used. The product was isolated by flash chromatography (30% ethyl acetate in hexanes) as a colorless oil (55 mg, 75%). $^1$H NMR (500 MHz, CDCl$_3$) mixture of rotamers: δ 7.31-7.19 (m, 10H), 5.08-4.94 (m, 4H), 3.89-3.80 (m, 1H), 3.46-3.26 (m, 2H), 2.40-2.22 (m, 2H), 2.05-1.95 (m, 0.5H), 1.95-1.62 (m, 4.5H), 1.60-1.50 (m, 1H); $^{13}$C NMR (125 MHz, CDCl$_3$) mixture of rotamers: δ 173.25, 173.03, 155.14, 137.03, 136.84, 136.01, 135.94, 128.54, 128.46, 128.26, 128.20, 127.97, 127.88, 127.85, 66.84, 66.59, 66.28, 57.25, 56.54, 46.65, 46.32, 31.36, 31.17, 30.75, 30.05, 29.80, 29.44, 23.77, 23.00; HRMS (ESI) m/z calcd for $C_{22}H_{26}NO_4$ [(M+H)$^+$] 368.18563, found 368.18568. IR (film) 2957, 1733, 1695, 1455, 1409, 1355, 1165, 1151, 1098, 743, 697 cm$^{-1}$;

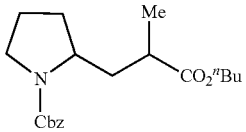

(±)-Benzyl 2-(3-butoxy-2-methyl-3-oxopropyl)pyrrolidine-1-carboxylate: According to the general procedure, Ir[dF(CF$_3$)ppy)]$_2$(dtbbpy)PF$_6$ (2.2 mg, 2 µmol, 0.01 equiv.), Cbz-Pro-OH (50.0 mg, 0.2 mmol, 1.0 equiv), butyl methacrylate (28.4 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (20% ethyl acetate/hexane) as a pale yellow oil (48 mg, 69%). $^1$H NMR (500 MHz, CDCl$_3$) mixture of diastereomers and rotamers: δ 7.39-7.26 (m, 5H), 5.18-5.07 (m, 2H), 4.06-3.91 (m, 3H), 3.49-3.33 (m, 2H), 2.56-2.38 (m, 1H), 2.18-1.60 (m, 6H), 1.39-1.31 (m, 3H), 1.24-1.20 (m, 1.4H), 1.10-1.09 (m, 2H), 0.95-0.90 (m, 3.6H); $^{13}$C NMR (125 MHz, CDCl$_3$) mixture of diastereomers and rotamers: δ 176.76, 176.38, 155.28, 155.02, 154.69, 137.25, 137.17, 136.94, 128.55, 128.53, 128.29, 128.07, 128.01, 127.96, 127.94, 127.93, 127.83, 66.95, 66.91, 66.90, 66.65, 66.61, 64.65, 64.33, 64.31, 55.92, 55.45, 46.57, 46.45, 46.28, 46.26, 46.20, 38.98, 38.52, 37.49, 37.17, 30.73, 30.71, 30.69, 30.57, 23.89, 23.81, 22.99, 19.37, 19.25, 19.24, 17.95, 17.80, 13.89, 13.86, 13.85; HRMS (ESI) m/z calcd for $C_{20}H_{30}NO_4$ [(M+H)$^+$] 348.2175, found 348.2183. IR (film) 2959, 1698, 1408, 1110, 697 cm$^{-1}$;

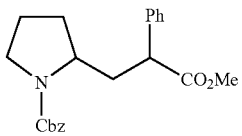 [SMILES: COC(=O)C(CC1CCCN1C(=O)OCc1ccccc1)c1ccccc1]

(±)-Benzyl 2-(3-methoxy-3-oxo-2-phenylpropyl)pyrrolidine-1-carboxylate: According to the general procedure, Ir[dF(CF$_3$)ppy)]$_2$(dtbbpy)PF$_6$ (2.2 mg, 10.0 μmol, 0.01 equiv), Cbz-Pro-OH (50.0 mg, 0.2 mmol, 1.0 equiv), methyl 2-phenylacrylate (32.4 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (20% ethyl acetate/hexane) as a pale yellow oil (65 mg, 89%). $^1$H NMR (500 MHz, CDCl$_3$) mixture of diastereomers and rotamers: δ 7.46-7.15 (m, 10H), 5.15-5.03 (m, 2H), 3.99-3.31 (s, 7H), 2.59-2.55 (br, 0.7H), 2.34-2.22 (m, 0.3H), 2.10-2.05 (m, 0.3H), 1.91-1.70 (m, 3.7H), 1.57-1.48 (m, 0.8H), 1.27-1.20 (m, 0.2H); $^{13}$C NMR (125 MHz, CDCl$_3$) mixture of diastereomers and rotamers: δ 174.25, 174.00, 173.91, 155.26, 155.12, 155.01, 139.40, 139.12, 138.57, 138.14, 137.04, 136.90, 136.82, 128.71, 128.53, 128.43, 128.38, 128.36, 128.06, 127.94, 127.84, 127.39, 127.31, 126.67, 67.04, 66.96, 66.65, 66.59, 56.52, 56.06, 55.97, 55.24, 56.52, 56.06, 55.97, 55.24, 52.14, 52.09, 48.97, 48.75, 46.60, 46.35, 46.05, 38.68, 38.60, 37.62, 37.24, 31.15, 30.80, 30.70, 30.15, 23.88, 23.72, 23.07, 22.90; HRMS (ESI) m/z calcd for C$_{22}$H$_{26}$NO$_4$ [(M+H)$^+$] 368.1862, found 368.1869. IR (film) 2952, 2693, 1408, 1097, 697 cm$^{-1}$;

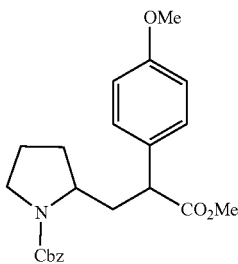 [SMILES: COC(=O)C(CC1CCCN1C(=O)OCc1ccccc1)c1ccc(OC)cc1]

(±)-Benzyl 2-(3-methoxy-2-(4-methoxyphenyl)-3-oxopropyl)pyrrolidine-1-carboxylate: According to the general procedure, Ir[dF(CF$_3$)ppy)]$_2$(dtbbpy)PF$_6$ (2.2 mg, 2 μmol, 0.01 equiv.), Cbz-Pro-OH (49.9 mg, 0.2 mmol, 1.0 equiv.), CsF (36.5 mg, 0.24 mmol, 1.2 equiv.), methyl 2-(4-methoxyphenyl)acrylate (38.4 mg, 0.2 mmol, 1.0 equiv.) and DMF (0.5 mL) were used. The product was isolated by flash chromatography (30% ethyl acetate in hexanes) as a colorless oil (60 mg, 76%). $^1$H NMR (500 MHz, CDCl$_3$) mixture of diastereomers and rotamers: δ 7.50-7.28 (m, 6H), 7.16 (d, J=7.5 Hz, 0.8H), 7.08 (d, J=7.5 Hz, 0.2H), 6.90-6.81 (m, 1.8H), 6.71 (d, J=8.5 Hz, 0.2H), 5.21-5.05 (m, 2H), 4.04-3.89 (m, 0.8H), 3.85-3.75 (m, 3.5H), 3.75-3.52 (m, 3.5H), 3.52-3.30 (m, 2.2H), 2.62-2.49 (m, 0.8H), 2.43-2.33 (m, 0.1H), 2.29-2.20 (m, 0.1H), 2.10-1.42 (m, 5H); $^{13}$C NMR (125 MHz, CDCl$_3$) mixture of diastereomers and rotamers: δ 174.48, 174.22, 174.15, 158.79, 155.20, 155.04, 154.99, 136.99, 136.86, 136.77, 131.36, 131.09, 129.03, 128.80, 128.00, 127.88, 127.78, 114.00, 66.97, 66.60, 56.43, 55.93, 55.26, 55.23, 55.10, 52.07, 52.00, 48.06, 47.81, 46.55, 46.29, 46.02, 38.69, 38.58, 37.36, 36.96, 31.20, 30.79, 30.53, 29.99, 23.84, 23.69, 23.03, 22.86; HRMS (ESI) m z calcd for C$_{23}$H$_{28}$NO$_5$ [(M+H)$^+$] 398.1962, found 398.19642. IR (film) 2952, 1731, 1694, 1511, 1409, 1351, 1248, 1178, 1161, 1097, 1032, 698 cm$^{-1}$;

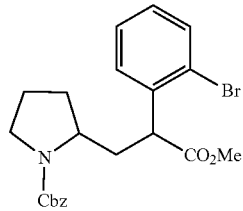 [SMILES: COC(=O)C(CC1CCCN1C(=O)OCc1ccccc1)c1ccccc1Br]

(±)-Benzyl 2-(2-(2-bromophenyl)-3-methoxy-3-oxopropyl)pyrrolidine-1-carboxylate: According to the general procedure, Ir[dF(CF$_3$)ppy)]$_2$(dtbbpy)PF$_6$ (2.2 mg, 2 μmol, 0.01 equiv.), Cbz-Pro-OH (49.9 mg, 0.20 mmol, 1.0 equiv.), K$_2$HPO$_4$ (41.8 mg, 0.24 mmol, 1.2 equiv.), methyl 2-(2-bromophenyl)acrylate (48.2 mg, 0.2 mmol, 1.0 equiv.) and DMF (0.5 mL) were used. The product was isolated by flash chromatography (30% ethyl acetate in hexanes) as a colorless oil (77 mg, 87%). $^1$H NMR (500 MHz, CDCl$_3$) mixture of diastereomers and rotamers: δ 7.60-7.53 (m, 1H), 7.52-7.25 (m, 6.5H), 7.18-6.98 (m, 1.5H), 5.23-5.03 (m, 2H), 4.37-4.20 (m, 1H), 4.12-4.03 (m, 0.65H), 3.90-3.83 (m, 0.16H), 3.77-3.75 (m, 0.19H), 3.74-3.55 (m, 3H), 3.54-3.33 (m, 2H), 2.71-2.62 (m, 0.3H), 2.57-2.47 (m, 0.3H), 2.37-2.28 (m, 0.2H), 2.23-2.16 (m, 0.2H), 2.12-1.60 (m, 5H); $^{13}$C NMR (125 MHz, CDCl$_3$) mixture of diastereomers and rotamers: δ 173.61, 173.45, 173.30, 173.18, 155.13, 154.99, 154.94, 138.94, 138.67, 138.05, 137.74, 137.04, 136.85, 136.78, 133.07, 132.95, 128.97, 128.93, 128.77, 128.72, 128.66, 128.49, 128.44, 128.32, 128.29, 128.00, 127.81, 124.82, 124.79, 124.34, 66.95, 66.53, 56.61, 55.96, 55.73, 55.08, 55.22, 47.73, 47.55, 47.23, 47.06, 46.57, 46.33, 46.27, 46.11, 38.20, 37.51, 37.34, 36.89, 30.94, 30.71, 30.27, 30.12, 23.81, 23.76, 22.98, 22.88; HRMS (ESI) m z calcd for C$_{22}$H$_{25}$BrNO$_4$ [(M+H)$^+$] 446.09615, found 446.09693. IR (film) 2951, 1734, 1694, 1408, 1350, 1187, 1166, 1096, 1022, 748, 697 cm$^{-1}$;

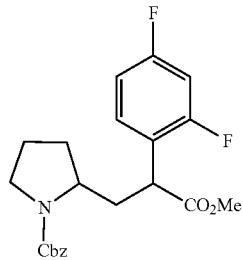 [SMILES: COC(=O)C(CC1CCCN1C(=O)OCc1ccccc1)c1ccc(F)cc1F]

(±)-Benzyl 2-(2-(2,4-difluorophenyl)-3-methoxy-3-oxopropyl)pyrrolidine-1-carboxylate: According to the general procedure, Ir[dF(CF$_3$)ppy)]$_2$(dtbbpy)PF$_6$ (2.2 mg, 2 μmol, 0.01 equiv.), Cbz-Pro-OH (74.8 mg, 0.30 mmol, 1.5 equiv.), K$_2$HPO$_4$ (52.3 mg, 0.3 mmol, 1.5 equiv.), methyl 2-(2,4-difluorophenyl)acrylate (39.6 mg, 0.2 mmol, 1.0 equiv.) and DMF (0.5 mL) were used. The product was isolated by flash chromatography (30% ethyl acetate in hexanes) as a colorless oil (73 mg, 90%). $^1$H NMR (500 MHz, CDCl$_3$) mixture of diastereomers and rotamers: δ 7.55-7.23 (m, 5.9H), 7.11-7.03 (m, 0.3H), 6.89-6.70 (m, 1.6H), 6.54 (t, J=8.0 Hz, 0.2H), 5.22-5.03 (m, 2H), 4.14-4.06 (m, 0.3H), 4.06-3.93

(m, 1H), 3.93-3.86 (m, 0.2H), 3.82-3.74 (m, 0.2H), 3.70-3.57 (m, 3H), 3.54-3.31 (m, 2H), 2.69-2.61 (m, 0.3H), 2.58-2.50 (m, 0.3H), 2.45-2.35 (m, 0.2H), 2.28-2.19 (m, 0.2H), 2.11-1.52 (m, 5H); $^{13}$C NMR (125 MHz, CDCl$_3$) mixture of diastereomers and rotamers: δ 173.32, 173.22, 173.12, 173.04, 163.06, 162.95, 162.87, 161.53, 161.44, 161.35, 161.20, 160.97, 159.56, 159.46, 159.37, 159.27, 155.13, 155.01, 154.91, 136.92, 136.76, 136.59, 130.37, 130.12, 129.82, 129.66, 128.46, 128.27, 128.13, 127.93, 127.83, 127.80, 127.70, 122.56, 122.44, 122.27, 122.15, 121.32, 121.20, 120.95, 120.82, 111.85, 111.66, 111.50, 111.36, 104.08, 103.95, 103.87, 103.75, 103.67, 103.54, 67.06, 66.61, 56.32, 55.76, 54.96, 52.30, 52.24, 46.58, 46.31, 46.14, 41.06, 40.48, 40.23, 40.09, 37.76, 37.19, 36.45, 35.89, 31.00, 30.36, 29.82, 23.82, 23.75, 23.01, 22.87; HRMS (ESI) m z calcd for C$_{22}$H$_{24}$F$_2$NO$_4$ [(M+H)$^+$] 404.16679, found 404.16672. IR (film) 2954, 2883, 1736, 1694, 1503, 1409, 1352, 1279, 1196, 1156, 1140, 1098, 964, 850, 698 cm$^{-1}$;

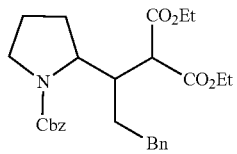

(±)-Diethyl 2-(1-(1-benzoylpyrrolidin-2-yl)ethyl)malonate: According to the general procedure, Ir[dF(CF$_3$)ppy]$_2$(dtbbpy)PF$_6$ (2.2 mg, 20.0 µmol, 0.01 equiv), Cbz-Pro-OH (50.0 mg, 0.2 mmol, 1.0 equiv), diethyl 2-(3-phenylpropylidene)malonate (55.5 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (25% ethyl acetate/hexane) as a pale yellow oil (89 mg, 92%). $^1$H NMR (500 MHz, CDCl$_3$) mixture of diastereomers and rotamers: δ 7.45-7.29 (m, 5H), 7.27-7.23 (m, 2H), 7.18-7.04 (m, 3H), 5.20-5.05 (m, 2H), 4.22-3.99 (m, 5H), 3.76-3.57 (m, 1H), 3.50-3.47 (m, 0.5H), 3.40-3.36 (m, 0.5H), 3.25-3.14 (m, 1H), 3.07 (br, 0.6H), 2.72-2.38 (m, 2.4H), 2.00-1.95 (m, 1H), 1.91-1.84 (m, 1H), 1.82-1.58 (m, 4H), 1.27-1.19 (m, 6H); $^{13}$C NMR (125 MHz, CDCl$_3$) mixture of diastereomers and rotamers: δ 169.02, 168.93, 168.76, 168.61, 155.67, 155.35, 142.35, 142.23, 142.00, 141.92, 136.83, 136.76, 136.64, 136.40, 128.52, 128.46, 128.40, 128.37, 128.29, 128.22, 128.15, 128.00, 127.92, 127.79, 125.89, 67.43, 67.31, 66.93, 66.80, 61.63, 61.42, 61.36, 60.50, 59.79, 59.56, 58.88, 54.13, 53.73, 53.37, 52.86, 48.16, 47.74, 47.49, 47.01, 42.22, 41.93, 40.58, 34.53, 34.25, 33.04, 32.75, 31.87, 31.75, 31.25, 29.77, 29.49, 27.47, 27.24, 24.32, 23.75, 23.65, 23.00, 14.13, 14.09, 14.02; HRMS (ESI) m/z calcd for C$_{28}$H$_{36}$NO$_6$ [(M+H)$^+$] 482.2543, found 482.2557. IR (film) 2947, 1697, 1405, 1096, 749, 698 cm$^{-1}$;

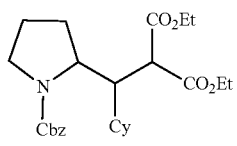

(±)-Diethyl 2-((1-((benzyloxy)carbonyl)pyrrolidin-2-yl)(cyclohexyl)methyl)malonate: According to the general procedure, Ir[dF(CF$_3$)ppy]$_2$(dtbbpy)PF$_6$ (2.2 mg, 10.0 µmol, 0.01 equiv), Cbz-Pro-OH (50.0 mg, 0.2 mmol, 1.0 equiv), diethyl 2-(cyclohexylmethylene)malonate (50.8 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (25% ethyl acetate/hexane) as a pale yellow oil (80 mg, 87%). $^1$H NMR (500 MHz, CDCl$_3$) mixture of diastereomers and rotamers: δ 7.47-7.29 (m, 5H), 5.22-5.01 (m, 2H), 4.21-4.06 (m, 4H), 3.96-3.87 (m, 0.25H), 3.70-3.53 (m, 1.75H), 3.29-3.17 (m, 1H), 3.07-3.00 (m, 1H), 1.97-1.56 (m, 11H), 1.27 (d, J=7.0 Hz, 3H), 1.20 (d, J=7.0 Hz, 3H), 1.13-0.96 (m, 5H); $^{13}$C NMR (125 MHz, CDCl$_3$) mixture of diastereomers and rotamers: δ 169.69, 169.63, 169.53, 169.03, 168.73, 156.83, 155.73, 155.68, 155.47, 137.04, 136.74, 136.64, 136.06, 129.35, 128.53, 128.46, 128.31, 127.98, 127.90, 127.75, 67.87, 67.36, 67.00, 66.66, 61.60, 61.43, 61.31, 61.05, 58.35, 57.85, 57.55, 57.06, 52.98, 52.71, 51.20, 50.80, 49.67, 49.26, 47.83, 47.72, 47.33, 47.22, 45.83, 45.19, 40.27, 40.21, 38.96, 38.70, 33.85, 33.27, 32.02, 31.49, 30.86, 28.28, 27.68, 27.63, 27.43, 27.37, 27.05, 26.86, 26.71, 26.59, 26.48, 24.40, 23.82, 23.33, 22.42, 14.22, 14.12, 14.00; HRMS (ESI) m/z calcd for C$_{26}$H$_{38}$NO$_6$ [(M+H)$^+$] 460.2699, found 460.2697. IR (film) 2926, 1698, 1404, 1097, 698 cm$^{-1}$;

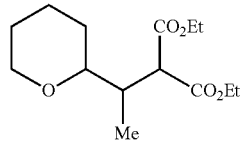

(±)-Diethyl 2-(1-(tetrahydro-2H-pyran-2-yl)ethyl)malonate: According to the general procedure, Ir[dF(CF$_3$)ppy]$_2$(dtbbpy)PF$_6$ (2.2 mg, 2 µmol, 0.01 equiv.), tetrahydro-2H-pyran-4-carboxylic acid (26 mg, 0.2 mmol, 1.0 equiv), diethyl ethylidenemalonate (37.3 mg, 0.20 mmol, 1.0 equiv), K$_2$HPO$_4$ (42.0 mg, 0.24 mmol, 1.2 equiv), and 0.5 mL of DMF were used. The product was isolated by flash chromatography (10% ethyl acetate/hexane) as a pale yellow oil (50 mg, 90%). $^1$H NMR (500 MHz, CDCl$_3$) mixture of diastereomers: δ 4.23-4.15 (m, 4H), 3.94 (d, J=10.5 Hz, 1H), 3.73 (d, J=5.5 Hz, 0.4H), 3.51 (d, J=9.0 Hz, 0.6H), 3.37-3.26 (m, 1.6H), 3.16 (t, J=9.5 Hz, 0.4H), 2.33-2.27 (m, 1H), 1.87-1.84 (m, 1H), 1.74 and 1.72 (2 brs, 0.4H), 1.53-1.42 (m, 4H), 1.28-1.17 (m, 6.6H), 1.00-0.97 (m, 3H); $^{13}$C NMR (125 MHz, CDCl$_3$) mixture of diastereomers: δ 169.66, 169.11, 169.05, 168.88, 79.27, 78.47, 68.69, 68.54, 61.13, 61.08, 60.98, 60.79, 54.94, 52.92, 39.03, 38.14, 29.16, 28.65, 26.02, 26.00, 23.71, 23.46, 14.16, 14.11, 14.08, 12.88, 11.70; HRMS (ESI) m/z calcd for C$_{14}$H$_{25}$O$_5$ [(M+H)$^+$] 273.1702, found 273.1703. IR (film) 2939, 1749, 1729, 1088, 1029, 895 cm$^{-1}$;

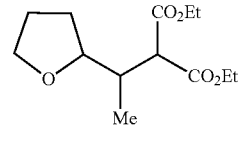

(±)-Diethyl 2-(1-(tetrahydrofuran-2-yl)ethyl)malonate: According to the general procedure, Ir[dF(CF$_3$)ppy]$_2$(dtbbpy)PF$_6$ (2.2 mg, 2 µmol, 0.01 equiv.), tetrahydro-2-furoic acid (24 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), and 0.5 mL of DMF were used.

The product was isolated by flash chromatography (10% ethyl acetate/hexane) as a pale yellow oil (47.5 mg, 92%). $^1$H NMR (500 MHz, CDCl$_3$) mixture of diastereomers: δ 4.24-4.16 (m, 4H), 3.86-3.68 (m, 3H), 3.61 (d, J=6.0 Hz, 0.55H), 3.42 (d, J=9.0 Hz, 0.45H), 2.52-2.45 (m, 0.45H), 2.33-2.26 (m, 0.55H), 2.03-1.82 (m, 3H), 1.64-1.57 (m, 1H), 1.28-1.25 (m, 6H), 0.98 (t, J=7.0 Hz, 3H); $^{13}$C NMR (125 MHz, CDCl$_3$) mixture of diastereomers: δ 169.31, 168.86, 168.83, 168.77, 81.25, 80.35, 68.32, 67.75, 61.22, 61.17, 61.09, 61.00, 54.93, 54.42, 39.09, 37.36, 30.00, 28.46, 25.98, 25.86, 14.13, 14.09, 14.06, 14.05, 13.49, 12.31; HRMS (ESI) m/z calcd for C$_{13}$H$_{23}$O$_5$ [(M+H)$^+$] 259.1545, found 259.1525. IR (film) 2978, 1748, 1728, 1153, 1065, 1030 cm$^{-1}$;

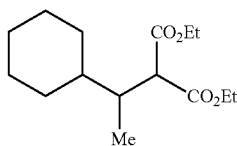 [SMILES: CCOC(=O)C(C(=O)OCC)C(C)C1CCCCC1]

(+)-Diethyl 2-(1-cyclohexylethyl)malonate [known compound (2)]: According to the general procedure, Ir[dF(CF$_3$)ppy)]$_2$(dtbbpy)PF$_6$ (2.2 mg, 2 μmol, 0.01 equiv.), cyclohexanecarboxylic acid (26 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), 0.5 mL of DMF and 34 W Blue LED (instead of 26 W fluorescent light bulb) were used. The product was isolated by flash chromatography (10% ethyl acetate/hexane) as a pale yellow oil (41 mg, 75%). $^1$H NMR (500 MHz, CDCl$_3$) δ 4.23-4.16 (m, 4H), 3.39 (d, J=9.5 Hz, 1H), 2.21-2.14 (m, 1H), 1.76-1.71 (m, 2H), 1.67-1.57 (m, 3H), 1.30-1.08 (m, 11H), 0.98-0.92 (m, 1H), 0.90 (d, J=7.0 Hz, 3H); $^{13}$C NMR (125 MHz, CDCl$_3$) δ 169.30, 169.05, 61.14, 61.06, 55.81, 40.24, 38.56, 31.52, 27.37, 26.73, 26.53, 26.46, 14.13, 12.89; HRMS (ESI) m/z calcd for C$_{15}$H$_{26}$NaO$_4$ [(M+Na)$^+$] 293.1729, found 293.1727. IR (film) 2925, 1753, 1729, 1147, 1031 cm$^{-1}$;

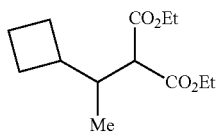

(+)-Diethyl 2-(1-cyclobutylethyl)malonate: According to the general procedure, Ir[dF(CF$_3$)ppy)]$_2$(dtbbpy)PF$_6$ (2.2 mg, 2 μmol, 0.01 equiv.), cyclobutanecarboxylic acid (20 mg, 0.2 mmol, 1.0 equiv), diethyl ethylidenemalonate (54 mg, 0.2 mmol, 1.0 equiv), K$_2$HPO$_4$ (42.0 mg, 0.3 mmol, 1.2 equiv), 0.5 mL of DMF and 34 W Blue LED (instead of 26 W fluorescent light bulb) were used. The product was isolated by flash chromatography (10% ethyl acetate/hexane) as a pale yellow oil (33 mg, 68%). $^1$H NMR (500 MHz, CDCl$_3$) δ 4.20-4.14 (m, 4H), 3.22 (d, J=6.5 Hz, 1H), 2.27-2.13 (m, 2H), 2.01-1.89 (m, 2H), 1.83-1.74 (m, 1H), 1.72-1.62 (m, 3H), 1.27 (t, J=7.5 Hz, 6H), 0.91 (d, J=6.5 Hz, 3H); $^{13}$C NMR (125 MHz, CDCl$_3$) δ 169.26, 168.71, 61.16, 60.96, 55.03, 40.10, 39.95, 27.28, 27.05, 17.50, 14.14, 14.06, 13.96; HRMS (ESI) m/z calcd for C$_{13}$H$_{22}$NaO$_4$ [(M+Na)$^+$] 265.1416, found 265.1400. IR (film) 2970, 1750, 1729, 1148, 1032 cm$^{-1}$.

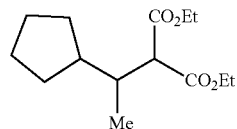

(±)-Diethyl 2-(1-cyclopentylethyl)malonate: According to the general procedure, Ir[dF(CF$_3$)ppy)]$_2$(dtbbpy)PF$_6$ (2.2 mg, 2 μmol, 0.01 equiv.), cyclopentanecarboxylic acid (24 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), and 0.5 mL of 1,4-dioxane were used. The product was isolated by flash chromatography (10% ethyl acetate/hexane) as a pale yellow oil (30 mg, 58%). $^1$H NMR (500 MHz, CDCl$_3$) δ 4.19 (q, J=7.5 Hz, 4H), 3.41 (d, J=6.5 Hz, 1H), 2.17-2.10 (m, 1H), 1.79-1.71 (m, 3H), 1.64-1.58 (m, 2H), 1.53-1.50 (m, 2H), 1.27 (td, J=7.5 Hz, J=2.5 Hz, 6H), 1.19-1.13 (m, 2H), 1.02 (d, J=7.0 Hz, 3H); $^{13}$C NMR (125 MHz, CDCl$_3$) δ 169.48, 168.86, 61.15, 60.91, 56.32, 43.82, 38.48, 30.96, 29.66, 25.32, 25.28, 14.61, 14.16, 14.10; HRMS (ESI) m/z calcd for C$_{14}$H$_{25}$O$_4$ [(M+H)$^+$] 257.1753, found 257.1770. IR (film) 2952, 1750, 1728, 1124, 1150, 1030 cm$^{-1}$;

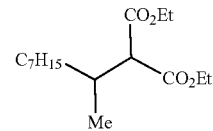

(±)-Diethyl 2-(nonan-2-yl)malonate: According to the general procedure, Ir[dF(CF$_3$)ppy)]$_2$(dtbbpy)PF$_6$ (2.2 mg, 2 μmol, 0.01 equiv.), octanoic acid (29 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), 0.5 mL of DMF and 34 W Blue LED (instead of 26 W fluorescent light bulb) were used. The product was isolated by flash chromatography (10% ethyl acetate/hexane) as a colorless oil (22 mg, 38%). $^1$H NMR (500 MHz, CDCl$_3$) δ 4.19 (q, J=7.0 Hz, 4H), 3.22 (d, J=8.0 Hz, 1H), 2.27-2.19 (m, 1H), 1.42-1.18 (m, 18H), 0.98 (d, J=7.0 Hz, 3H), 0.87 (t, J=7.0 Hz, 3H); $^{13}$C NMR (125 MHz, CDCl$_3$) δ 169.05, 168.89, 61.12, 61.06, 57.84, 34.34, 33.39, 31.83, 29.59, 29.24, 26.81, 22.66, 16.96, 14.14, 14.12, 14.11; HRMS (ESI) m/z calcd for C$_{16}$H$_{30}$NaO$_4$ [(M+Na)$^+$] 309.2036, found 309.2026. IR (film) 2927, 1753, 1731, 1148, 1031 cm$^{-1}$.

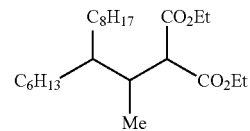

(±)-Diethyl 2-(3-hexylundecan-2-yl)malonate: According to the general procedure, Ir[dF(CF$_3$)ppy)]$_2$(dtbbpy)PF$_6$ (2.2 mg, 2 μmol, 0.01 equiv.), 2-hexyldecanoic acid (52 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), 0.5 mL of DMF and 34 W Blue LED (instead of 26 W fluorescent light bulb) were used. The product was isolated by flash chromatography (10% ethyl acetate/hexane) as a pale yellow oil (42 mg, 53%). $^1$H NMR (500 MHz, CDCl$_3$) δ 4.21-4.16 (m, 4H), 3.34 (d, J=10.5 Hz, 1H), 2.46-2.38 (m, 1H), 1.36-1.17 (m, 30H), 1.00-0.94 (m, 1H), 0.88 (t, J=7.0 Hz, 6H), 0.81 (t, J=7.0 Hz, 3H); $^{13}$C NMR (125 MHz, CDCl$_3$) δ 169.12, 168.97, 61.16, 56.63, 39.69, 35.09, 31.93, 31.89, 31.79, 30.32, 30.09, 29.96, 29.75, 29.64, 29.59, 29.38, 29.31, 28.06, 28.02, 27.42, 27.39, 22.70, 14.13, 11.61; HRMS (ESI) m/z calcd for C$_{24}$H$_{46}$NaO$_4$ [(M+Na)$^+$] 421.3294, found 421.3293. IR (film) 2924, 2855, 1757, 1733, 1175, 1032 cm$^{-1}$;

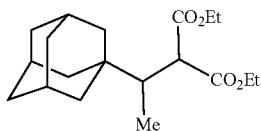 [SMILES: CCOC(=O)C(C(=O)OCC)C(C)C12CC3CC(CC(C3)C1)C2]

(±)-Diethyl 2-(1-((3r,5r,7r)-adamantan-1-yl)ethyl)malonate: According to the general procedure, Ir[dF(CF$_3$)ppy)]$_2$(dtbbpy)PF$_6$ (2.2 mg, 2 μmol, 0.01 equiv.), 1-adamantanecarboxylic acid (36 mg, 0.2 mmol, 1.0 equiv), diethyl ethylidenemalonate (37.7 mg, 0.2 mmol, 1.0 equiv), K$_2$HPO$_4$ (42.0 mg, 0.24 mmol, 1.2 equiv), 0.5 mL of DMF and 34 W Blue LED (instead of 26 W fluorescent light bulb) were used. The product was isolated by flash chromatography (10% ethyl acetate/hexane) as a pale yellow oil (60 mg, 93%). $^1$H NMR (500 MHz, CDCl$_3$) δ 4.21-4.14 (m, 4H), 3.57 (d, J=5.5 Hz, 1H), 2.09-2.04 (m, 1H), 1.98-1.95 (m, 3H), 1.69-1.67 (m, 3H), 1.61-1.59 (m, 3H), 1.53-1.47 (m, 6H), 1.27 (q, J=7.0 Hz, 6H), 0.98 (d, J=7.5 Hz, 3H); $^{13}$C NMR (125 MHz, CDCl$_3$) δ 170.38, 169.79, 61.32, 60.89, 51.83, 43.08, 39.36, 37.02, 35.23, 28.61, 14.09, 14.05, 10.40; HRMS (ESI) m/z calcd for C$_{19}$H$_{30}$NaO$_4$ [(M+Na)$^+$] 345.2042, found 345.2024. IR (film) 2901, 2848, 1728, 1218, 1148, 1137, 1031 cm$^{-1}$;

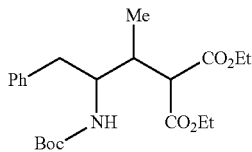 [SMILES: CCOC(=O)C(C(=O)OCC)C(C)C(Cc1ccccc1)NC(=O)OC(C)(C)C]

(±)-Diethyl 2-(3-((tert-butoxycarbonyl)amino)-4-phenylbutan-2-yl)malonate: According to the general procedure, Ir[dF(CF$_3$)ppy)]$_2$(dtbbpy)PF$_6$ (2.2 mg, 2 μmol, 0.01 equiv.), Boc-Phe-OH (53.0 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (15% ethyl acetate/hexane) as a pale yellow oil (77 mg, 94%). $^1$H NMR (500 MHz, CDCl$_3$) mixture of diastereomers: δ 7.29-7.25 (m, 2H), 7.21-7.15 (m, 3H), 4.49 (d, J=9.5 Hz, 0.43H), 4.32-3.98 (m, 5H), 3.86-3.72 (m, 0.57H), 3.51-3.46 (m, 0.55H), 3.39-3.33 (m, 0.45H), 2.99-2.95 (m, 0.6H), 2.81-2.73 (m, 0.8H), 2.66-2.61 (m, 0.6H), 2.50-2.39 (m, 1H), 1.32-1.19 (m, 15H), 1.15 (d, J=6.5 Hz, 1.7H), 0.95 (d, J=7.0 Hz, 1.3H); $^{13}$C NMR (125 MHz, CDCl$_3$) mixture of diastereomers: δ 169.67, 169.01, 168.43, 155.56, 155.34, 138.03, 137.97, 129.41, 129.17, 128.51, 128.48, 126.48, 79.30, 79.21, 61.60, 61.48, 61.46, 61.43, 55.65, 55.26, 54.28, 52.81, 39.93, 39.08, 37.18, 35.76, 28.36. 15.12, 14.20, 14.18, 14.12, 11.15; HRMS (ESI) m/z calcd for C$_{22}$H$_{34}$NO$_6$ [(M+H)$^+$] 408.2386, found 408.2388. IR (film) 2978, 1704, 1365, 1165, 1026, 699 cm$^{-1}$;

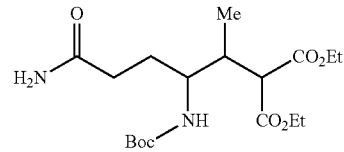

(±)-Diethyl 2-(6-amino-3-((tert-butoxycarbonyl)amino)-6-oxohexan-2-yl)malonate: According to the general procedure, Ir[dF(CF$_3$)ppy)]$_2$(dtbbpy) (2.2 mg, 2 μmol, 0.01 equiv.), Boc-Gln-OH (49 mg, 0.2 mmol, 1.0 equiv.), diethyl ethylidenemalonate (37.3 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (60% ethyl acetate/hexane) as a pale yellow solid (65 mg, 84%). $^1$H NMR (500 MHz, CDCl$_3$) mixture of diastereomers: δ 6.35 (s, 0.5H), 6.14 (s, 0.5H), 5.40 (s, 1H), 4.76 (d, J=10.0 Hz, 0.5H), 4.46 (d, J=10.5 Hz, 0.5H), 4.23-4.17 (m, 4H), 3.87-3.81 (m, 0.5H), 3.64-3.59 (m, 0.5H), 3.44 (d, J=6.5 Hz, 0.5H), 3.20 (d, J=10.0 Hz, 0.5H), 2.46-2.34 (m, 1H), 2.29-2.24 (m, 2H), 2.02-1.96 (m, 0.5H), 1.83-1.77 (m, 2H), 1.63-1.55 (m, 0.5H), 1.42 (s, 9H), 1.29-1.24 (m, 6H), 1.06 (d, J=7.0 Hz, 1.5H), 0.91 (d, J=7.0 Hz, 1.5H); $^{13}$C NMR (125 MHz, CDCl$_3$) mixture of diastereomers: δ 175.61, 175.55, 169.42, 168.91, 168.81, 168.52, 156.35, 156.30, 79.56, 79.49, 61.64, 61.53, 61.48, 61.47, 55.53, 54.25, 53.49, 51.50, 37.90, 36.96, 32.96, 32.65, 29.75, 29.28, 28.39, 28.36, 14.73, 14.13, 14.09, 14.03, 11.14; HRMS (ESI) m/z calcd for C$_{18}$H$_{33}$N$_2$O$_7$ [(M+H)$^+$] 389.2288, found 389.2296. IR (film) 3347, 2978, 1670, 1165, 1026, 735 cm$^{-1}$;

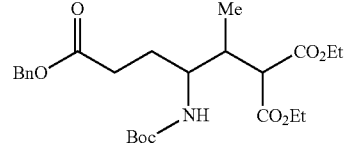 [SMILES: CCOC(=O)C(C(=O)OCC)C(C)C(CCC(N)=O)NC(=O)OC(C)(C)C]

(+)-5-Benzyl 1,1-diethyl 3-((tert-butoxycarbonyl)amino)-2-methylpentane-1,1,5-tricarboxylate: According to the general procedure, Ir[dF(CF$_3$)ppy)]$_2$(dtbbpy)PF$_6$ (2.2 mg, 2 μmol, 0.01 equiv.), Boc-Glu(OBzl)-OH (67 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (20% ethyl acetate/hexane) as a pale yellow oil (89 mg, 93%). $^1$H NMR (500 MHz, CDCl$_3$) mixture of diastereomers: δ 7.38-7.31 (m, 5H), 5.15-5.08 (m, 2H), 4.52 (d, J=10.0 Hz, 0.4H), 4.31 (d, J=10.5 Hz, 0.4H), 4.22-4.16 (m, 4.2H), 3.86-3.74 (m, 0.5H), 3.62-3.49 (m, 0.5H), 3.42 (d, J=7.0 Hz, 0.5H), 3.28 (d, J=10.0 Hz, 0.5H), 2.50-2.34 (m, 3H), 2.03-1.96 (m, 0.5H), 1.85-1.74 (m, 1H), 1.65-1.60 (m, 0.5H), 1.41 (m, 5H), 1.40 (s, 4H), 1.27 (qd, J=7.0 Hz, J=3.0 Hz, 6H), 1.05 (d, J=7.0 Hz, 1.6H), 0.89 (d, J=7.0 Hz, 1.4H); $^{13}$C NMR (125 MHz, CDCl$_3$) mixture of diastereomers: δ 173.23, 173.20, 169.45, 168.82, 168.78, 168.38, 155.70, 155.51, 135.90, 135.89, 128.56, 128.24, 128.21, 128.20, 79.37, 79.26, 66.37, 66.34, 61.56, 61.43, 61.37, 55.41, 54.26, 53.59, 51.52, 37.87, 36.83, 31.47, 31.02, 28.70, 28.35, 28.32, 28.14, 14.69, 14.10, 14.06, 14.01, 11.12; HRMS (ESI) m/z calcd for C$_{25}$H$_{38}$NO$_8$ [(M+H)$^+$] 480.2597, found 480.2604. IR (film) 2978, 1727, 1710, 1161, 1026, 698 cm$^{-1}$;

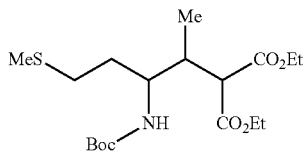

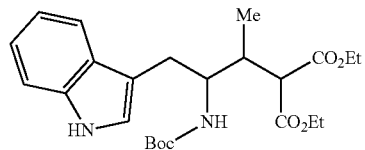 [SMILES: CCOC(=O)C(C(=O)OCC)C(C)C(Cc1c[nH]c2ccccc12)NC(=O)OC(C)(C)C]

(±)-Diethyl 2-(3-((tert-butoxycarbonyl)amino)-5-(methylthio)pentan-2-yl)malonate: According to the general procedure, Ir[dF(CF$_3$)ppy]$_2$(dtbbpy)PF$_6$ (2.2 mg, 2 μmol, 0.01 equiv.), Boc-Met-OH (50.0 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (20% ethyl acetate/hexane) as a pale yellow oil (74 mg, 94%). $^1$H NMR (500 MHz, CDCl$_3$) mixture of diastereomers: δ 4.56 (d, J=9.5 Hz, 0.5H), 4.31 (d, J=10.5 Hz, 0.3H), 4.23-4.17 (m, 4.2H), 3.92-3.87 (m, 0.4H), 3.68-3.63 (m, 0.6H), 3.42 (d, J=7.0 Hz, 0.6H), 3.29 (d, J=10.0 Hz, 0.4H), 2.59-1.67 (m, 8H), 1.43 (s, 5H), 1.42 (s, 4H), 1.29-1.25 (m, 6H), 1.05 (d, J=7.0 Hz, 1.7H), 0.89 (d, J=7.0 Hz, 1.3H); $^{13}$C NMR (125 MHz, CDCl$_3$) mixture of diastereomers: δ 169.53, 168.90, 168.45, 155.74, 155.58, 79.46, 79.32, 61.64, 61.53, 61.46, 55.49, 54.33, 53.58, 51.41, 37.66, 36.80, 34.02, 33.02, 31.16, 30.85, 28.42, 28.39, 15.76, 15.74, 14.81, 14.17, 14.14, 14.08, 11.20; HRMS (ESI) m/z calcd for C$_{18}$H$_{33}$NNaO$_6$S [(M+Na)$^+$] 414.1926, found 414.1940. IR (film) 2978, 1715, 1366, 1168, 1031 cm$^{-1}$;

(+)-Diethyl 2-(3-((tert-butoxycarbonyl)amino)-4-(1H-indol-3-yl)butan-2-yl)malonate: According to the general procedure, Ir[dF(CF$_3$)ppy]$_2$(dtbbpy)PF$_6$ (2.2 mg, 2 μmol, 0.01 equiv.), Boc-Trp-OH (61 mg, 0.2 mmol, 1.0 equiv.), diethyl ethylidenemalonate (37.3 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (20% ethyl acetate/hexane) as a pale yellow solid (51 mg, 57%). $^1$H NMR (500 MHz, CDCl$_3$) mixture of diastereomers: δ 8.02 (br, 1H), 7.60 (dd, J=17.5 Hz, J=8.0 Hz, 1H), 7.60 (dd, J=8.0 Hz, J=3.5 Hz, 1H), 7.20-7.16 (m, 1H), 7.13-7.05 (m, 2H), 4.59 (d, J=9.5 Hz, 0.3H), 4.41 (d, J=9.5 Hz, 0.3H), 4.30-4.28 (m, 0.4H), 4.22-4.15 (m, 4.5H), 3.95 (br, 0.5H), 3.54 (d, J=6.5 Hz, 0.5H), 3.39 (d, J=10.0 Hz, 0.5H), 3.10-3.06 (m, 0.5H), 2.95-2.78 (m, 1.5H), 2.62-2.56 (m, 0.5H), 2.48 (q, J=7.0 Hz, 0.5H), 1.35-1.33 (m, 6H), 1.29-1.17 (m, 9H), 1.10-1.03 (m, 1.5H), 0.97 (d, J=7.0 Hz, 1.5H); $^{13}$C NMR (125 MHz, CDCl$_3$) mixture of diastereomers: δ 169.80, 169.20, 169.12, 168.65, 155.85, 155.63, 136.57, 136.27, 128.07, 127.82, 127.54, 122.78, 122.63, 122.46, 121.97, 121.88, 119.40, 119.30, 118.86, 118.69, 111.98, 111.47, 111.25, 79.31, 79.11, 61.57, 61.51, 61.45, 55.77, 54.56, 54.16, 52.07, 36.86, 36.42, 35.76, 28.36, 27.73, 15.15, 14.18, 14.14, 14.05, 11.09; HRMS (ESI) m/z calcd for C$_{24}$H$_{35}$N$_2$O$_6$ [(M+H)$^+$] 447.2495, found 447.2498. IR (film) 3387, 2978, 1721, 1169, 1027, 741 cm$^{-1}$;

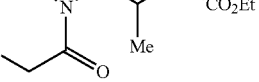

(±)-Diethyl 2-(4-(benzyloxy)-3-((tert-butoxycarbonyl)amino)butan-2-yl)malonate: According to the general procedure, Ir[dF(CF$_3$)ppy]$_2$(dtbbpy)PF$_6$ (2.2 mg, 2 μmol, 0.01 equiv.), Boc-Ser(Bzl)-OH (59 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (25% ethyl acetate/hexane) as a pale yellow oil (83 mg, 94%). $^1$H NMR (500 MHz, CDCl$_3$) mixture of diastereomers: δ 7.36-7.27 (m, 5H), 4.94 (d, J=9.5 Hz, 0.5H), 4.68 (d, J=9.5 Hz, 0.5H), 4.53-4.46 (m, 2H), 4.23-4.14 (m, 4H), 4.04-3.92 (m, 0.5H), 3.78-3.75 (m, 0.5H), 3.63-3.55 (m, 1.5H), 3.50-3.46 (m, 1H), 3.41 (d, J=9.0 Hz, 0.5H), 2.61-2.56 (m, 1H), 1.43 (s, 4.3H), 1.42 (s, 4.7H), 1.26 (td, J=7.0 Hz, J=2.5 Hz, 6H), 1.05 (d, J=7.0 Hz, 1.6H), 0.96 (d, J=7.0 Hz, 1.4H); $^{13}$C NMR (125 MHz, CDCl$_3$) mixture of diastereomers: δ 169.76, 168.99, 168.88, 168.76, 155.80, 155.61, 138.11, 128.50, 128.49, 127.81, 127.76, 127.69, 79.45, 79.35, 73.29, 73.06, 70.96, 70.20, 61.48, 61.38, 61.26, 55.12, 53.89, 53.50, 51.23, 34.94, 34.91, 28.46, 14.41, 14.21, 14.18, 14.14, 12.31; HRMS (ESI) m/z calcd for C$_{23}$H$_{36}$NO$_7$ [(M+H)$^+$] 438.2492, found 438.2496. IR (film) 2978, 1715, 1164, 1028, 698 cm$^{-1}$;

(±)-Diethyl 2-(1-(1-(((benzyloxy)carbonyl)glycyl)pyrrolidin-2-yl)ethyl)malonate: According to the general procedure, Ir[dF(CF$_3$)ppy]$_2$(dtbbpy)PF$_6$ (2.2 mg, 2 μmol, 0.01 equiv.), Z-Gly-Pro (61.1 mg, 0.2 mmol, 1.0 equiv.), diethyl ethylidenemalonate (37.3 mg, 0.20 mmol, 1.0 equiv), K$_2$HPO$_4$ (42.0 mg, 0.24 mmol, 1.2 equiv), and 0.5 mL of DMF were used. The product was isolated by flash chromatography (20% ethyl acetate/hexane) as a pale yellow solid (79 mg, 88%). $^1$H NMR (500 MHz, CDCl$_3$) mixture of diastereomers and rotamers: δ 7.36-7.229 (m, 5H), 5.80-5.59 (m, 1H), 5.14-5.09 (m, 2H), 4.31-4.28 (m, 0.4H), 4.23-4.13 (m, 4H), 4.09-4.00 (m, 0.6H), 4.00 (d, J=4.0 Hz, 0.15H), 3.96 (dd, J=7.0 Hz, J=7.0 Hz, 0.55H), 3.91 (q, J=4.5 Hz, 0.6H), 3.87 (d, J=4.0 Hz, 0.3H), 3.81 (d, J=4.0 Hz, 0.2H), 3.78 (q, J=4.5 Hz, 0.2H), 3.64 (q, J=9.5 Hz, 0.4H), 3.50-3.47 (m, 0.6H), 3.46-3.44 (m, 0.4H), 3.32-3.18 (m, 1.6H), 2.70-2.65 (m, 1H), 2.10-1.76 (m, 4H), 1.29-1.19 (m, 6H), 1.01 (d, J=7.0 Hz, 0.2H), 0.95 (d, J=6.5 Hz, 1.3H), 0.92 (d, J=7.0 Hz, 0.2H), 0.88 (d, J=7.0 Hz, 1.3H); $^{13}$C NMR (125 MHz, CDCl$_3$) mixture of diastereomers and rotamers: 6169.01, 168.84, 168.67, 168.46, 168.37, 168.11, 168.05, 167.92, 167.70, 167.58, 156.25, 156.21, 136.56, 136.54, 128.55, 128.12, 128.03, 66.86, 62.04, 62.00, 61.81, 61.79, 61.51, 61.38, 61.36, 61.07, 60.26, 60.05, 59.05, 55.70, 55.09, 53.30, 46.93, 46.82, 46.39, 46.06, 43.78, 43.48, 43.37, 37.25, 36.78, 36.35, 36.16, 29.14, 27.60, 24.47, 23.84, 22.73, 22.32, 14.26, 14.17, 14.11, 14.05, 13.38; HRMS (ESI) m/z calcd for $C_{23}H_{33}N_2O_7$ [(M+H)$^+$] 449.2288, found 449.2278. IR (film) 2976, 1721, 1647, 1243, 1028, 698 cm$^{-1}$;

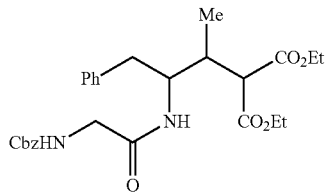 [SMILES: CCOC(=O)C(C(=O)OCC)C(C)C(Cc1ccccc1)NC(=O)CNC(=O)OCc1ccccc1]

(±)-Diethyl 2-(3-(2-(((benzyloxy)carbonyl)amino)acetamido)-4-phenylbutan-2-yl)malonate: According to the general procedure, Ir[dF(CF$_3$)ppy)]$_2$(dtbbpy)PF$_6$ (2.2 mg, 2 μmol, 0.01 equiv.), Z-Gly-Phe (71.3 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), and 1.0 mL of DMF were used. The product was isolated by flash chromatography (20% ethyl acetate/hexane) as a pale yellow solid (90 mg, 90%). $^1$H NMR (500 MHz, CDCl$_3$) mixture of diastereomers and rotamers: δ 7.37-7.30 (m, 5H), 7.27-7.24 (m, 2H), 7.21-7.17 (m, 1H), 7.16-7.12 (m, 2H), 6.44 (d, J=9.0 Hz, 0.6H), 5.92 (d, J=8.0 Hz, 0.4H), 5.21 (br, 1H), 5.13 (s, 2H), 4.47 (q, J=8.0 Hz, 0.4H), 4.24-4.14 (m, 4.6H), 3.76-3.67 (m, 2H), 3.50 (d, J=6.5 Hz, 0.6H), 3.29 (d, J=9.5 Hz, 0.4H), 2.93-2.89 (m, 0.6H), 2.84-2.80 (m, 0.4H), 2.75-2.71 (m, 1H), 2.53-2.41 (m, 1H), 1.27-1.22 (m, 6H), 1.14 (d, J=6.5 Hz, 1.7H), 0.94 (d, J=7.0 Hz, 1.3H); $^{13}$C NMR (125 MHz, CDCl$_3$) mixture of diastereomers and rotamers: δ 169.24, 168.99, 168.82, 168.48, 168.38, 156.73, 156.51, 137.73, 137.57, 136.27, 136.21, 129.24, 128.97, 128.60, 128.57, 128.50, 128.48, 128.29, 128.24, 128.03, 126.62, 126.58, 67.12, 67.07, 61.72, 61.64, 61.53, 61.43, 55.59, 53.95, 53.59, 51.67, 44.62, 44.47, 39.32, 38.14, 36.23, 35.91, 15.01, 14.12, 14.07, 14.06, 11.14; HRMS (ESI) m/z calcd for $C_{27}H_{35}N_2O_7$ [(M+H)$^+$] 449.2444, found 449.2420. IR (film) 3321, 2980, 1722, 1230, 1027, 733, 697 cm$^{-1}$;

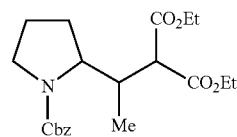 [SMILES: CCOC(=O)C(C(=O)OCC)C(C)C1CCCN1C(=O)OCc1ccccc1]

(±)-Diethyl 2-(1-(1-((benzyloxy)carbonyl)pyrrolidin-2-yl)ethyl)malonate: According to the general procedure, Ir[dF(CF$_3$)ppy)]$_2$(dtbbpy)PF$_6$ (2.2 mg, 2 μmol, 0.01 equiv.), Z-Pro-OH (50.0 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (20% ethyl acetate/hexane) as a pale yellow oil (72 mg, 92%). $^1$H NMR (500 MHz, CDCl$_3$) mixture of diastereomers and rotamers: δ 7.42-7.29 (m, 5H), 5.21-5.03 (m, 2H), 4.20-3.84 (m, 5H), 3.69-3.36 (m, 2H), 3.24-3.17 (m, 1H), 2.80-2.73 (m, 0.6H), 2.68-2.63 (m, 0.4H), 2.02-1.72 (m, 4H), 1.28-1.18 (m, 6H), 0.96-0.87 (m, 3H); $^{13}$C NMR (125 MHz, CDCl$_3$) mixture of diastereomers and rotamers: δ 169.05, 168.93, 168.87, 168.81, 168.71, 168.56, 168.47, 155.95, 155.85, 155.70, 155.27, 136.87, 136.81, 136.72, 136.65, 128.44, 128.20, 128.14, 127.92, 127.83, 127.77, 67.11, 66.79, 61.70, 61.46, 61.23, 60.56, 60.47, 59.96, 55.58, 55.13, 55.00, 54.50, 47.95, 47.66, 47.26, 46.76, 37.13, 37.05, 29.15, 28.78, 28.27, 28.16, 24.41, 23.79, 23.65, 23.19, 14.22, 14.12, 14.06, 14.02, 13.87, 13.68, 13.48; HRMS (ESI) m/z calcd for $C_{21}H_{30}NO_6$ [(M+H)$^+$] 392.2073, found 392.2066. IR (film) 2977, 1695, 1405, 1096, 1027, 697 cm$^{-1}$;

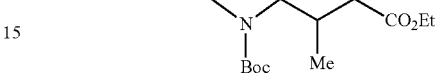

(±)-Diethyl 2-(1-(1-(tert-butoxycarbonyl)pyrrolidin-2-yl)ethyl)malonate: According to the general procedure, Ir[dF(CF$_3$)ppy)]$_2$(dtbbpy)PF$_6$ (2.2 mg, 2 μmol, 0.01 equiv.), Boc-Pro-OH (43.0 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (20% ethyl acetate/hexane) as a pale yellow oil (69 mg, 97%). $^1$H NMR (500 MHz, CDCl$_3$) mixture of diastereomers and rotamers: δ 4.22-4.11 (m, 4H), 3.97-3.30 (m, 3H), 3.17-3.12 (m, 0.55H), 3.11-3.06 (m, 0.45H), 2.75-2.71 (m, 0.83H), 2.60-2.53 (m, 0.17H), 2.00-1.67 (m, 4H), 1.46 (s, 9H), 1.28-1.23 (m, 6H), 0.94-0.88 (m, 3H); $^{13}$C NMR (125 MHz, CDCl$_3$) mixture of diastereomers and rotamers: δ 168.88, 168.73, 168.36, 155.43, 155.20, 154.79, 79.77, 79.07, 61.29, 61.12, 60.52, 60.26, 59.91, 55.52, 54.74, 54.00, 47.72, 47.14, 46.95, 46.81, 37.00, 36.77, 28.45, 28.42, 24.37, 23.77, 23.48, 23.26, 14.08, 14.02; HRMS (ESI) m/z calcd for $C_{18}H_{32}NO_6$ [(M+H)$^+$] 358.2230, found 358.2235. IR (film) 2975, 1729, 1689, 1381, 1365, 1162, 1105, 1030, 773 cm$^{-1}$;

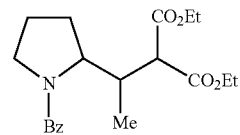

(±)-Diethyl 2-(1-(1-benzoylpyrrolidin-2-yl)ethyl)malonate: According to the general procedure, Ir[dF(CF$_3$)ppy)]$_2$(dtbbpy)PF$_6$ (5.5 mg, 5 μmol, 0.01 equiv.), Benzoyl-L-proline (110 mg, 0.5 mmol, 1.0 equiv.), K$_2$HPO$_4$ (105 mg, 0.6 mmol, 1.2 equiv.), diethyl 2-ethylidenemalonate (93 mg, 0.5 mmol, 1.0 equiv.) and DMF (1.25 mL) were used. The product was isolated by flash chromatography (30% ethyl acetate in hexanes) as a pale yellow oil (150 mg, 83%). $^1$H NMR (500 MHz, CDCl$_3$) mixture of diastereomers and rotamers: δ 7.56-7.48 (m, 2H), 7.44-7.34 (m, 3H), 4.57 (td, J=8.0, 3.0 Hz, 0.4H), 4.48-4.42 (m, 0.6H), 4.30-4.10 (m, 4H), 3.82 (d, J=10.0 Hz, 0.4H), 3.54-3.47 (m, 1H), 3.44-3.36 (m, 1.6H), 3.02-2.93 (m, 0.6H), 2.80-2.71 (m, 0.4H), 2.26-2.17 (m, 0.4H), 2.20-1.56 (m, 3.6H), 1.29-1.19 (m, 6H), 1.01-0.99 (m, 3H); $^{13}$C NMR (125 MHz, CDCl$_3$) mixture of diastereomers and rotamers: δ 171.51, 170.63, 169.34, 169.20, 168.88, 168.68, 136.88, 136.82, 130.24, 130.14, 128.16, 128.10, 127.69, 127.61, 61.37, 61.25, 61.21, 61.17, 59.92, 59.05, 55.48, 51.99, 50.81, 37.31, 35.29, 29.42, 26.82, 25.40, 25.12, 14.12, 14.09, 14.02, 14.00, 12.97, 12.49; HRMS (ESI) m z calcd for $C_{20}H_{28}NO_5$ [(M+H)$^+$] 362.1962, found 362.19642. IR (film) 2977, 1747, 1726, 1627, 1394, 1265, 1174, 1150, 1027, 792, 700 cm$^{-1}$.

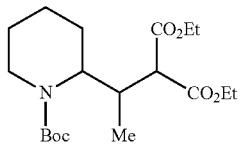 [SMILES: CCOC(=O)C(C(=O)OCC)C(C)C1CCCCN1C(=O)OC(C)(C)C]

(±)-Diethyl 2-(1-(1-(tert-butoxycarbonyl)piperidin-2-yl)ethyl)malonate: According to the general procedure, Ir[dF(CF$_3$)ppy)]$_2$(dtbbpy)PF$_6$ (2.2 mg, 2 μmol, 0.01 equiv.), Boc-Pip-OH (45.8 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (20% ethyl acetate/hexane) as a pale yellow oil (70 mg, 94%). $^1$H NMR (500 MHz, CDCl$_3$) mixture of diastereomers: δ 4.26-3.95 (m, 6H), 3.43 (d, J=4.5 Hz, 1H), 2.79-2.68 (m, 2H), 1.80-1.78 (m, 0.4H), 1.71-1.69 (m, 0.6H), 1.58-1.49 (m, 5H), 1.44 (s, 9H), 1.30-1.24 (m, 6H), 1.07 (d, J=6.5 Hz, 1.3H), 0.99 (d, J=7.0 Hz, 1.7H); $^{13}$C NMR (125 MHz, CDCl$_3$) mixture of diastereomers: δ 169.87, 169.24, 168.52, 168.24, 155.16, 155.14, 79.50, 79.39, 61.49, 61.39, 61.17, 60.91, 53.37, 53.14, 31.97, 31.70, 28.49, 28.45, 26.18, 25.39, 19.04, 18.89, 14.21, 14.14, 14.11, 13.80, 12.90; HRMS (ESI) m/z calcd for $C_{19}H_{33}NNaO_6$ [(M+Na)$^+$] 394.2206, found 394.2192. IR (film) 2977, 2935, 1687, 1150, 1028, 866 cm$^{-1}$;

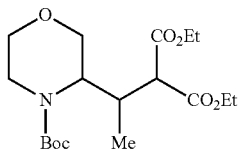 [SMILES: CCOC(=O)C(C(=O)OCC)C(C)C1COCCN1C(=O)OC(C)(C)C]

(±)-Diethyl 2-(1-(4-(tert-butoxycarbonyl)morpholin-3-yl)ethyl)malonate: According to the general procedure, Ir[dF(CF$_3$)ppy)]$_2$(dtbbpy)PF$_6$ (2.2 mg, 2 μmol, 0.01 equiv.), Boc-Morph-OH (46.2 mg, 0.2 mmol, 1.0 equiv), diethyl ethylidenemalonate (37.3 mg, 0.20 mmol, 1.0 equiv), K$_2$HPO$_4$ (42.0 mg, 0.24 mmol, 1.2 equiv), and 0.5 mL of DMF were used. The product was isolated by flash chromatography (20% ethyl acetate/hexane) as a pale yellow oil (71 mg, 95%). $^1$H NMR (500 MHz, CDCl$_3$) mixture of diastereomers: δ 4.23-4.10 (m, 4H), 4.01-3.78 (m, 4H), 3.51-3.44 (m, 3H), 3.13-3.03 (m, 1H), 2.93-2.85 (m, 1H), 1.46 (s, 4.5H), 1.45 (s, 4.5H); 1.30-1.25 (m, 6H), 1.16 (d, J=7.0 Hz, 1.5H), 1.05 (d, J=7.0 Hz, 1.5H); $^{13}$C NMR (125 MHz, CDCl$_3$) mixture of diastereomers: δ 168.83, 168.26, 168.22, 154.76, 154.59, 80.28, 67.21, 67.14, 61.48, 61.27, 60.97, 52.90, 52.66, 31.21, 28.40, 28.36, 14.21, 14.16, 14.14, 14.09, 13.67, 12.80; HRMS (ESI) m/z calcd for $C_{18}H_{31}NNaO_7$ [(M+Na)$^+$] 396.1998, found 396.1995. IR (film) 2978, 1729, 1690, 1103, 866 cm$^{-1}$;

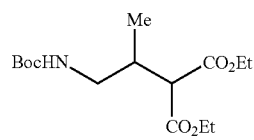

(±)-Diethyl 2-(1-((tert-butoxycarbonyl)amino)propan-2-yl)malonate: According to the general procedure, Ir[dF(CF$_3$)ppy)]$_2$(dtbbpy)PF$_6$ (2.2 mg, 2 μmol, 0.01 equiv.), Boc-Gly-OH (35.0 mg, 0.2 mmol, 1.0 equiv), diethyl ethylidenemalonate (37.3 mg, 0.2 mmol, 1.0 equiv), K$_2$HPO$_4$ (42.0 mg, 0.24 mmol, 1.2 equiv), and 0.5 mL of DMF were used. The product was isolated by flash chromatography (25% ethyl acetate/hexane) as a pale yellow oil (60 mg, 94%).

$^1$H NMR (500 MHz, CDCl$_3$) mixture of diastereomers: δ 4.71 (s, 1H), 4.20 (qd, J=7.0 Hz, J=2.0 Hz, 4H), 3.31 (d, J=7.5 Hz, 1H), 3.22-3.12 (m, 2H), 2.48-2.43 (m, 1H), 1.43 (s, 9H), 1.27 (d, J=7.5 Hz, 6H), 1.01 (d, J=7.0 Hz, 3H); $^{13}$C NMR (125 MHz, CDCl$_3$) mixture of diastereomers: δ 168.78, 168.56, 155.96, 79.21, 61.41, 61.35, 55.02, 44.18, 34.08, 28.37, 15.52, 14.09, 14.06; HRMS (ESI) m/z calcd for $C_{15}H_{27}NNaO_6$ [(M+Na)$^+$] 340.1736, found 340.1739. IR (film) 2978, 1714, 1515, 1246, 1164, 1030 cm$^{-1}$;

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method of peptide C-terminal residue functionalization comprising:
   providing a reaction mixture including a Michael acceptor and a peptide, wherein the peptide comprises a C-terminal residue comprising a carboxyl group; and
   coupling the Michael acceptor with the peptide via a mechanism including selective decarboxylation of the carboxyl group of the C-terminal residue of the peptide over another carboxyl group of the peptide.

2. The method of claim 1, wherein coupling of the peptide and the Michael acceptor provides a 1,4-addition adduct.

3. The method of claim 1, wherein the Michael acceptor is of the formula $$\underset{R^1}{\overset{R^2}{\diagup}} C=C \diagdown EWG$$

wherein EWG is an electron withdrawing group selected from the group consisting of formyl, keto, ester, cyano, amide and sulfone and $R^1$ and $R^2$ are independently selected from the group consisting of -hydrogen, -alkyl, -cycloalkyl, -aryl, -alkyl-aryl and -ester.

4. The method of claim 1, wherein the peptide comprises at least three amino acids.

5. The method of claim 1, wherein the peptide comprises at least five amino acids.

6. The method of claim 1, wherein the peptide is a protein.

7. The method of claim 1, wherein the selective decarboxylation occurs subsequent to formation of a carboxyl radical at a peptide residue.

8. The method of claim 7, wherein carboxyl radical formation is initiated by a single electron transfer (SET) process.

9. The method of claim 8, wherein the SET process is oxidative.

10. The method of claim 8, wherein the SET process is reductive.

11. The method of claim 7, wherein an α-amino radical is formed by the decarboxylation at the peptide residue.

12. The method of claim 11, wherein the α-amino radical undergoes conjugate addition with the Michael acceptor.

13. The method of claim 8, wherein the reaction mixture further comprises a catalyst for initiating the SET process.

14. The method of claim 13 wherein the catalyst is transition metal catalyst.

15. The method of claim 13, wherein the catalyst is a photoredox catalyst.

16. The method of claim 15, wherein the photoredox catalyst is an iridium complex.

17. The method of claim 16, wherein the iridium complex is heteroleptic.

18. The method of claim 17, wherein the heteroleptic iridium complex is selected from the group consisting of Ir[dF(CF$_3$)ppy]$_2$(dtbbpy)$^+$ and Ir(ppy)$_2$(dtbbpy)$^+$.

19. The method of claim 8, wherein the SET process is initiated electrochemically.

20. The method of claim 1, wherein the carboxyl group of the C-terminal residue is an α-carboxyl group of the C-terminal residue.

21. The method of claim 20, wherein the coupling is selective for the α-carboxyl group of the C-terminal residue over a side-chain carboxyl group of the peptide.

22. The method of claim 1, wherein the reaction mixture further comprises a photocatalyst.

* * * * *

SEQUENCE LISTING

```
<160> NUMBER OF SEQ ID NOS: 53

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 1

Ala Ala Phe Gly Ala Phe Gly Val
1               5
```

-continued

```
<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Leu Gly Pro
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Ala Pro Gly
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba
<220> FEATURE:
<221> NAME/KEY: MOD_RES
<222> LOCATION: (5)..(5)
<223> OTHER INFORMATION: Glu(OtBu)

<400> SEQUENCE: 4

Xaa Phe Met Leu Glu
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu(tBu)

<400> SEQUENCE: 5

Phe Met Leu Glu Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba
```

```
<220> FEATURE:
<221> NAME/KEY: MOD_RES
<222> LOCATION: (3)..(3)
<223> OTHER INFORMATION: Thr(tBu)
<220> FEATURE:
<221> NAME/KEY: MOD_RES
<222> LOCATION: (5)..(5)
<223> OTHER INFORMATION: Trp(Boc)

<400> SEQUENCE: 6

Xaa Val Thr Phe Trp
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Thr(tBu)
<220> FEATURE:
<221> NAME/KEY: MOD_RES
<222> LOCATION: (4)..(4)
<223> OTHER INFORMATION: Trp(Boc)

<400> SEQUENCE: 7

Val Thr Phe Trp Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba
<220> FEATURE:
<221> NAME/KEY: MOD_RES
<222> LOCATION: (3)..(3)
<223> OTHER INFORMATION: Arg(Boc)2
<220> FEATURE:
<221> NAME/KEY: MOD_RES
<222> LOCATION: (4)..(4)
<223> OTHER INFORMATION: Ser(tBu)

<400> SEQUENCE: 8

Xaa Phe Arg Ser Ala
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg(Boc)2
<220> FEATURE:
<221> NAME/KEY: MOD_RES
<222> LOCATION: (4)..(4)
<223> OTHER INFORMATION: Ser(tBu)
```

```
<400> SEQUENCE: 9

Phe Arg Ala Ser Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba
<220> FEATURE:
<221> NAME/KEY: MOD_RES
<222> LOCATION: (3)..(3)
<223> OTHER INFORMATION: Gln(Trt)
<220> FEATURE:
<221> NAME/KEY: MOD_RES
<222> LOCATION: (5)..(5)
<223> OTHER INFORMATION: Lys(Boc)

<400> SEQUENCE: 10

Xaa Phe Gln Leu Lys
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln(Trt)
<220> FEATURE:
<221> NAME/KEY: MOD_RES
<222> LOCATION: (4)..(4)
<223> OTHER INFORMATION: Lys(Boc)

<400> SEQUENCE: 11

Phe Gln Leu Lys Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba
<220> FEATURE:
<221> NAME/KEY: MOD_RES
<222> LOCATION: (3)..(3)
<223> OTHER INFORMATION: (Me)Ala
<220> FEATURE:
<221> NAME/KEY: MOD_RES
<222> LOCATION: (4)..(4)
<223> OTHER INFORMATION: Tyr(tBu)

<400> SEQUENCE: 12

Xaa Phe Ala Tyr Val
1               5
```

```
<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (Me)Ala
<220> FEATURE:
<221> NAME/KEY: MOD_RES
<222> LOCATION: (3)..(3)
<223> OTHER INFORMATION: Tyr(tBu)

<400> SEQUENCE: 13

Phe Ala Tyr Val Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba
<220> FEATURE:
<221> NAME/KEY: MOD_RES
<222> LOCATION: (3)..(3)
<223> OTHER INFORMATION: Pra
<220> FEATURE:
<221> NAME/KEY: MOD_RES
<222> LOCATION: (5)..(5)
<223> OTHER INFORMATION: Lys(Boc)

<400> SEQUENCE: 14

Xaa Phe Xaa Ala Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pra
<220> FEATURE:
<221> NAME/KEY: MOD_RES
<222> LOCATION: (4)..(4)
<223> OTHER INFORMATION: Lys(Boc)

<400> SEQUENCE: 15

Phe Xaa Ala Lys Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Aba
<220> FEATURE:
<221> NAME/KEY: MOD_RES
<222> LOCATION: (5)..(5)
<223> OTHER INFORMATION: His(Trt)

<400> SEQUENCE: 16

Xaa Phe Leu Ala His
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: His(Trt)

<400> SEQUENCE: 17

Phe Leu Ala His Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahda

<400> SEQUENCE: 18

Xaa Phe Leu Ala Phe
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Leu Ala Phe Glu
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba

<400> SEQUENCE: 20

Xaa Phe Leu Ala Phe
```

```
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Leu Ala Phe Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba
<220> FEATURE:
<221> NAME/KEY: MOD_RES
<222> LOCATION: (5)..(5)
<223> OTHER INFORMATION: Phe(4-Br)

<400> SEQUENCE: 22

Xaa Phe Leu Ala Phe
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe(4-Br)

<400> SEQUENCE: 23

Phe Leu Ala Phe Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba(2-Ph)

<400> SEQUENCE: 24

Xaa Phe Leu Ala Phe
1               5

<210> SEQ ID NO 25
<211> LENGTH: 5
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phenyl-Phe

<400> SEQUENCE: 25

Phe Leu Ala Phe Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (Me)Aba(4-iBu)

<400> SEQUENCE: 26

Xaa Phe Leu Ala Phe
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (Me)Leu

<400> SEQUENCE: 27

Phe Leu Ala Phe Leu
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (3-Ac)pa

<400> SEQUENCE: 28

Xaa Phe Leu Ala Phe
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acc
```

<400> SEQUENCE: 29

Phe Leu Ala Phe Xaa
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (3-Acp)pa

<400> SEQUENCE: 30

Xaa Phe Leu Ala Phe
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acpc

<400> SEQUENCE: 31

Phe Leu Ala Phe Xaa
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba

<400> SEQUENCE: 32

Xaa Phe Leu Ala Phe
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu(OtBu)

<400> SEQUENCE: 33

Phe Ala Pro Glu Leu Phe Ala Gly
1               5

```
<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba
<220> FEATURE:
<221> NAME/KEY: MOD_RES
<222> LOCATION: (7)..(7)
<223> OTHER INFORMATION: Thr(tBu)
<220> FEATURE:
<221> NAME/KEY: MOD_RES
<222> LOCATION: (9)..(9)
<223> OTHER INFORMATION: Tyr(tBu)

<400> SEQUENCE: 34

Xaa Ala Phe Leu Pro Ala Thr Val Tyr Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Thr(tBu)
<220> FEATURE:
<221> NAME/KEY: MOD_RES
<222> LOCATION: (8)..(8)
<223> OTHER INFORMATION: Tyr(tBu)

<400> SEQUENCE: 35

Ala Phe Leu Pro Ala Thr Val Tyr Leu Gly
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aba
<220> FEATURE:
<221> NAME/KEY: MOD_RES
<222> LOCATION: (5)..(5)
<223> OTHER INFORMATION: Lys(Boc)
<220> FEATURE:
<221> NAME/KEY: MOD_RES
<222> LOCATION: (12)..(12)
<223> OTHER INFORMATION: Glu(OtBu)

<400> SEQUENCE: 36

Xaa Ala Leu Phe Lys Pro Ala Phe Ala Leu Pro Glu Leu Phe Val
1               5                   10                  15

<210> SEQ ID NO 37
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(Boc)
<220> FEATURE:
<221> NAME/KEY: MOD_RES
<222> LOCATION: (11)..(11)
<223> OTHER INFORMATION: Glu(OtBu)

<400> SEQUENCE: 37

Ala Leu Phe Lys Pro Ala Phe Ala Leu Pro Glu Leu Phe Val Gly
1               5                   10                  15

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Gly Ala Phe Gly Pro
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Gly Ala Phe Gly Ala
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 40

Ala Ala Phe Gly Ala Phe Gly Pro
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 41

Ala Ala Phe Gly Ala Phe Gly Gly
1               5
```

```
<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 42

Ala Ala Phe Gly Ala Phe Gly Leu
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 43

Ala Ala Phe Gly Ala Phe Gly Ile
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 44

Ala Ala Phe Gly Ala Phe Gly Phe
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (8)..(8)
<223> OTHER INFORMATION: Ser(Bzl)

<400> SEQUENCE: 45

Ala Ala Phe Gly Ala Phe Gly Ser
1               5

<210> SEQ ID NO 46
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Gln Ile Phe Val Lys
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Leu Thr Gly Lys
1               5

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Ile Thr Leu Glu Val Glu Pro Ser Asp Thr Ile Glu Asn Val Lys
1               5                   10                  15

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Gln Glu Lys
1

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Gly Ile Pro Pro Asp Gln Gln Arg Leu Ile Phe Ala Gly Lys
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51
```

```
Gln Leu Glu Asp Gly Arg Thr Leu Ser Asp Tyr Asn Ile Gln Lys
1               5                   10                  15

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Ser Thr Leu His Leu Val Leu Arg Leu Arg Gly Gly
1               5                   10

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Gly Pro Gly Pro
1               5
```